United States Patent
Izatt et al.

(10) Patent No.: US 9,259,150 B2
(45) Date of Patent: Feb. 16, 2016

(54) SYSTEMS FOR COMPREHENSIVE FOURIER DOMAIN OPTICAL COHERENCE TOMOGRAPHY (FDOCT) AND RELATED METHODS

(71) Applicant: Bioptigen, Inc., Morrisville, NC (US)

(72) Inventors: Joseph A. Izatt, Raleigh, NC (US); Eric L. Buckland, Hickory, NC (US); Bradley A. Bower, Hillsborough, NC (US); Robert H. Hart, Cary, NC (US)

(73) Assignee: Bioptigen, Inc., Durham, NC (US)

( * ) Notice: Subject to any disclaimer, the term of this patent is extended or adjusted under 35 U.S.C. 154(b) by 0 days.

(21) Appl. No.: 14/148,100

(22) Filed: Jan. 6, 2014

(65) Prior Publication Data

US 2014/0160431 A1    Jun. 12, 2014

Related U.S. Application Data

(63) Continuation of application No. 12/910,184, filed on Oct. 22, 2010, now Pat. No. 8,625,104, which is a continuation-in-part of application No. 12/887,891, filed on Sep. 22, 2010, now Pat. No. 8,348,427.

(60) Provisional application No. 61/254,465, filed on Oct. 23, 2009.

(51) Int. Cl.
*G01B 11/02*   (2006.01)
*A61B 3/10*    (2006.01)
*G01B 9/02*    (2006.01)

(52) U.S. Cl.
CPC ............. *A61B 3/102* (2013.01); *G01B 9/0201* (2013.01); *G01B 9/02078* (2013.01); *G01B 9/02091* (2013.01)

(58) Field of Classification Search
CPC ........................... A61B 3/102; G01B 9/02091
See application file for complete search history.

(56) References Cited

U.S. PATENT DOCUMENTS

| | | | |
|---|---|---|---|
| 4,834,474 A | 5/1989 | George et al. | |
| 5,220,450 A | 6/1993 | Iizuka | 359/205.1 |
| 7,019,838 B2 | 3/2006 | Izatt et al. | |
| 7,224,867 B2 | 5/2007 | Mossberg | |
| 7,336,366 B2 | 2/2008 | Choma et al. | |
| 7,400,410 B2 | 7/2008 | Baker et al. | 356/498 |
| 7,519,248 B2 | 4/2009 | Iazikov et al. | |
| 7,602,500 B2 | 10/2009 | Izatt et al. | |

(Continued)

FOREIGN PATENT DOCUMENTS

| | | |
|---|---|---|
| EP | 1 870 029 A1 | 6/2006 |
| EP | 1 870 030 A1 | 6/2006 |
| EP | 1 870 028 A1 | 12/2007 |

OTHER PUBLICATIONS

Invitation to Pay Additional Fees corresponding to International Application No. PCT/US2010/053702; Date of Mailing: Dec. 22, 2010; 7 pages.

(Continued)

*Primary Examiner* — Kara E Geisel
*Assistant Examiner* — Shawn Decenzo
(74) *Attorney, Agent, or Firm* — Myers Bigel Sibley & Sajovec

(57) ABSTRACT

Optical coherence tomography systems for imaging a whole eye are provided including a sample arm including focal optics that are configured to rapidly switch between at least two scanning modes in less than about 1.0 second.

2 Claims, 48 Drawing Sheets

(56) References Cited

U.S. PATENT DOCUMENTS

| | | | |
|---|---|---|---|
| 7,719,692 B2 | 5/2010 | Izatt et al. | |
| 7,742,174 B2 | 6/2010 | Izatt et al. | |
| 7,744,221 B2 | 6/2010 | Wei et al. | |
| 7,800,759 B2* | 9/2010 | Lai et al. | 356/497 |
| 7,830,525 B2 | 11/2010 | Buckland et al. | |
| 7,843,572 B2 | 11/2010 | Tearney et al. | |
| 7,903,257 B2 | 3/2011 | de Boer et al. | |
| 8,033,665 B2 | 10/2011 | Ferguson et al. | |
| 8,042,944 B2 | 10/2011 | De Vries et al. | |
| 8,120,779 B2* | 2/2012 | Buckland et al. | 356/479 |
| 8,348,427 B2 | 1/2013 | Buckland et al. | |
| 8,625,104 B2 | 1/2014 | Izatt et al. | |
| 8,654,104 B2 | 2/2014 | Reisman et al. | |
| 8,820,931 B2* | 9/2014 | Walsh et al. | 351/206 |
| 2002/0039231 A1 | 4/2002 | Sela | |
| 2004/0066489 A1 | 4/2004 | Benedikt et al. | |
| 2004/0239943 A1 | 12/2004 | Izatt et al. | |
| 2006/0164639 A1 | 7/2006 | Horn et al. | |
| 2007/0030483 A1 | 2/2007 | Everett et al. | |
| 2007/0030484 A1 | 2/2007 | Sobczynski | |
| 2007/0053635 A1 | 3/2007 | Iazikov et al. | |
| 2007/0076217 A1 | 4/2007 | Baker et al. | |
| 2007/0177145 A1 | 8/2007 | Ohishi et al. | |
| 2007/0291277 A1* | 12/2007 | Everett et al. | 356/497 |
| 2008/0002183 A1 | 1/2008 | Yatagai et al. | |
| 2008/0106696 A1 | 5/2008 | Buckland et al. | |
| 2008/0170219 A1 | 7/2008 | Sarunic et al. | |
| 2008/0181477 A1 | 7/2008 | Izatt et al. | |
| 2009/0040521 A1 | 2/2009 | Hu et al. | |
| 2010/0094576 A1 | 4/2010 | de Boer et al. | |

OTHER PUBLICATIONS

International Search Report and Written Opinion of the International Searching Authority corresponding to international Application No. PCT/US2010/053702, Date of Mailing: Mar. 10, 2011; 16 pages.

Akcay et al. "Spectral shaping to improve the point spread function in optical coherence tomography", Oct. 15, 2003, vol. 28, No. 20, Optics Letters, pp. 1921-1923.

Baikoff, Phakic anterior chamber intraocular lenses, international Ophthalmology Clinics, 31(1), p. 75-86 (1991).

Bajraszewski et al. Improved spectral optical coherence tomography using optical frequency comb, Mar. 17, 2008, vol. 16, No. 6, Optics Express, pp. 4163-4176.

Balmer et al. "Diagnosis and current management of retinoblastoma," Oncogene 25, 5341-5349 (2006).

Brancato et al. "Optical coherence tomography (OCT) in retinal angiomatous proliferation (RAP)," European Journal of Ophthalmology, vol. 12, No. 6, 2002, pp. 467-472, Italy.

Broaddus et al. "Incidence of retinoblastoma in the USA: 1975-2004," British Journal of Ophthalmology 2009; 93, pp. 21-23.

Choma et al. "Sensitivity advantage of swept source and Fourier domain optical coherence tomography", Sep. 8, 2003, vol. 11, No. 18, Optics Express, pp. 2183-2189.

Congdon et al. "Causes and prevalence of visual impairment among adults in the United States," Arch. Ophthalmol., Vo. 122, Apr. 2004 pp. 477-485.

de Boer et al. "Improved signal-to-noise ratio in spectral-domain compared with time-domain optical coherence tomography," Nov. 1, 2003, vol. 28, No. 21, Optics Letters, pp. 2067-2069.

Glasier et al. "High Resolution Ultrasound with Doppler: a diagnostic adjunct in orbital and ocular lesions in children", Pediatric Radiology 22, 174-178 (1992).

Goes, "Visual Results Following Implantation of a Refractive Multifocal IOL in One Eye and a Diffractive Multifocal IOL in the Contralateral Eye," Journal of Refractive Surgery, vol. 24 Mar. 2008, pp. 300-305.

Grulkowski et al. "Anterior segment imaging with Spectral OCT system using a high-speed CMOS camera", Mar. 16, 2009, vol. 17, No. 6 Optics Express, pp. 4842-4858.

Hee et al. "Optical Coherence Tomography of the Human Retina," Arch. Ophthalmol, vol. 113, Mar. 2005, pp. 325-332.

Hee et al., "Optical Coherence Tomography of Age-related Macular Degeneration and Choroidal Neovascularization", Ophthalmology, vol. 103, No. 8, Aug. 1996; pp. 1260-1270.

Hu et al. "Fourier domain optical coherence tomography with a linear-in-wavenumber spectrometer", Dec. 15, 2007, vol. 32, No. 24, Optics Letters, pp. 3525-3527.

Huang et al. "Optical Coherence Tomography.," Science, vol. 254, Nov. 22, 1991, pp. 1178-1181.

International Preliminary Report on Patentability corresponding to International Application No. PCT/JP2005/004800; Date of Issuance of this report: Feb. 13, 2007.

International Search Report and Written Opinion of the International Searching Authority corresponding to International Application No. PCT/US2010/049793; Date of Mailing: Apr. 8, 2011; 15 pages.

Invitation to Pay Additional Fees for International Application No. PCT/US2010/049793; Date of Mailing: Feb. 2, 2011; 7 pages.

Izatt et al. "High-speed In Vivo retinal imaging with optical coherence tomography," Investigative Ophthalmology & Visual Science, Mar. 15, 1994, vol. 35, No. 4, p. 1729.

Izatt et al. "In Vivo Imaging of the Human Retina With Optical Coherence Tomography," Investigative Ophthalmology & Visual Science vol. 34, p. 761 (1993).

Izatt et al. "Optical coherence microscopy in scaterring media", Optics Letters, vol. 19, No. 8, Apr. 15, 1994, pp. 590-592.

Izatt et al. "Quantitative assessment of cataract development with optical coherence domain reflectometry and optical coherence tomography," Investigative Ophthalmology & Visual Science vol. 33, p. 1300 (1992).

Izatt et al, "Theory of Optical Coherence Tomography," in Optical Coherence Tomography: Technology and Applications, Springer, (Eds.)W. Drexler, and J. G. Fujimoto, 2008, ISBN 978-3-540-77549-2, pp. 47-72.

Izatt et al. "Micrometer-Scale Resolution Imaging of the Anterior Eye In Vivo With Optical Coherence Tomography," Arch Ophthalmol, vol. 112, Dec. 1994, pp. 1584-1589.

Leitgeb et al. "Performance of fourier domain vs. time domain optical coherence tomography", Apr. 21, 2003, vol. 11, No. 8, Optics Express, pp. 889-894.

Leitgeb et al. "Phase-shifting algorithm to achieve high-speed long-depth-range probing by frequency-domain optical coherence tomography", Nov. 15, 2003, vol. 28, No. 22, Optics Letters, pp. 2201-2203.

Mafee et al. "Retinoblastoma and Simulating Lesions: Role of CT and MR imaging", Imaging in Ophthalmology, Part II; Radiologic Clinics of North America, vol. 25, No. 4, Jul. 1987, pp. 667-682.

Monteiro et al. "Optical coherence tomography analysis of axonal loss in band atrophy of the optic nerve," British Journal of Ophthalmology 2004; 88: 896-899.

Peyster et al. "Intraocular Tumors: Evaluation with MR imaging", Radiology, Sep. 1988; 168: 773-779.

Puliafito et al. "Imaging of Macular Diseases with Optical Coherence Tomography," Ophthalmology, vol. 102, No. 2, Feb. 1995, pp. 217-229.

Quigley et al. "The number of people with glaucoma worldwide in 2010 and 2020," British Journal of Ophthalmology 2006 90: 262-267.

Rein et al. "The Economic Burden of Major Adult Visual Disorders in the United States," Arch. of Ophthalmol., vol. 124, Dec. 2006, pp. 1754-1760.

Takada, "High-Resolution OFDR with Incorporated Fiber-Optic Frequency Encoder", IEEE Photonics Technology Letters, vol. 4, No. 9, Sep. 1992, pp. 1069-1072.

Tao et al. "High-speed complex conjugate resolved retinal spectral domain optical coherence tomography using sinusoidal phase modulation," Optics Letters, vol. 32, No. 20, Oct. 15, 2007, pp. 2918-2920.

Traub, "Constant-dispersion grism spectrometer for channeled spectra," Journal of the Optical Society of America A 7, pp. 1779-1791, Sep. 1990, vol. 7, No. 9, Woodbury, NY, US.

Tripathi et al. "Spectral shaping for non-Gaussian source spectra in optical coherence tomography", Optics Letters, vol. 27, No. 6, Mar. 15, 2002, pp. 406-408.

(56) References Cited

OTHER PUBLICATIONS

Werner et al. "Phakic anterior chamber intralocular lenses," International Ophthalmology Clinics 41, 133-152 (2001).

Werner et al. "Phakic Posterior Chamber Intraocular Lenses," International Ophthalmology Clinics 41, pp. 153-174 (2001).

Wollstein et al. "Ultrahigh-Resolution Optical Coherence Tomography in Glaucoma," *Ophthalmology* vol. 112, No. 2, Feb. 2005; pp. 229-237.

Wollstein et al. "Comparison of Three Optical Coherence Tomography Scanning Areas for Detection of Glaucomatous Damage," *American Journal of Ophthalmology*, vol. 139, No. 1, Jan. 2005; pp. 39-43.

Yun et al. "High-speed spectral-domain optical coherence tomography at 1.3 µm wavelength," *Opt Express*. Dec. 29, 2003; 11 (26): 3598-3604.

Notification Concerning Transmittal of International Preliminary Report on Patentability, PCT/US2010/049793, Apr. 5, 2012.

Gelikonov et al., "Linear-Wavenumber Spectrometer for High-Speed Spectral-Domain Optical Coherence Tomography," Optics and Spectroscopy, 2009, vol. 105, No. 3, pp. 459-465.

Notification Concerning Transmittal of International Preliminary Report on Patentability, PCT/US2010/053702, Apr. 24, 2012.

Notification Concerning Transmittal of International Preliminary Report on Patentability, PCT/US2012/030251, Sep. 24, 2013, 11 pages.

\* cited by examiner

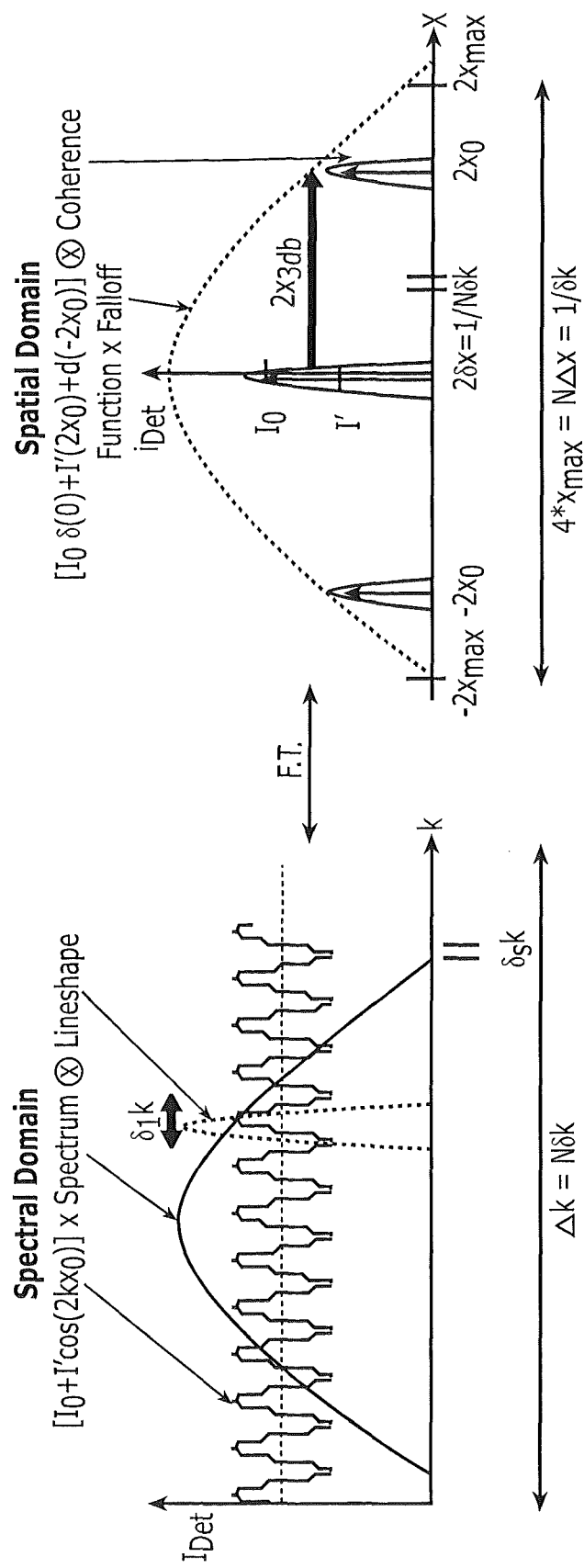

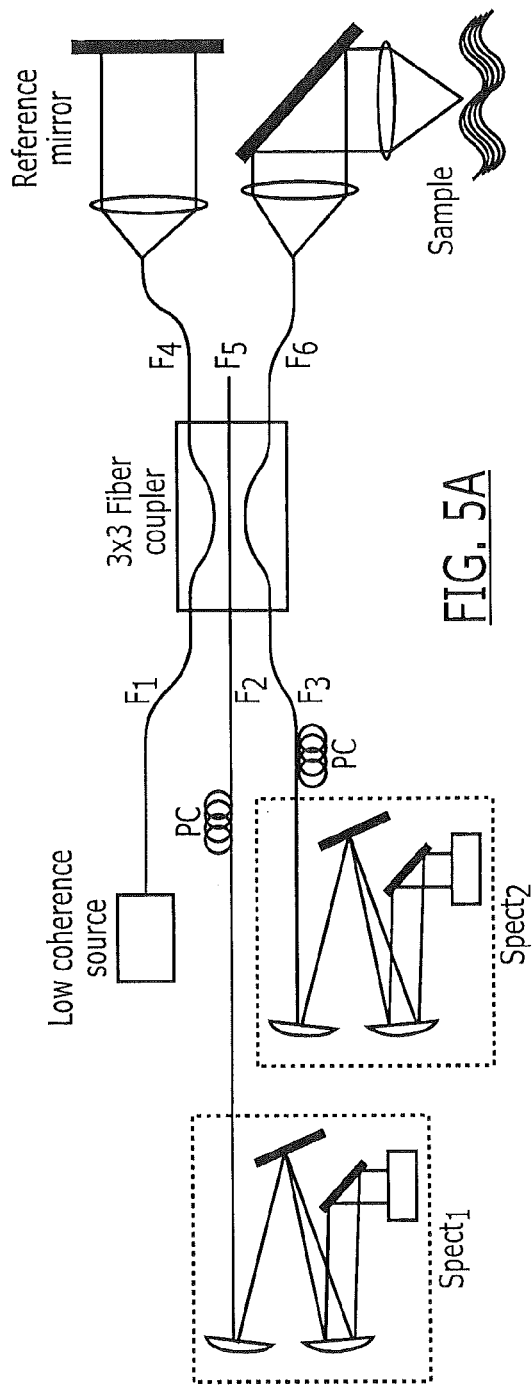
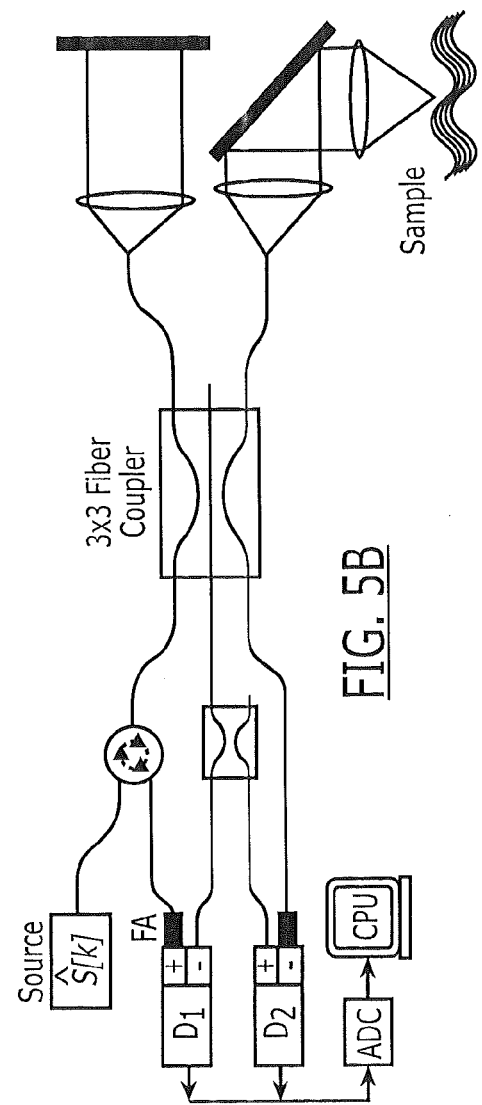
FIG. 5A
FIG. 5B

|  | | | | | | | |
|---|---|---|---|---|---|---|---|
| | Single-sided depth (air, mm) | 3.5 | 7 | 8 | 9 | 10 | |
| | Double Sided Depth (air, mm) | 7 | 14 | 16 | 18 | 20 | |
| 4096 | d_v (GHz) | 21.43 | 10.71 | 9.38 | 8.33 | 7.50 | |
| | spectrometer bandwidth (nm) | 206.44 | 103.22 | 90.32 | 80.28 | 72.25 | |
| 3 dB | usable source be (nm) | 128.40 | 64.20 | 56.17 | 49.93 | 44.94 | |
| um | resolution (um) | 2.42 | 4.85 | 5.54 | 6.24 | 6.93 | |
| 840 | central wavelength (nm) | | | 840 | | | |
| GRISM | prism material | | | Schott P-SF68 | | | |
| | prism index | | | 2.0052 | | | |
| | prism AOI (radians) | pi/8 | pi/8 | pi/8 | pi/8 | pi/8 | |
| | prism vertex angle (radians) | 0.36 | 0.66 | 0.65 | 0.65 | 0.65 | |
| | grating material | | | Schott B-270 | | | |
| | grating index | | | 1.523 | | | |
| | grating pitch (l/mm) | 450 | 400 | 340 | 300 | 270 | |
| | prism spot (mm) | 25 | 25 | 25 | 25 | 25 | |
| | focal length (mm) | 100 | 220 | 330 | 445 | 575 | |
| | k pixel.shift max (pix) | 0.42 | 0.49 | 0.39 | 0.33 | 0.37 | |

FIG. 17

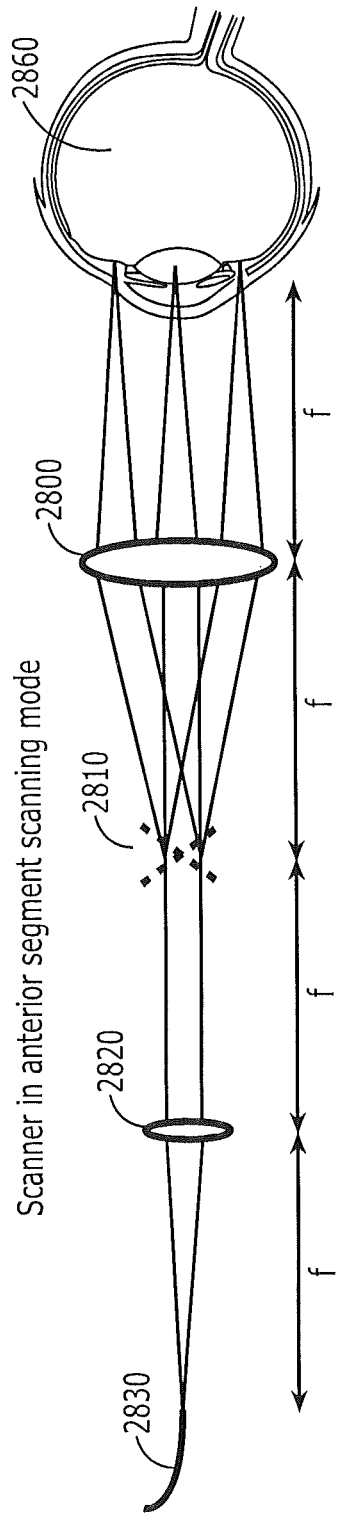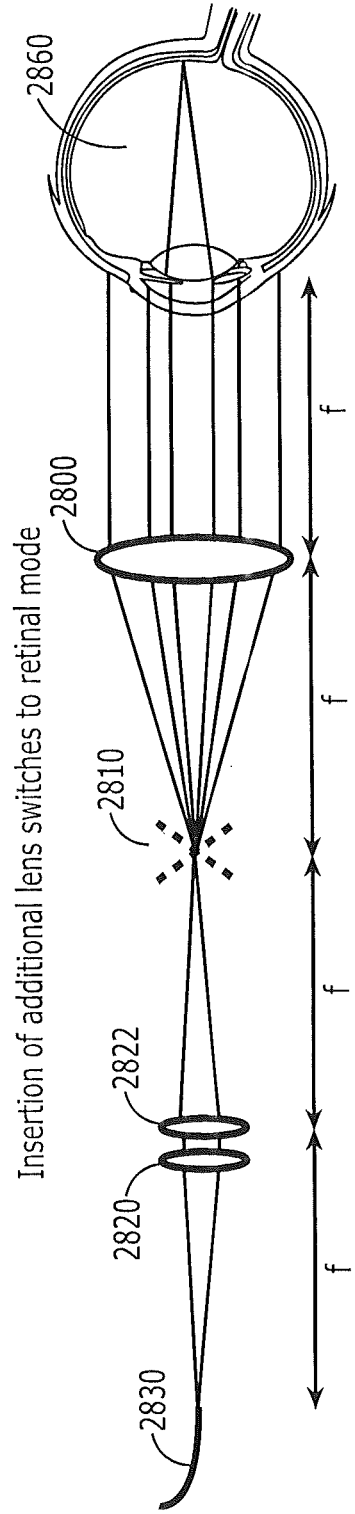
FIG. 28A
FIG. 28B

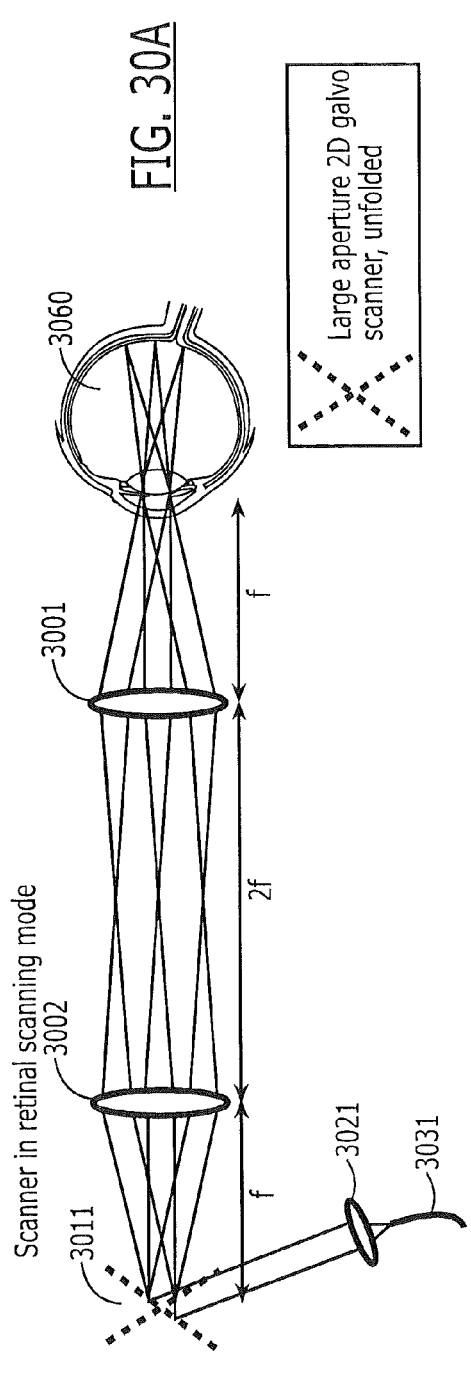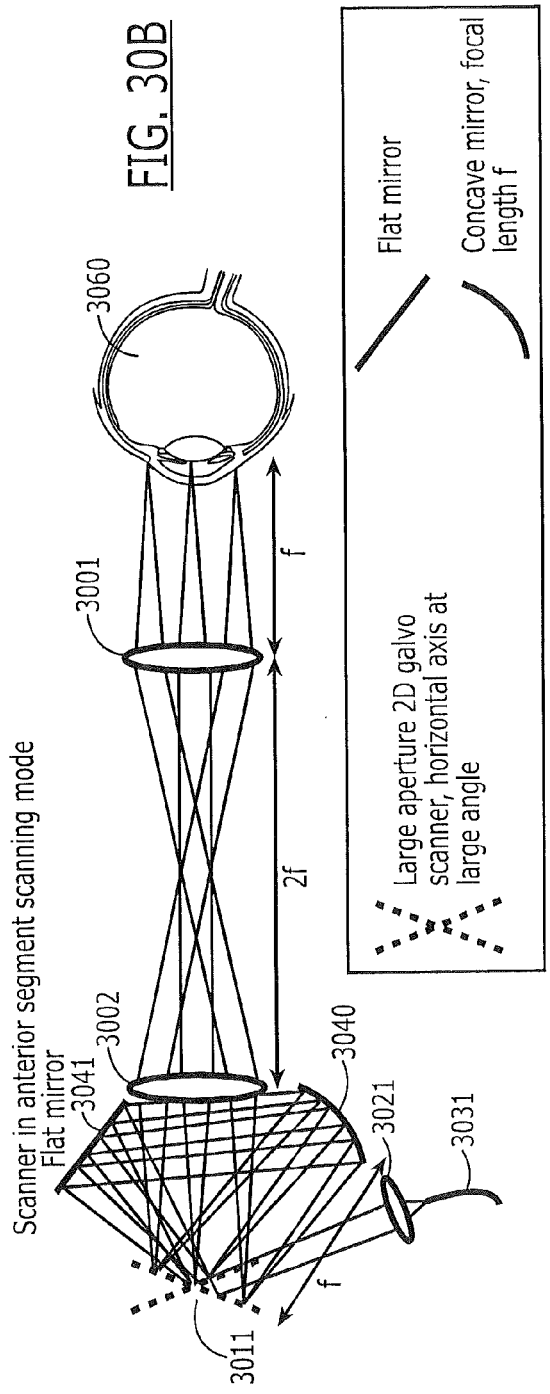

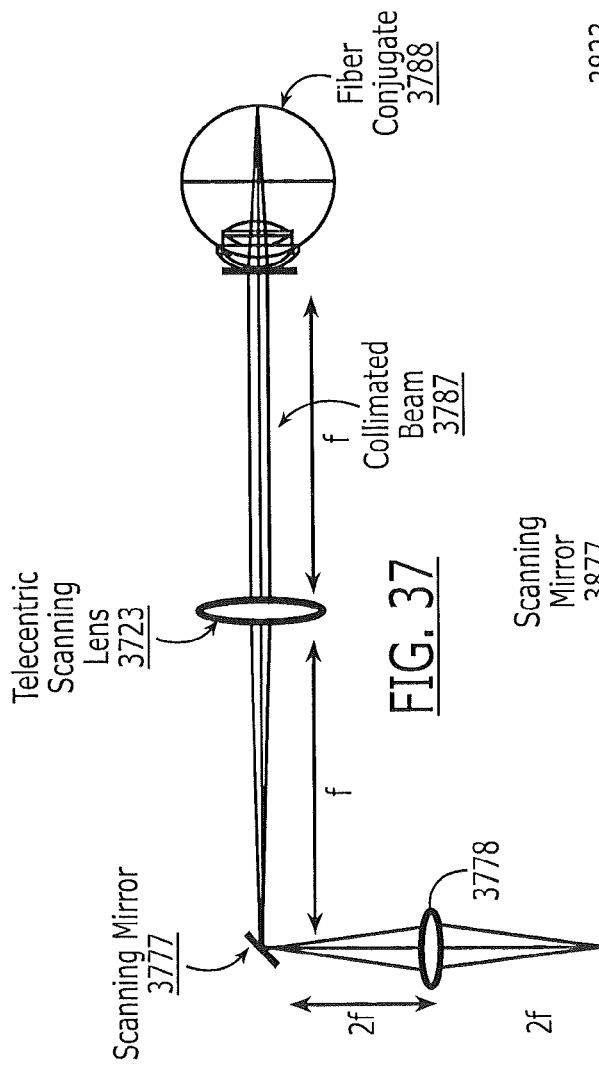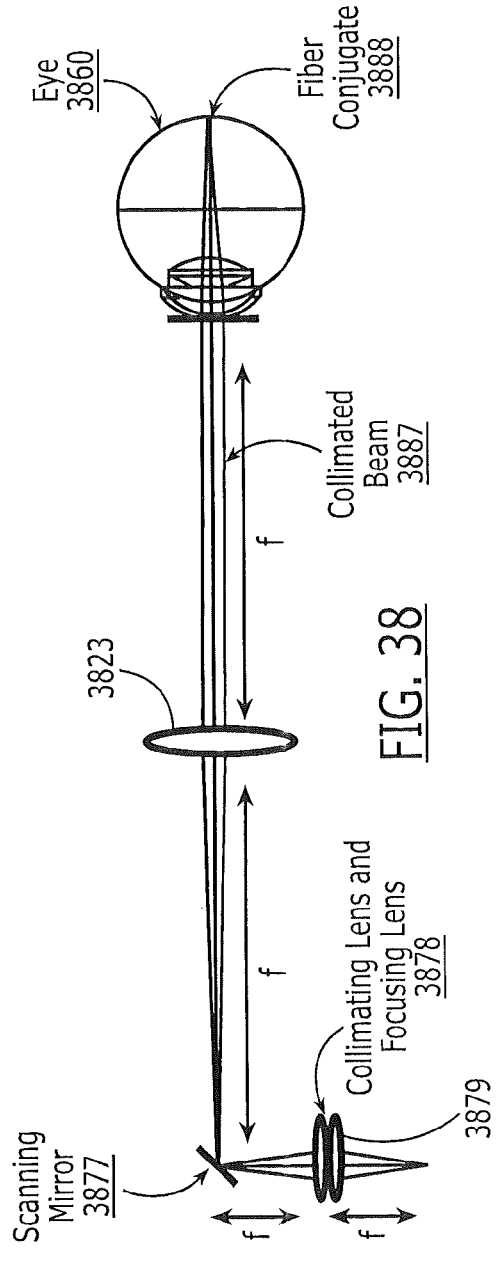

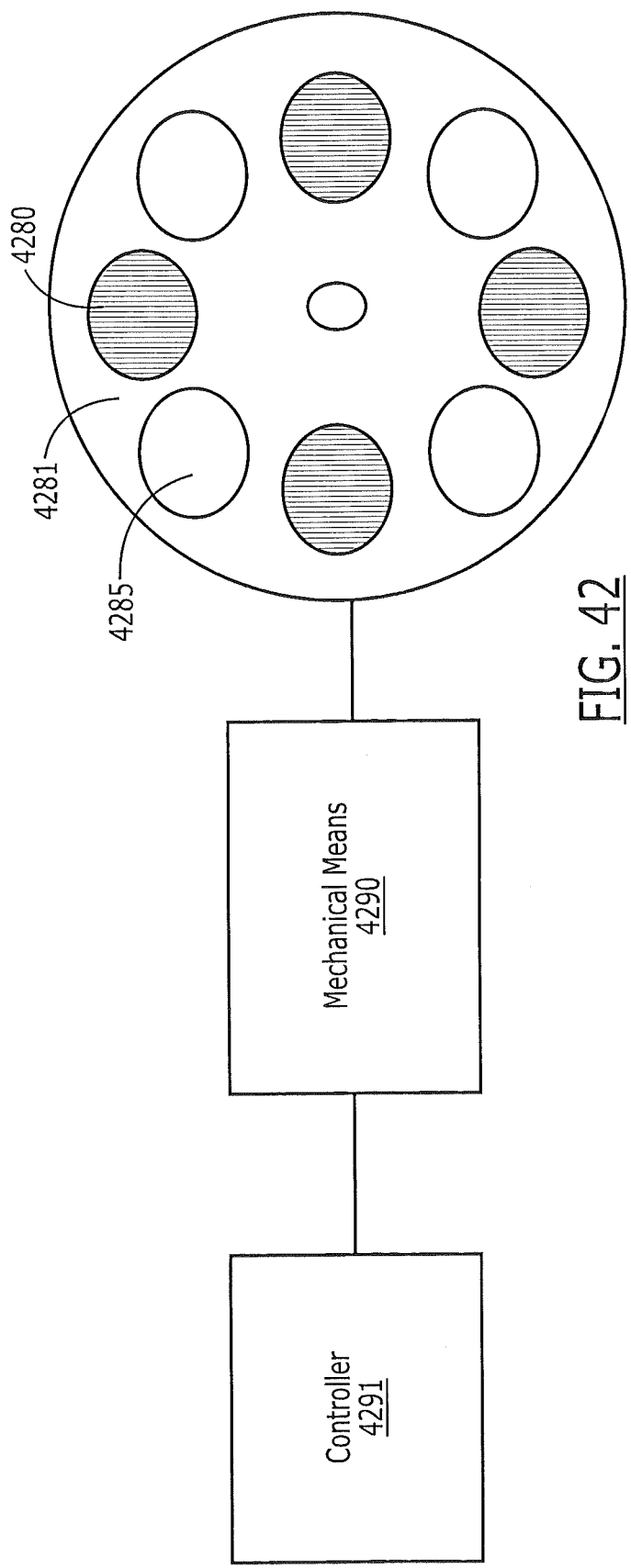

SYSTEMS FOR COMPREHENSIVE FOURIER DOMAIN OPTICAL COHERENCE TOMOGRAPHY (FDOCT) AND RELATED METHODS

CLAIM OF PRIORITY

The present application is a continuation of U.S. application Ser. No. 12/910,184, filed Oct. 22, 2010, which claims priority from U.S. Provisional Application No. 61/254,465, filed Oct. 23, 2009 and to U.S. patent application Ser. No. 12/887,891, filed on Sep. 22, 2010, now U.S. Pat. No. 8,348,427, the disclosures of which are hereby incorporated herein by reference as if set forth in their entirety.

STATEMENT OF GOVERNMENT SUPPORT

This invention was made with government support under grant numbers 2R44EY015585 and 2R43EY018021 awarded by National Institutes of Health, National Eye Institute. The United States Government has certain rights in this invention.

FIELD

The present inventive concept generally relates to imaging and, more particularly, to frequency domain optical coherence tomography (FDOCT) and related systems and methods.

BACKGROUND

Optical coherence tomography (OCT) is a noninvasive imaging technique that provides microscopic tomographic sectioning of biological samples. By measuring singly back-scattered light as a function of depth, OCT fills a valuable niche in imaging of tissue ultrastructure, providing subsurface imaging with high spatial resolution (~2.0-10.0 µm) in three dimensions and high sensitivity (>110 dB) in vivo with no contact needed between the probe and the tissue.

In biological and biomedical imaging applications, OCT allows for micrometer-scale imaging non-invasively in transparent, translucent, and/or highly-scattering biological tissues. The longitudinal ranging capability of OCT is generally based on low-coherence interferometry, in which light from a broadband source is split between illuminating the sample of interest and a reference path. The interference pattern of light reflected or backscattered from the sample and light from the reference delay contains information about the location and scattering amplitude of the scatterers in the sample. In time-domain OCT (TDOCT), this information is typically extracted by scanning the reference path delay and detecting the resulting interferogram pattern as a function of that delay. The envelope of the interferogram pattern thus detected represents a map of the reflectivity of the sample versus depth, generally called an A-scan, with depth resolution given by the coherence length of the source. In OCT systems, multiple A-scans are typically acquired while the sample beam is scanned laterally across the tissue surface, building up a two-dimensional map of reflectivity versus depth and lateral extent typically called a B-scan. The lateral resolution of the B-scan is approximated by the confocal resolving power of the sample arm optical system, which is usually given by the size of the focused optical spot in the tissue.

The time-domain approach used in conventional OCT, including commercial instruments, such as Carl Zeiss Meditec's Stratus® and Visante® products, has been successful in supporting biological and medical applications, and numerous in vivo human clinical trials of OCT reported to date have utilized this approach.

An alternate approach to data collection in OCT has been shown to have significant advantages in increased signal-to-noise ratio (SNR). This approach involves acquiring the interferometric signal generated by mixing sample light with reference light at a fixed group delay as a function of optical wavenumber. Two distinct methods have been developed which use this Fourier domain OCT (FD-OCT) approach. The first, generally termed Spectral-domain or spectrometer-based OCT (SDOCT), uses a broadband light source and achieves spectral discrimination with a dispersive spectrometer in the detector arm. The second, generally termed swept-source OCT (SSOCT) or optical frequency-domain imaging (OFDI), time-encodes wavenumber by rapidly tuning a narrowband source through a broad optical bandwidth. Both of these techniques may allow for a dramatic improvement in SNR of up to 15.0-20.0 dB over time-domain OCT, because they typically capture the A-scan data in parallel. This is in contrast to previous-generation time-domain OCT, where destructive interference is typically used to isolate the interferometric signal from only one depth at a time as the reference delay is scanned.

FDOCT systems are discussed below with respect to FIGS. 1 through 3. Referring first to FIG. 1, a block diagram illustrating a Fourier domain OCT system in accordance with some embodiments of the present inventive concept will be discussed. As illustrated in FIG. 1, the system includes a broadband source 100, a reference arm 110 and a sample arm 140 coupled to each other by a beamsplitter 120. The beamsplitter 120 may be, for example, a fiber optic coupler or a bulk or micro-optic coupler without departing from the scope of the present inventive concept. The beamsplitter 120 may provide from about a 50/50 to about a 90/10 split ratio. As further illustrated in FIG. 1, the beamsplitter 120 is also coupled to a wavelength or frequency sampled detection module 130 over a detection path 106 that may be provided by an optical fiber.

As further illustrated in FIG. 1, the source 100 is coupled to the beamsplitter 120 by a source path 105. The source 100 may be, for example, a SLED or tunable source. The reference arm 110 is coupled to the beamsplitter over a reference arm path 107. Similarly, the sample arm 140 is coupled to the beamsplitter 120 over the sample arm path 108. The source path 105, the reference arm path 107 and the sample arm path 108 may all be provided by optical fiber.

As further illustrated in FIG. 1, the sample arm 140 may include scanning delivery optics and focal optics 160. Also illustrated in FIG. 1 is the reference plane 150 and a representation of an OCT imaging window 170.

Referring now to FIG. 2, a block diagram of an FDOCT retinal imaging system will be discussed. As illustrated in FIG. 2, in an FDOCT retinal imaging system, the reference arm 110 may further include a collimator assembly 280, a variable attenuator 281 that can be neutral density or variable aperture, a mirror assembly 282, a reference arm variable path length adjustment 283 and a path length matching position 250, i.e. optical path length reference to sample. As further illustrated, the sample arm 240 may include a dual-axis scanner assembly 290 and a variable focus objective lens 291.

The sample in FIG. 2 is an eye including a cornea 295, iris/pupil 294, ocular lens 293 and retina 296. A representation of an OCT imaging window 270 is illustrated near the retina 296. The retinal imaging system relies in the optics of the subject eye, notably cornea 295 and ocular lens 293, to image the posterior structures of the eye.

Referring now to FIG. 3A, a block diagram illustrating a FDOCT cornea imaging system will be discussed. As illustrated therein, the system of FIG. 3A is very similar to the system of FIG. 2. However, the objective lens variable focus need not be included, and is not included in FIG. 3A. The anterior imaging system of FIG. 3A images the anterior structures directly, without reliance on the optics of the subject to focus on the anterior structures.

As illustrated by FIGS. 3A through 3C, the OCT imaging window 370 can be moved to image various portions of the sample.

In both spectrometer-based and swept-source implementations of FDOCT, light returning from all depths is generally collected simultaneously, and is manifested as modulations in the detected spectrum. Transformation of the detected spectrum from wavelength to wavenumber (or frequency), correction for dispersion mismatches between the sample and reference arms, and Fast Fourier transformation typically provides the spatial domain signal or "A-scan" representing depth-resolved reflectivity of the sample. The uncorrected A-scan may also include a strong DC component at zero pathlength offset, so-called "autocorrelation" artifacts resulting from mutual interference between internal sample reflections, as well as both positive and negative frequency components of the depth-dependent cosine frequency interference terms. Because of this, FDOCT systems typically exhibit a "complex conjugate artifact" due to the fact that the Fourier transform of a real signal, the detected spectral interferogram, is typically Hermitian symmetric, i.e., positive and negative spatial frequencies are not independent. As a consequence, sample reflections at a positive displacement, relative to the reference delay, typically cannot be distinguished from reflections at the same negative displacement, and appear as upside-down, overlapping images on top of genuine sample structure, which generally cannot be removed by image processing.

The maximum single-sided imaging depth available in SDOCT is governed by the spectral sampling interval. The maximum single-sided imaging depth is inversely proportional to the spectral sampling interval. With a fixed number of sampled spectral elements, there is an inverse relationship between the maximum imaging depth and the minimum axial resolution of the imaging system. In commercial FDOCT systems at 830 nm and 1300 nm reported to date, the single-sided imaging depth has been limited to approximately 4 mm. Time domain imaging has been used for greater imaging depths.

The finite spectral resolution of any real FDOCT system, whether governed by the linewidth of a swept laser source in SSOCT, or the geometric optical performance of the spectrometer convolved with the finite pixel size of the detector array in SDOCT, gives rise to a sensitivity "falloff" with imaging depth into the sample. It is common to have greater than 6 dB degradation in signal-to-noise from the position of zero reference delay to the position of maximum single-sided depth. This sensitivity "falloff" limits the portion of the single-sided depth useful for imaging.

To reduce the impact of these limitations in FDOCT imaging, imaging is commonly performed with the entire sample either above or below the reference position, limiting the available imaging depth to between 2 mm and 4 mm, and placing the sample region of interest close to the zero reference delay position.

Each of these constraints poses limitations on the application of FDOCT to clinical ophthalmology. Imaging systems have generally been dedicated to imaging of specific anatomy, such as retina or cornea, where the mirror image artifacts do not fold over onto images of the region of interest. Utility to image deeper anatomic structures, such as the choroid, has been limited by sensitivity "falloff".

Addressing these limitations opens significant new application areas for FDOCT, particularly in ophthalmology. Full range volumetric anterior segment imaging (cornea to lens) for improved diagnosis of narrow angle glaucoma is enabled at speeds 20 times greater and resolutions four times finer than time domain implementations. Real-time image guided surgery, for anterior chamber, cataract, or retina, is enabled by allowing placement of a deep imaging window at any position within the sample, without concern for confounding mirror image artifacts or signal "falloff," Images of the entire eye may be acquired, enabling for the first time modeling in three dimensions the entire optical structure of the eye and enabling whole-eye biometry.

SUMMARY

Some embodiments discussed herein provide an optical coherence tomography system for imaging a whole eye, the system includes a sample arm including focal optics that are configured to rapidly switch between at least two scanning modes in less than about 1.0 second.

In further embodiments, the focal optics may be configured to be switched between the at least two modes without use of an external adapter.

In still further embodiments, the at least two modes may include an anterior segment scanning mode and a retinal scanning mode. The system may further include a mechanical means configured to rapidly insert at least one additional lens into and/or remove the at least one additional lens from an optical path of the sample arm to switch the system between the anterior segment scanning mode and the retinal scanning mode.

In some embodiments, the sample arm of the system in retinal scanning mode may include a collimator, a two-dimensional galvanometer scanner, and a single scan lens in a telecentric configuration. The mechanical means may be configured to rapidly insert a single additional lens into the optical path immediately proximal or immediately distal to the collimating lens to change the system from the retinal scanning mode to anterior segment scanning mode.

In further embodiments, the additional lens in the optical path may be configured to change a sample arm beam from collimated to focusing on the two-dimensional galvanometer scanner.

In still further embodiments, the mechanical means includes at least one lens mounted to a mechanical plate that is configured to be rotated into and out of the optical path. The system may further include a controller configured to cause the mechanical means to rapidly rotate the plate.

In some embodiments, the mechanical means may include a rotary solenoid attached to an arm including the additional lens, the rotary solenoid may be configured to rapidly rotate the additional lens into and out of the optical path.

In further embodiments, the at least two modes may include an anterior segment scanning mode and a retinal scanning mode. The sample arm of the system in the retinal scanning mode may include a collimating lens, a two-dimensional galvanometer scanner pair, a scan lens and an objective lens. The sample arm of the system in the anterior segment scanning mode may include a collimating lens, two two-dimensional galvanometer scanner pairs, a scan lens, an objective lens and a curved mirror placed a focal length f away from a first of the two two-dimensional galvanometer scanner pairs, wherein the a second of the two two-dimensional galvanometer scanner pairs directs re-directed collimated light in a triangular pattern towards the curved mirror causing an optical path length of the system to be longer in the anterior segment scanning mode as compared to the retinal scanning mode.

In still further embodiments, the at least two modes may include an anterior segment scanning mode and a retinal scanning mode. The sample arm of the system in the retinal scanning mode may include a collimating lens, a two-dimensional galvanometer scanner pair, a scan lens and an objective lens. The sample arm of the system in the anterior segment scanning mode may include a collimating lens, a two-dimensional galvanometer scanner pair, a scan lens, an objective lens, a flat mirror and a concave mirror placed a focal length f away from the two-dimensional galvanometer scanner pairs, wherein light incident on the two-dimensional scanner pair is deviated such that the an incident collimated beam is directed into a separate path consisting of the flat mirror and the concave mirror.

In some embodiments, the system may further include a reference arm including a means for rapidly switching a reference delay when the focal optics of the sample arm are switched between the at least two scanning modes. The reference arm may further include a coupler configured to split light from the reference arm of the interferometer into at least two separate paths. The at least two separate paths may be preset to an optical delay each corresponding to one of the at least two scanning modes.

In further embodiments, the means for rapidly switching a reference delay may include a rapid mechanical switch configured to block all but a desired reference delay associated with a corresponding one of the at least two scanning modes.

In still further embodiments, the at least two scanning modes may include and iris pivot scanning mode and a telecentric scanning mode. The sample arm may include a telecentric scanning lens and first and second objective lenses, wherein the first and second objective lenses are a first distance apart in a first position when the system is operating in telecentric scanning mode and a second distance apart in a second position when the system is operating in the iris pivot scanning mode.

In some embodiments, the first and second objective lenses may be configured to slide between the first and second positions to switch between scanning modes.

In further embodiments, the at least two scanning modes may include a telecentric scanning mode and a collimated scanning mode. The sample arm may include a fiber input, a collimating lens, a scanning mirror, a telecentric scanning lens, and a telecentric scanning beam. The collimating lens may be in a first position in telecentric scanning mode and a second position in collimated scanning mode. The collimating lens may be translated by a distance equal to a focal length of the collimating lens in the second position to provide the collimated scanning mode.

In still further embodiments, the at least two scanning modes may include a telecentric scanning mode and a collimated scanning mode. The sample arm may include a fiber input, a collimating lens, a scanning mirror, a telecentric scanning lens, and a telecentric scanning beam in the telecentric scanning mode. The sample arm may further include a secondary lens behind the collimating lens in collimated scanning mode.

Some embodiments of the present invention provide optical coherence tomography systems for imaging a whole eye, the system comprising a reference arm configured to adapt to focal optics of at least two scanning modes of the system.

In further embodiments, the reference arm may include a mechanical means configured to discretely switch reference arms such that the reference arm is matched a corresponding one of the at least two scanning modes.

In still further embodiments, the reference arm may be configured to rapidly switch between reference delays, each of the reference delays corresponding to one of the at least two scanning modes.

Some embodiments provide methods for imaging a whole eye in an optical coherence tomography system, the methods including rapidly switching focal optics of a sample arm between at least two scanning modes in less than about 1.0 second.

In further embodiments, switching the focal optics of the sample arm may include switching the focal optics of the sample arm between the at least two scanning modes without use of an external adapter.

In still further embodiments, the at least two modes may include an anterior segment scanning mode and a retinal scanning mode.

In some embodiments, the method may further include rapidly switching a reference delay when the focal optics of the sample arm are switched between the at least two scanning modes.

BRIEF DESCRIPTION OF THE FIGURES

FIGS. 4A and 4B are graphs illustrating the spatial and spectral domain, respectively, that illustrate conceptually the effects that various parameters of the light source and spectral detection system in accordance with some embodiments.

FIGS. 5A through 5E OCT systems and images acquired using these OCT ophthalmic imaging systems in accordance with some embodiments.

FIG. 17 is a table including various details with respect to SDOCT systems in accordance with various embodiments of the present inventive concept.

FIGS. 28A and 28B illustrate switchable anterior-retinal scanning systems in accordance with some embodiments.

FIGS. 30A and 30B illustrate switchable anterior-retinal scanning systems in accordance with some embodiments.

FIG. 37 is a diagram illustrating an optical layout for collimated mode in accordance with some embodiments.

FIG. 38 is a diagram illustrating an optical layout for collimated mode in accordance with some embodiments.

FIG. 42 is a block diagram illustrating a mechanical means for rapidly switching scanning modes in accordance with some embodiments of the inventive concept.

DETAILED DESCRIPTION OF EMBODIMENTS

Figure 1:
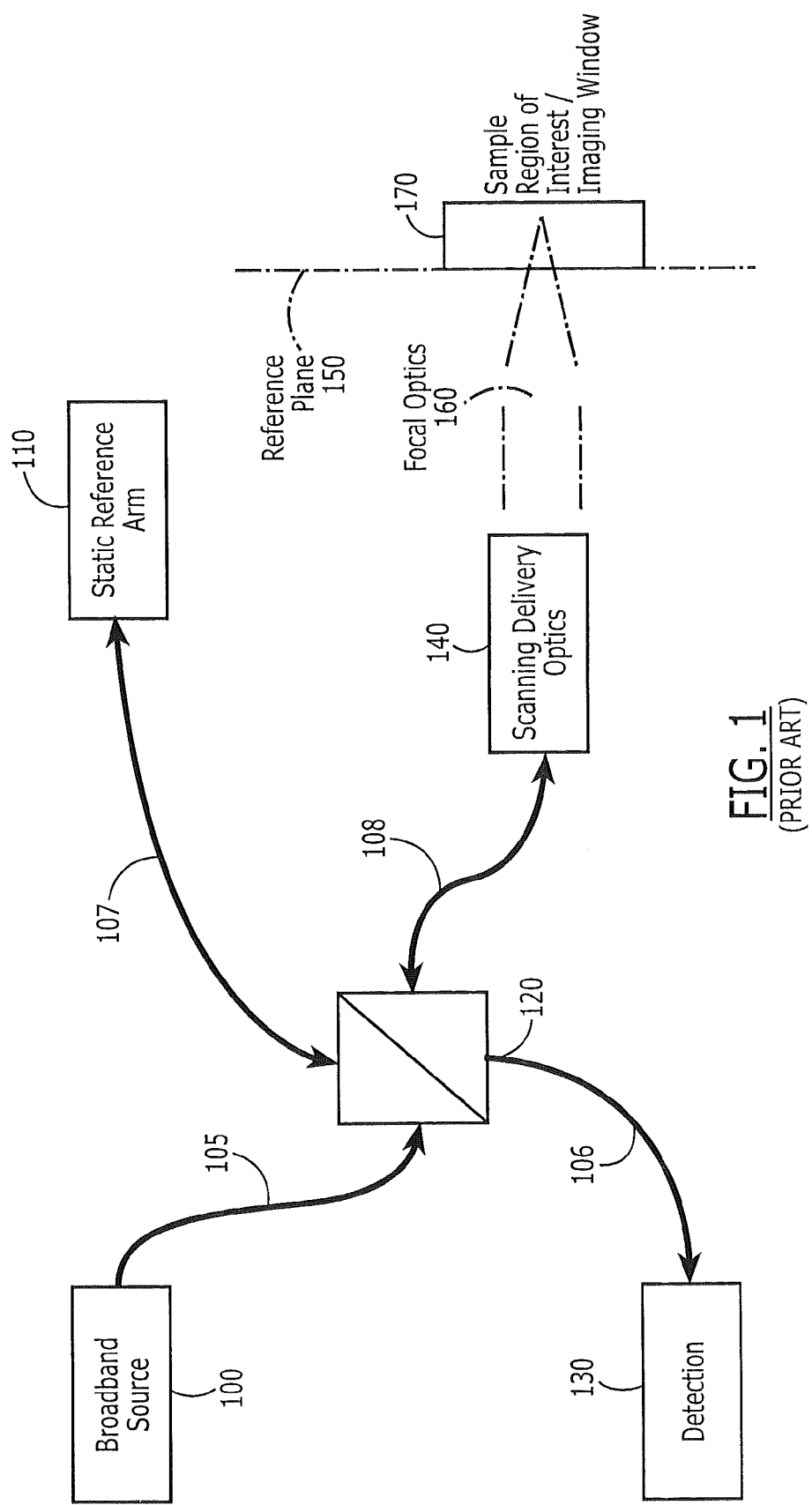
FIG. 1 is a block diagram illustrating a Fourier domain optical coherence tomography (OCT) imaging system.

Specific exemplary embodiments of the inventive concept now will be described with reference to the accompanying drawings. This inventive concept may, however, be embodied in many different forms and should not be construed as limited to the embodiments set forth herein; rather, these embodiments are provided so that this disclosure will be thorough and complete, and will fully convey the scope of the inventive concept to those skilled in the art. The terminology used in the detailed description of the particular exemplary embodiments illustrated in the accompanying drawings is not intended to be limiting of the inventive concept. In the drawings, like numbers refer to like elements.

As used herein, the singular forms "a", "an" and "the" are intended to include the plural forms as well, unless expressly stated otherwise. It will be further understood that the terms "includes," "comprises," "including" and/or "comprising," when used in this specification, specify the presence of stated features, integers, steps, operations, elements, and/or components, but do not preclude the presence or addition of one or more other features, integers, steps, operations, elements, components, and/or groups thereof. It will be understood that when an element is referred to as being "connected" or "coupled" to another element, it can be directly connected or coupled to the other element or intervening elements may be present. Furthermore, "connected" or "coupled" as used herein may include wirelessly connected or coupled. As used herein, the term "and/or" includes any and all combinations of one or more of the associated listed items.

Unless otherwise defined, all terms (including technical and scientific terms) used herein have the same meaning as commonly understood by one of ordinary skill in the art to which this inventive concept belongs. It will be further understood that terms, such as those defined in commonly used dictionaries, should be interpreted as having a meaning that is consistent with their meaning in the context of the relevant art and this specification and will not be interpreted in an idealized or overly formal sense unless expressly so defined herein.

Embodiments discussed herein with respect to FIGS. 1 through 26 may be used in combination with many imaging systems for many applications and is not limited to the specific systems or applications discussed herein. For example, imaging systems discussed in commonly assigned U.S. Pat. Nos. 7,602,500; 7,742,174; and 7,719,692 and U.S. Patent Application Publications Nos. 2008/01606696 and 2008/0181477 may be used in combination with embodiments discussed herein. The disclosures of these patents and publications are hereby incorporated herein by reference as if set forth in its entirety.

As used herein, the term "spectral element" refers to the individually resolved samples of the interferometric spectrum as they are detected in an FDOCT system, the detected set of which forms the input to the Fourier transform operation; a spectral element is characterized by a finite wavelength range that is generally a continuous small fraction of the total bandwidth, an optical power, and a power spectral density (lineshape).

The first successful clinical application of OCT was for high-resolution imaging of ocular structure. OCT is well suited to ophthalmology because it is non-contact, easily adaptable to existing ophthalmic instrumentation, and most importantly, the axial imaging resolution is independent of the working distance. In the anterior eye, the micron-scale resolution of OCT imaging permits accurate biometry of large scale ocular structures and the evaluation of morphological changes associated with pathologies of the cornea, iris, and lens. In the retina, OCT is the only technique capable of resolving retinal substructure in cross section in the living eye. Imaging of retinal substructure is clinically relevant to the diagnosis and management of many ocular diseases. In many clinical trials of OCT, striking images have been obtained of a variety of retinal abnormalities, including macular defects and retinal nerve fiber atrophy. Retinal OCT has become well accepted as a clinical adjunct to conventional macular photography, as well as a very popular research tool.

As is well known in the art, Fourier domain optical coherence tomography (FDOCT) has become the standard of care in clinical ophthalmology for imaging of the retina. The theory and practice of FDOCT is well known and documented.

Several academic research groups have published detailed treatments of the dramatic 20-30 dB signal-to-noise predicted and actual performance improvement in FDOCT as compared to its time-domain counterparts. Despite this tremendous improvement, there are performance limitations in FDOCT which do not have analogs in previous time-domain systems. In both spectrometer-based (SDOCT) and swept-source (SSOCT) implementations of FDOCT, the wavenumber (k) resolved receiver current can be represented by equation (1) set out below:

$$i(k) = \frac{1}{2}\rho S(k)[R_R + R_S + 2\sqrt{R_R R_S} \cos(2kz_0 + \phi)] \quad (1)$$

where $\rho$ is the receiver element responsivity, $S(k)$ is the light source spectrum, $R_R$ and $R_S$ are the received power from the reference and sample arms, respectively, $z_0$ is the pathlength difference between the reference delay and a target reflection in the sample ($2z_o$ is the round-trip pathlength difference), and $\phi$ is the phase offset of the interferometer at zero pathlength optical delay. As in time domain OCT, the axial imaging resolution $\Delta z$ is defined by the source center wavelength $\lambda_0$ and FWHM bandwidth $\Delta \lambda$ as shown in equation (2) set out below:

$$\Delta z = \frac{2\ln(2)}{\pi} \frac{\lambda_0^2}{\Delta \lambda} \quad (2)$$

In FDOCT, light returning from all depths is collected simultaneously, and is manifested as modulations in the detected spectrum. Transformation of the detected spectrum from wavelength to wavenumber, correction for dispersion mismatches between the sample and reference arms, and Fast Fourier transformation provides the spatial domain signal or "A-scan" representing depth-resolved reflectivity of the sample.

FIGS. 4A and 4B illustrate conceptually the effects that various parameters of the light source and spectral detection system have on the transformed OCT signal. In both SDOCT and SSOCT systems, the detected spectral signal is composed of a DC term and cosinusoidal terms with depth-dependent frequency. This signal is enveloped by the source spectrum and convolved with the spectral resolution ($\delta_r k$) of the FDOCT system. In SSOCT, the spectral resolution $\delta_r k$ is limited by the instantaneous lineshape of the swept laser source, while in SDOCT, $\delta_r k$ is the spectral resolution of the spectrometer (which in turn may be described as a convolution of the geometric optic spectrometer resolution with the detector array pixel dimensions). The detected spectrum is sampled with spectral sampling interval $\delta_s k$ into N spectral channels, each of these channels comprising a unique spectral element. The Fourier transform of the detected spectral signal, i.e. the set of spectral elements, includes a strong DC component at zero pathlength offset, as well as both positive and negative frequency components of the depth-dependent cosine frequency terms located at positions $\pm 2x_0$. The shape of each peak is defined by the coherence function of the source, given by the inverse Fourier transform of its total detected power spectral density; as in time-domain OCT, the axial imaging resolution is inversely proportional to the total detected spectral bandwidth of the light source.

Figure 5D:
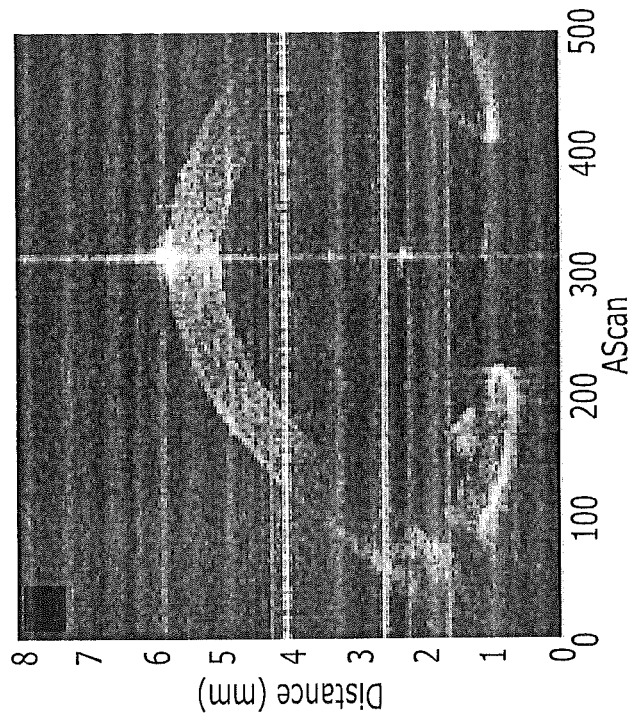
Figure 5C:
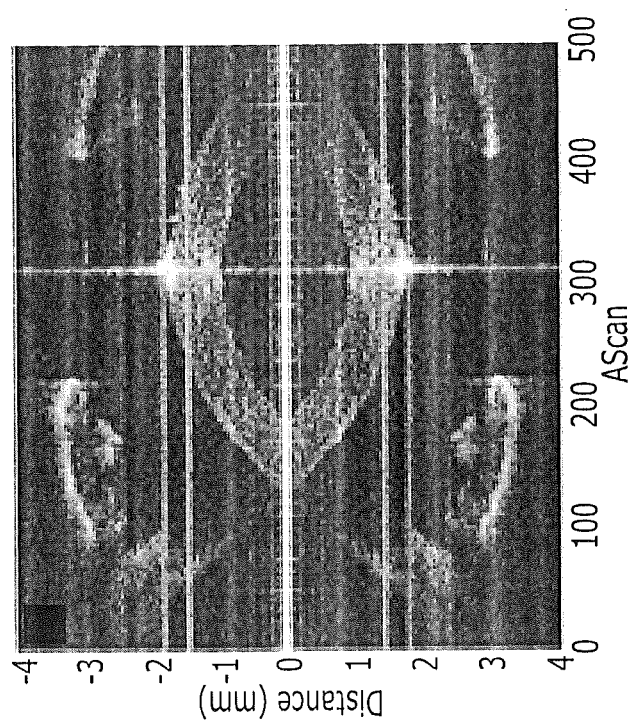
Figure 5E:
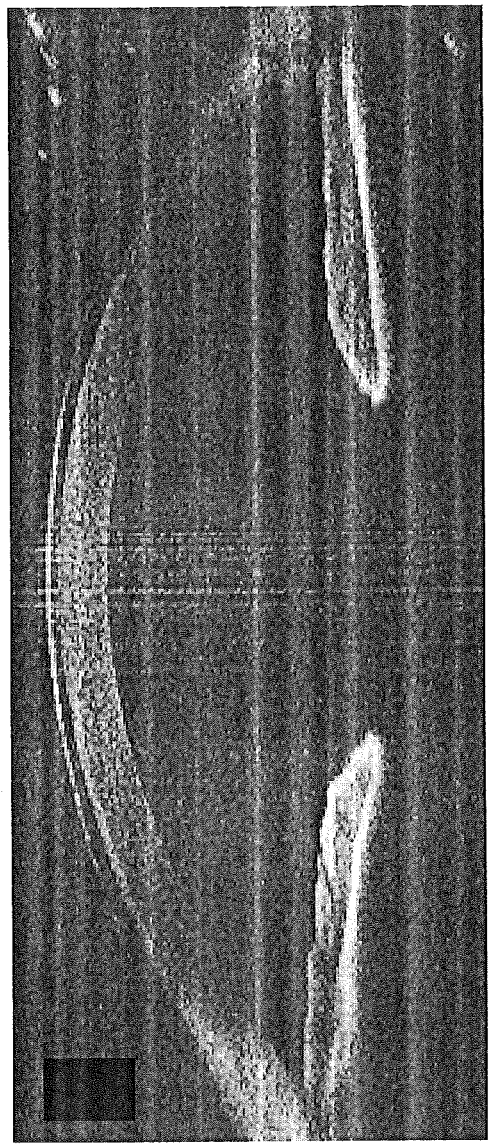

There are at least three important limitations which are novel in FDOCT: complex conjugate artifact, maximum imaging depth, and sensitivity falloff. The presence in the spatial-domain A-scan data of both positive and negative frequency components of the spectral interferometric signal gives rise to the so-called "complex conjugate artifact" which typically requires careful sample positioning to assure that overlapping negative frequency components do not interfere with the principal positive-frequency image as illustrated in FIG. 5C. Methods to reduce this "complex conjugate artifact" are now known in the art. In particular, FIG. 5A illustrates a 3×3 SDOCT system utilizing two spectrometers; FIG. 5B illustrates a 3×3 SSOCT system implementing DC signal subtraction with balanced photodiode detectors D1 and D2; FIGS. 5C and 5D illustrate unprocessed and complex conjugate resolved images of human anterior segment acquired in vivo with 3×3 SSOCT, using a first image processing processing method; and FIG. 5E illustrates improved complex conjugate artifact removal (better than 30 dB) obtained using a quadrature projection algorithm.

Figure 6:
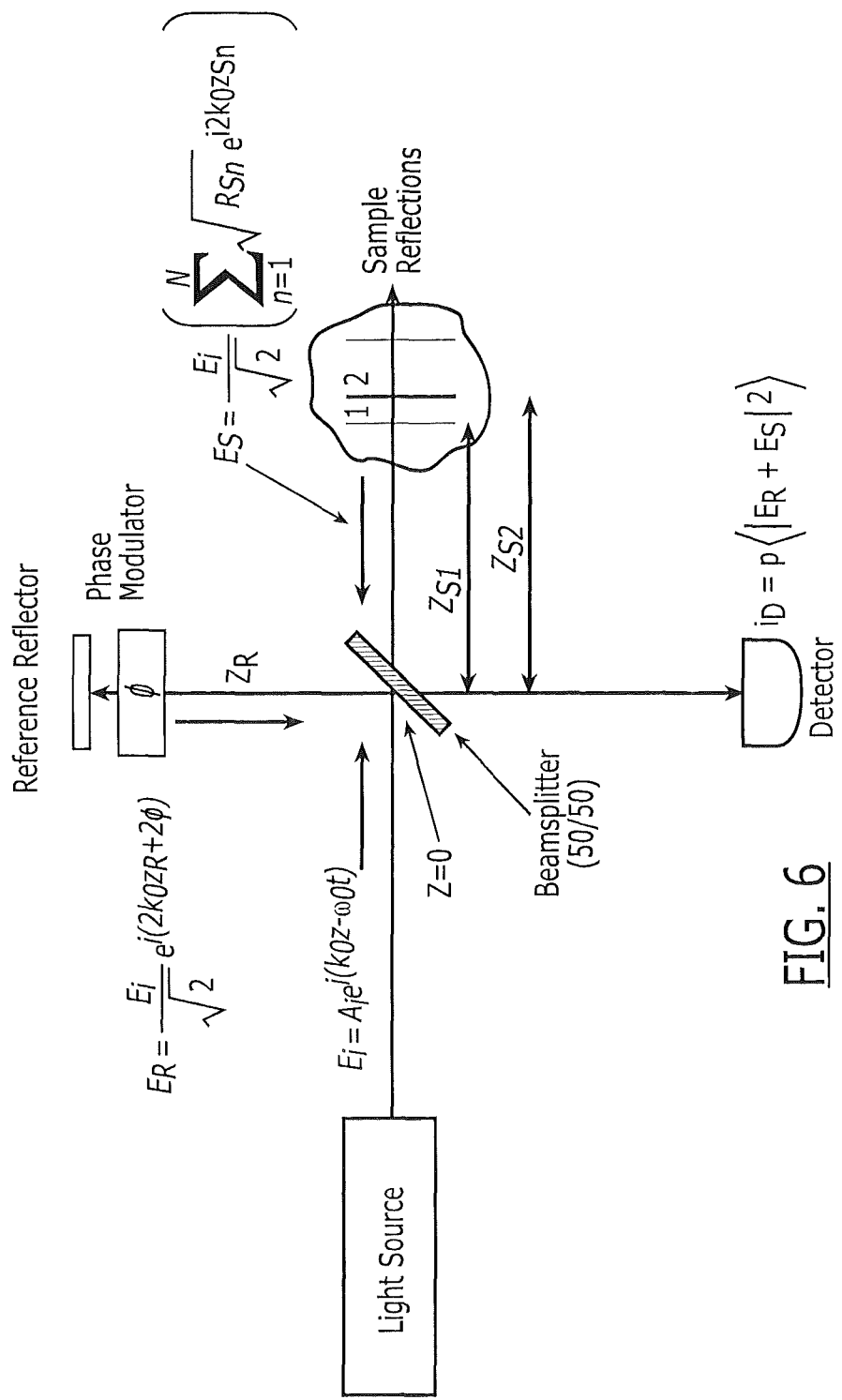
FIG. 6 is a block diagram illustrating an FDOCT interferometer having a variable round trip phase delay in the reference arm in accordance with some embodiments.

The complex conjugate artifact in FDOCT may also be removed by utilizing principles and techniques related to phase-shift interferometry. If the interferometer is modified to provide for the introduction of a variable single-pass phase delay $\phi$ (round-trip phase delay $2\phi$) between the reference and sample arms, then a set of spectral interferograms may be acquired with different phase delays which can be combined in signal processing to eliminate the undesired artifacts. For example, FIG. 6 illustrates an FDOCT interferometer with a variable phase modulator placed in the reference arm, such that the reference field returning from the reference arm is modified.

Various technical solutions to this complex conjugate artifact problem have been proposed by several groups, however all of those proposed to date require rather complicated schemes for acquisition of multiple interferometric spectra, and none have yet proven satisfactory for high duty cycle imaging. For ophthalmic imaging, the complex conjugate artifact necessitates maintaining very careful positioning of the patient to avoid overlapping upside-down images (difficult in some patients), and it precludes imaging tissues any thicker than the single-sided imaging depth $z_{max}$ defined next.

Due to spectral sampling considerations, the maximum single-sided imaging depth $z_{max}$ available in FDOCT is governed by the spectral sampling interval $\delta_s k$ or $\delta_s \lambda$, according to equation (3) set out below:

$$z_{max} = \frac{\pi}{2 \cdot \delta_s k} = \frac{\lambda_0^2}{4 \cdot \delta_s k} \quad (3)$$

These expressions are given in terms of both wavenumber $k$ ($=2\pi/\lambda$) and wavelength $\lambda$ (with center wavelength $\lambda_0$). In FDOCT systems at 830 nm and 1300 nm reported to date, $z_{max}$ has been limited to approximately 4.0 mm.

The finite spectral resolution of any real FDOCT system, whether governed by the linewidth of a swept laser source in SSOCT, or the geometric optical performance of the spectrometer convolved with the finite pixel size of the detector array in SDOCT, gives rise to a falloff in sensitivity with imaging depth that is independent of light attenuation within the sample. More generally for both SDOCT and SSOCT systems, if an "effective" detector sampling resolution $\delta_r k$ or $\delta_r \lambda$ is defined which accounts for all effects limiting the spectral resolution of the sampled elements, a simpler expression can be derived for the falloff to the 6 dB SNR point as illustrated by equation (4) set out below:

$$z_{6dB} = \frac{2\ln(2)}{\delta_r k} = \frac{\ln(2)}{\pi} \frac{\lambda_0^2}{\delta_r k} \tag{4}$$

In typical FDOCT systems, the falloff phenomenon exacerbates the already-limited imaging depth $z_{max}$. In SSOCT systems, the spectral linewidth is a function of laser dynamics and the detector sampling architecture. In SDOCT systems, the spectral sampling interval $\delta_s k$ and spectral linewidth $\delta_r k$ are generally a function of spectrometer design. In a well-designed spectrometer with Nyquist sampling of the optics-limited resolution, $\delta_r k \geq 2\delta_s k$. For the case of $\delta_r k = 2\delta_s k$, equations (3) and (4) can be combined to obtain the useful rule of thumb for SDOCT systems illustrated by equation (5) set out below:

$$\frac{z_{6dB}}{z_{max}} \approx 0.44 \tag{5}$$

Thus, in practical SDOCT systems, as in most commercial ophthalmic SDOCT systems, the useful portion of the depth imaging range, defined as the 6 dB falloff point, is limited to approximately half of the range given by the spectral sampling, i.e. approximately 2.0 mm instead of 4.0 mm. This may be sufficient for imaging the normal retina, however it may preclude imaging structures above and below normal retina, for example, vitreous features, choroid, and deeply cupped optic nerve heads. It may also be insufficient for imaging almost any anterior segment structures besides the cornea without incurring upside-down artifacts.

The complex conjugate artifacts and falloff of sensitivity with imaging depth are fundamentally new limitations in FDOCT, which have not yet been successfully addressed by technical innovation. These phenomena represent significant limitations to the applicability of FDOCT techniques for ophthalmic diagnostics which require imaging of structures deeper than about 2.0 mm.

Figure 15:
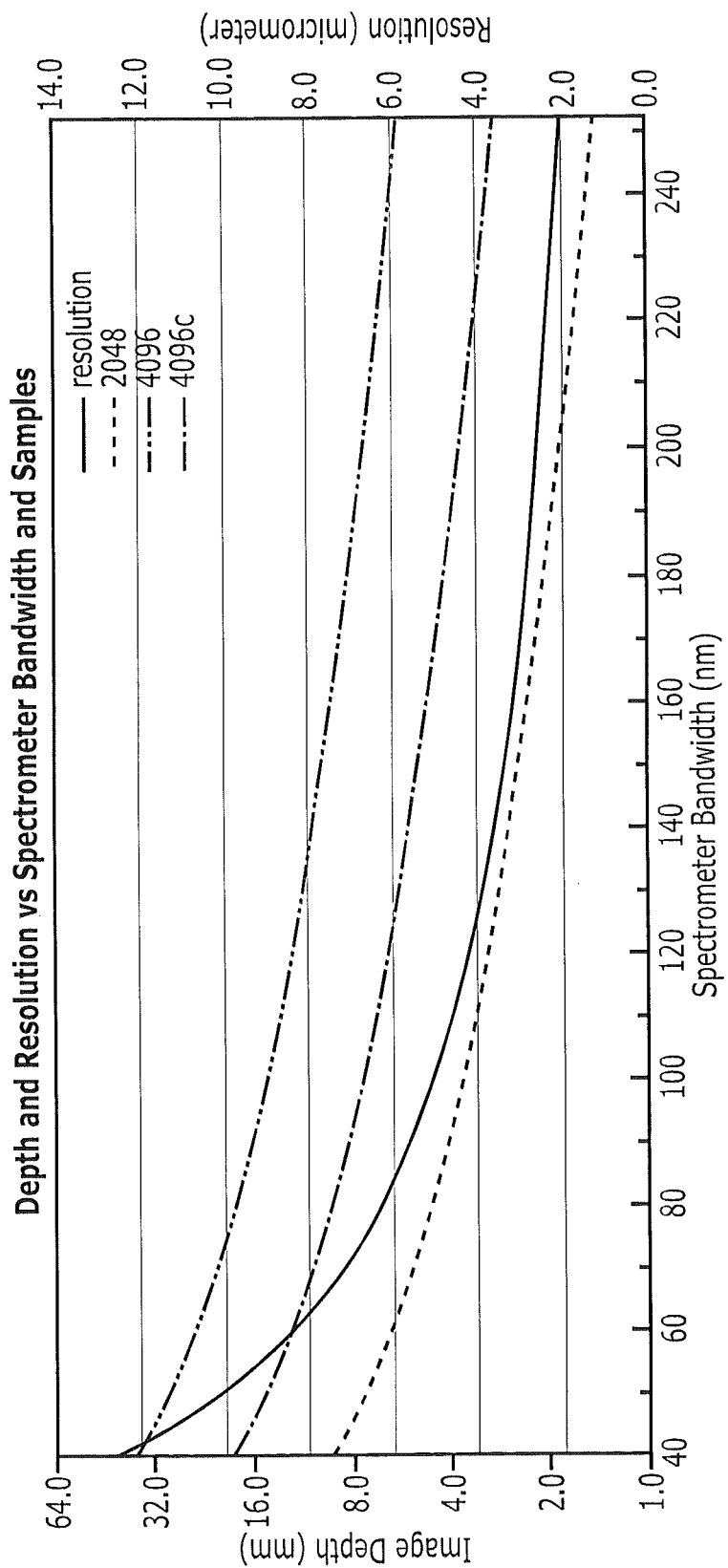
FIG. 15 is a graph illustrating depth and resolution vs. spectrometer bandwidth and samples for an extended depth FDOCT system in accordance with some embodiments discussed herein.

Three improvements may be combined for overcoming the limitations discussed above and enabling deep imaging FDOCT systems for new applications of FDOCT where increased depth and removal of mirror-image artifacts are desirable. Deep-imaging sampling architectures increase $z_{max}$. Modifying the sampled spectral bandwidth such that the bandwidth of the sampled element is less than the sampling interval reduces the deleterious effects of sensitivity falloff. Addition of phase information to the acquired spectrum provides information sufficient to remove complex conjugate artifacts. The combination of the latter two techniques enables system design to quadruple available imaging depth without impacting the axial resolution of the imaging system. Tailoring the sampling architecture to adjust the maximum imaging depth zmax requires a trade-off between axial resolution and maximum imaging depth, as shown in FIG. 15, as may be appropriate for the imaging of target structures. These techniques may be applied to either SDOCT or SSOCT implementations, and to implementations that combine elements of SDOCT and SSOCT. Further, in some cases these techniques may be applied dynamically, controlling $z_{max}$, complex-conjugate management, and falloff in situ to manage trade-offs in pixel resolution, region of subject focus, optical power on subject, and imaging speed as may be appropriate for specific objectives during the imaging process.

For a traditional volume phase holographic (VPH) grating based spectrometer design, the imaging depth, as measure in tissue of refractive index n, is related to the bandwidth and pixel count of the spectrometer as illustrated in equation (6) set out below:

$$z_{max} = \lambda_c^2 / 4n\lambda_s \tag{6}$$

Where
$\delta$=spectrometer bandwidth (nm)=
$\lambda_c$=source center wavelength (nm)
p=pixels (detector channels)
$\lambda_s$=spectrometer wavelength spacing=$\delta/p$
n=index of refraction A key spectrometer design decision is to optimize for image resolution, by maximizing available bandwidth $\delta$, or optimize for imaging depth, by minimize sampling interval $\lambda_s$.

With $\lambda_s = \delta/p$ equation (6) becomes:

$$z_{max} = p\lambda_c^2 / 4n\delta \tag{7}$$

For fixed p, solving for $\delta$ in becomes:

$$\delta = p\lambda_c^2 / 4n z_{max} \tag{8}$$

Alternatively, for fixed $\delta$ and solving for $\lambda_c$ in nanometers leads to:

$$\lambda_c = \sqrt{(4n\delta z_{max}/p)} \tag{9}$$

The determination of the optimum values for $\lambda_c$ and $\delta$ are based upon the requirements for the application, for example, wavelength and imaging depth.

Further definition of the design parameters can be obtained by relating the image size to the detector pixel size in order to determine the spectrometer focal length required. Assuming a collimated beam input to the grating the diffraction limited spot size can be represented by the following expression set out in equation 10:

$$D = 1.22\lambda_c(f/d) \tag{10}$$

Where f is the focal length of the spectrometer imaging optics and d is typically the lens aperture diameter which in this case is equivalent to the spectrometer input collimated beam diameter. Solving for (f/d), $$(f/d) = D/1.22\lambda_c \tag{11}$$

Therefore, given an exemplary pixel size of 10 um and setting the target diffraction limited image spot radius to the 75% of detector pixel size yields a spot diameter of 7.5 μm. From equation (11) it can be determined that the ratio of the focal to input beam diameter:

$$(f/d) = 3.5 \tag{12}$$

From expression (10) for a collimated beam of 25 mm in diameter the required focal length of the spectrometer imaging optics is 89 mm. Conversely, setting the focal length to 100 mm requires a 28 mm collimated beam input. The determination of which parameter to solve for is based on other physical design constraints of the spectrometer. Further definition of the spectrometer optical design to achieve a diffraction limited spot across a detector array is known and therefore will not be discussed herein.

Using the grating equation (13):

$$\lambda_c f = \sin\theta_i + \sin\theta_d \quad (13)$$

Where
$\lambda_c$=source center wavelength
f=spatial frequency of the grating
$\theta_i$=angle of incidence
$\theta_d$=angle of diffraction For standard planar transmission VPH grating designs $\theta_i=\theta_d$, Solving for f, equation (13) is reduced to:

$$f = 2\sin\theta/\lambda_c \quad (14)$$

With the practical upper limit established by:

$$f = 2/\lambda_c \quad (15)$$

Since the spectral dispersion of the VPH grating is proportional to the grating spatial frequency, design optimization is directed toward the spatial frequency. The optical design of the spectrometer is important in selecting the grating dispersion value. With a spectrometer detector array of predetermined physical length and a fixed center wavelength and bandwidth, the dispersion is selected to insure full coverage of the spectral bandwidth across the detector array.

By definition, the dispersion of the grating is the rate of change of the angle of diffraction with wavelength for a fixed angle of incidence or $\Delta\theta/\Delta\lambda$, which from a differentiation of equation (14) yields:

$$\Delta\theta/\Delta\lambda = f/\cos\theta \quad (16)$$

The optical design of the spectrometer and grating dispersion are interrelated. For a given array length and focal length of the imaging optics the angle of dispersion can be given as:

$$\phi = 2\tan^{-1}(A/2f) \quad (17)$$

where f is the focal length of the imaging optics and A is the detector array length. From equation (17) the grating dispersion relates the dispersion angle by:

$$\phi = a f \delta/\cos\theta = 2\tan^{-1}(A/2f) \quad (18)$$

where a is the unit conversion from radians/mm to degrees/nm and f is determined by the detector pixel size as stated in equation (12).

Using equation (14) the expression can be reduced as follows $$(a\delta/\lambda_c)\tan\theta = \tan^{-1}(A/2f) \quad (19)$$

Solving for $\theta$:

$$\theta = \tan^{-1}[(\lambda_c/a\delta)\tan^{-1}(A/2f)] \quad (20)$$

From the above equations, the required dispersion angle can be calculated for a given spectrometer layout. The parameters required as inputs to the equations are the detector pixel size which defines the required focal length, (A) the linear dimension of the detector array, ($\lambda_c$) the center wavelength of the source and ($\delta$), the bandwidth of the source. From the calculated dispersion value, the grating frequency and grating angle can be calculated resulting in a complete characterization of the spectrometer design.

Grating-based spectrometer designs as discussed above disperse the light linearly as a function of wavelength across the detector array. In Fourier Transform Spectroscopy and Fourier Domain Optical Coherence Tomography, the signal of interest is the Fourier transform of the detected spectrum. The Fourier transform analog to spatial position is spatial frequency, but the detector captures spatial period and thus requires an additional interpolation step to scale the detected spectrum from spatial period to spatial frequency. This resampling is a time-consuming process, and the elimination of such would enable both faster processing and more accurate sampling in spatial frequency or wavenumber (k) space.

Additionally, resampling is inadequate to the task of providing a constant depth scale in the Fourier transformed spatial image. The chirped sampling (relative to the spatial frequency) yields a chirp in depth per pixel across the image depth. As the imaging window becomes deeper, this chirp is more deleterious to dispersion compensation and to quantitative measurements across the image depth. It is therefore desirable to design an FDOCT system sampled linearly in frequency (k, wavenumber).

As indicated, the maximum depth of the SDOCT system is defined by the spatial sampling of the spectrum at the detector—increased wavelength (or wavenumber) sample density allows for sampling of higher frequency fringes on the spectrum and thus returns signals from deeper depths. This relationship is related by:

$$Z_{max} = \frac{1}{4 * \delta v_s} \quad (21)$$

Where $\delta v_s$ is the wavenumber sampling at the detector. Wavelength and wavenumber are related by:

$$\frac{\Delta v}{v} = \frac{\Delta\lambda}{\lambda} \quad (22)$$

Equi-sampling in wavenumber will reduce the burden on computational resampling, and improve the linearity of the depth scaling in the final image. Additionally, application of wavenumber or k-linearization is well suited to channelized imaging, for example through the use of a comb filter for SDOCT and SSOCT, or through the use of controlled duty-cycle sampling in SSOCT, as discussed below.

Design of k-linearized spectrometers using a prism airspaced with respect to a grating has been reviewed elsewhere, for example, in Fourier Domain optical coherence tomography with a linear-in-wavenumber spectrometer by Hu et al. However, the use of a prism-air space-grating configuration requires control of extra degrees of freedom, and adds to the number of glass-air interfaces, potentially reducing manufacturability and increasing costs. As originally described in Constant-dispersion grism spectrometer for channeled spectra by Traub, a prism-grating (GRISM) structure in intimate contact may be adequate to the task of creating, in the language of Traub, a constant dispersion (k-linear) spectrograph. Traub, however, does not provide a prescription for practical design of a grism spectrometer that meets the requirements of FDOCT imaging, including the relationship between required dispersion and degree of linearization required. As shown below, with proper specification of grating spatial frequency, prism index and chromatic dispersion, prism angle, and input angle, a k-linear spectrometer can be designed with sufficient linearity to support a frequency-channelized implementation with improved sensitivity falloff characteristics.

The exit angle, $\beta$, of an isosceles prism is related to the entrance angle, $\alpha$, the vertex angle, $\epsilon$, and the index of refraction of the prism as a function of wavelength, $n_p(\lambda)$. Using Snell's law and assuming the medium surrounding the prism is air, the angle of the light after refracting at the first surface of the prism, $\theta_1$, is:

$$\theta_1 = \sin^{-1}\left(\frac{1}{n_p(\lambda)}\sin\left(\alpha - \frac{\varepsilon}{2}\right)\right) \quad (23)$$

Following the same logic, the angle after refraction at the second surface of the prism, $\theta_2$, is:

$$\theta_2 = \sin^{-1}\left(\frac{n_p(\lambda)}{n_g(\lambda)}\sin\left(\theta_1 + \frac{\varepsilon}{2}\right)\right) \quad (24)$$

Where $n_p(\lambda)$ is the wavelength dependent index of refraction of the grating.

The grating equation is:

$$\sin\alpha + \sin\beta = \frac{-m\lambda}{d} \quad (25)$$

Where $\alpha$ is the angle of incidence onto the grating, $\beta$ is the exit angle of the grating, m is the diffraction order, $\lambda$ is the wavelength of the incident light, and d is the groove spacing. Rearranging for the exit angle yields:

$$\beta = \sin^{-1}\left(\frac{-m\lambda}{d} - \sin\alpha\right) \quad (26)$$

For a fixed input angle, in the small angle approximation, the angular change as a function of wavelength is:

$$\frac{d\beta}{d\lambda} = \frac{-m}{d} \quad (27)$$

Wavenumber, $\nu$, is:

$$\nu = \frac{1}{\lambda} = \frac{k}{2\pi} \quad (28)$$

Converting the dispersion equation to wavenumber, $\nu$, yields:

$$\frac{d\beta}{d\nu} = \frac{-m}{\nu^2 d} \quad (29)$$

The Sellmeier equation relates the index of refraction $n(\lambda)$ to the wavelength of light using well-characterized, commonly known coefficients, B1-3 and C1-3:

$$n(\lambda) = 1 + \frac{B_1\lambda^2}{\lambda^2 - C_1} + \frac{B_2\lambda^2}{\lambda^2 - C_2} + \frac{B_3\lambda^2}{\lambda^2 - C_3} \quad (30)$$

Equation 30 in terms of wavenumber is:

$$n(\nu) = 1 + \frac{B_1}{1 - \nu^2 C_1} + \frac{B_2}{1 - \nu^2 C_2} + \frac{B_3}{1 - \nu^2 C_3} \quad (31)$$

This equation can be used to model the index across the wavelengths or wavenumbers for a given SDOCT wavelength range.

Figure 7:
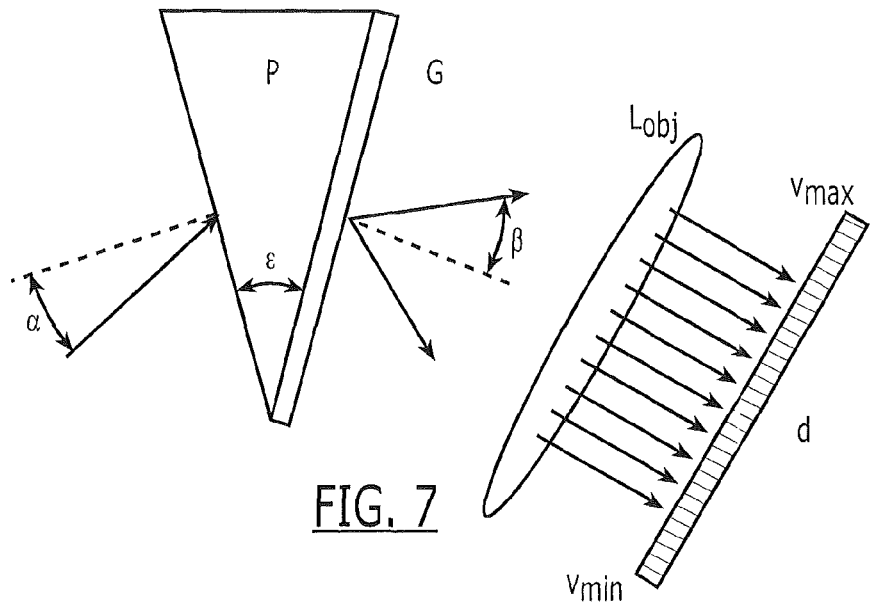
FIG. 7 is a block diagram illustrating a GRISM in accordance with some embodiments of the present inventive concept.

A k-linear GRISM is a combination of a prism and a grating in which the wavenumber dispersion of the prism balances the wavenumber dispersion of the grating. This can be tailored to yield approximately constant wavenumber dispersion across the output of the GRISM. One implementation of this design uses an isosceles prism with a flush-mounted VPH grating as illustrated in FIG. 7 of the present application. Alternative designs that reverse the order of grating and prism, or that utilize prisms on both the entrance face and exit face of the gratings may be employed without deviating from the invention. Note also that a chirped holographic grating can be tailored to replicate the transmission function of generally any GRISM. For example, a chirped grating holographically written will perform as the equivalent GRISM, without the need for mounting a physical GRISM to the grating in the spectrometer. The concept of chirped gratings are discussed in, for example, U.S. Pat. Nos. 4,834,474 and 7,224,867. Techniques for designing a transfer function and preparing a holographic transmission filter to provide the targeted transfer function are discussed in, for example, U.S. Pat. No. 7,519,248. These concepts have not previously been applied to k-linearized spectrometers.

In particular, as illustrated in FIG. 7, P and G are the prism and grating, respectively. $\varepsilon$ is the vertex angle of the prism, $\alpha$ is the angle of incidence onto the prism and $\beta$ is the deflection angle from the GRISM. As illustrated, d is the width of the detector, for example, 20.48 mm. The objective lens $L_{obj}$ represents the optics used to focus the GRISM output across the detector array. $\nu_{min}$ and $\nu_{max}$ are the wavenumber range minimum and maximum values, respectively.

Figure 8:
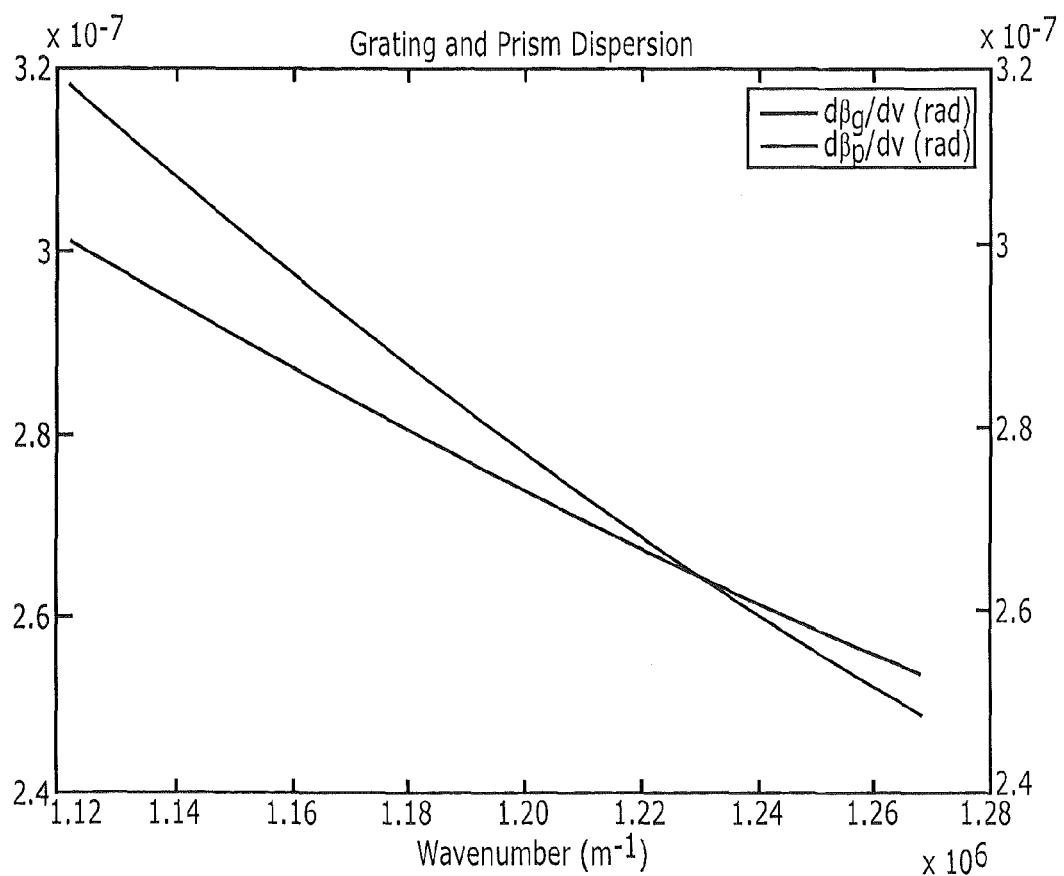
FIG. 8 is a graph illustrating grating and prism dispersion in accordance with some embodiments of the present inventive concept.
Figure 9:
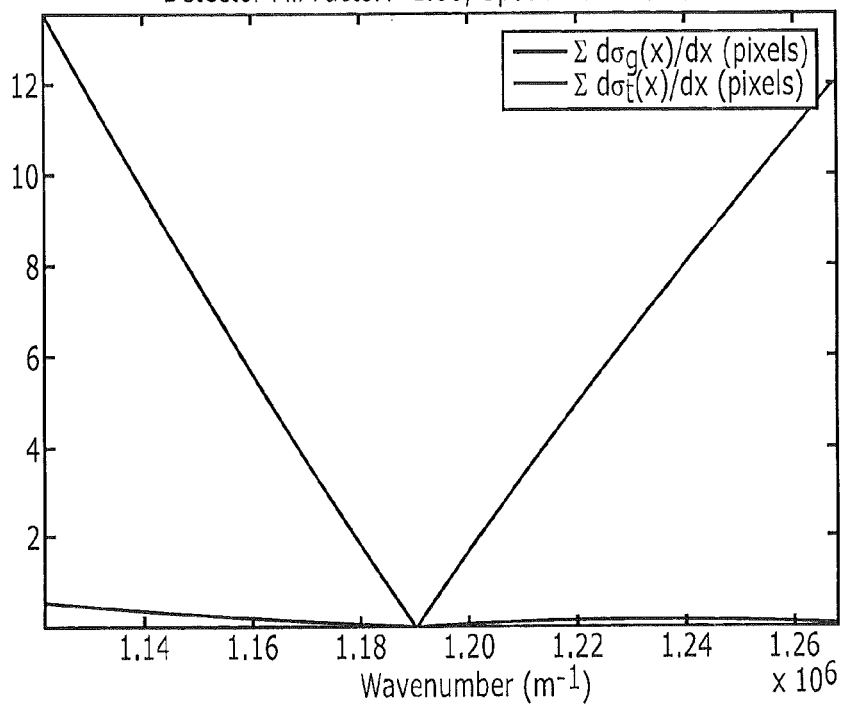
FIG. 9 is a graph illustrating cumulative wavenumber sampling shift as a cumulative error in channel position from pixel position, as referenced to the center pixel, due to dispersion in accordance with some embodiments of the inventive concept.
Figure 10:
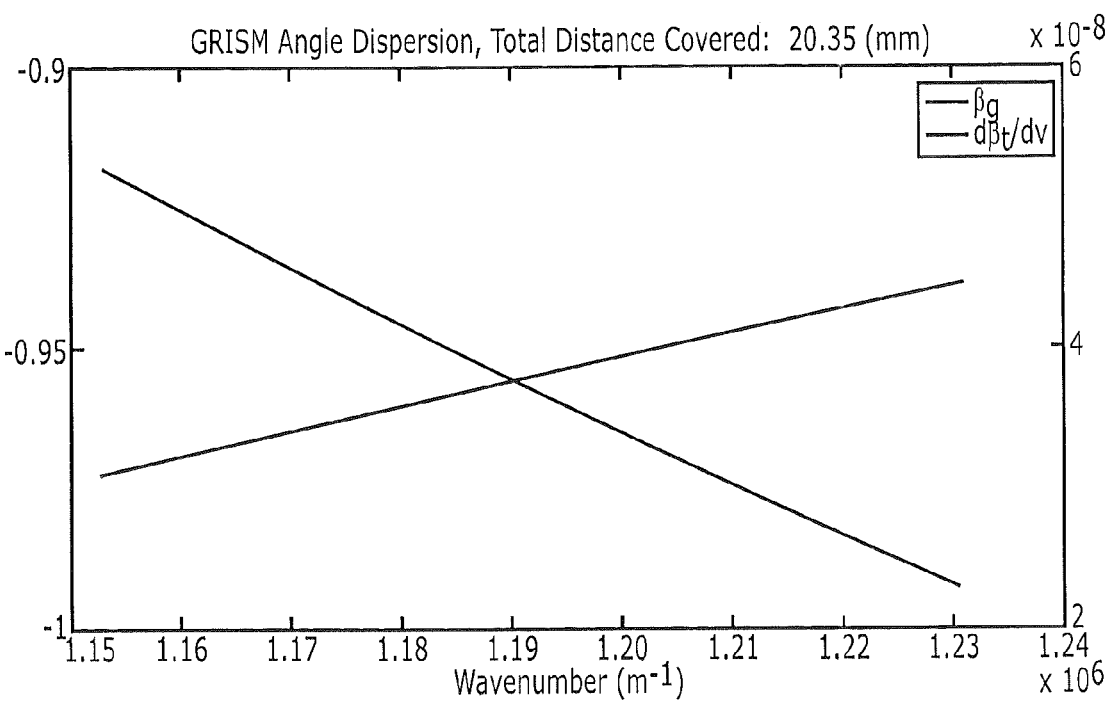
FIG. 10 is a graph illustrating GRISM angle dispersion in accordance with some embodiments of the present inventive concept.

FIG. 8 is a graph illustrating grating and prism dispersion in accordance with some embodiments of the present inventive concept. The dispersions of grating and prism are additive, such that the utilization of a prism reduces the dispersive power required of the grating. FIG. 9 is a graph illustrating cumulative pixel shift from center pixel due to dispersion in accordance with some embodiments of the inventive concept. A non-linearized spectrometer will not support a fully frequency-channelized set of spectral elements whereas a k-linear spectrometer can be channelized such that the cumulative offset of the Nth frequency channel from the Nth detector pixel is less than one pixel, and preferably less than one-half pixel. FIG. 10 is a graph illustrating GRISM angle dispersion in accordance with some embodiments of the present inventive concept, demonstrating the linearity with respect to wavenumber.

Non-ideal spectral sampling in FDOCT systems imposes a depth-dependent falloff of Signal-to-Noise Ratio (SNR). This falloff is based on the lineshape of the sampled element. For example, if the detected sampling function is a square pixel (rect function), then the transform of the sampling function is a sync function, and the shape of the sync function defines the falloff window.

Sensitivity falloff is in effect a characteristic of the finite coherence length of each sampled spectral element. In principle, sampling a comb of single frequencies, for example, a comb of delta functions, would completely eliminate sensitivity falloff. This is not achievable in practice. However, a comb convolved with a function, for example a Gaussian or Lorentzian, whose width is less than the comb spacing will demonstrably improve the falloff characteristics; the narrower the convolving function, or stated alternatively the smaller the duty cycle of the comb, the greater the positive impact on sensitivity falloff. This effect will be operative for any implementation of FDOCT, whether SDOCT or SSOCT, and whether applied with a resampled wavelength-sampled spectrum or a k-linear sampled spectrum, though operation in conjunction with a k-linear sampling, such that each sampled element records a spectral element of the comb, may be preferred.

A Fabry-Perot etalon can be used to provide such a comb source. A practical etalon may be composed of a glass block with 2 partially reflecting surfaces. As will be described, the two key attributes of the etalon are the free spectral range (FSR) and the Finesse. The FSR determines the sampling interval, which in some embodiments is designed to match the desired sampling interval, for example, the pixel spacing of the k-linear spectrometer or the k-trigger of the SSOCT light source. The FSR is closely related to the optical path length through the etalon. The Finesse sets the spectral width at each output frequency, or the duty cycle of the etalon transmission function. The Finesse is closely related to the reflectivity of the interfaces of the etalon.

Light incident etalon, normal to the surface or angled, will either pass through block or reflect from the block (assuming a lossless etalon interior). Transmission through the block is defined by:

$$T_e = \frac{T^2}{(1-R^2)\left(\frac{\sinh\gamma}{\cosh\gamma - \cos\delta}\right)} \quad (32)$$

Where T and R are the surface transmission and reflection values, $$\gamma = \ln\left(\frac{1}{R}\right),$$

and $\delta$, the phase of the light traveling through the block, is defined by:

$$\delta = \frac{4\pi}{\lambda} nl\cos\theta \quad (33)$$

Where n is the index of refraction of the glass block, $\lambda$ is the wavelength of the incident light, l is the thickness of the block, and $\theta\square$ is the angle of incidence onto the block.

The Free Spectral Range (FSR) of the etalon defines the spacing between adjacent transmission peaks and is defined by:

$$FSR = \frac{\lambda_0^2}{2nl\cos\theta + \lambda_0} \quad (34)$$

Where $\lambda_0$ is the center wavelength of the transmission peak. The Full Width at Half Maximum (FWHM or $\Delta\lambda$) of each transmission peak is related to the finesse, $\mathcal{F}$, of the etalon by:

$$\mathcal{F} = \frac{FSR}{\Delta\lambda} = \frac{\pi}{2\arcsin(1/\sqrt{F})} \quad (35)$$

Where F is the coefficient of finesse, which is defined by:

$$F = \frac{4R}{1-R^2} \quad (36)$$

The thickness of the block and the reflectivity of the surfaces can be tailored to provide a comb source for a given wavelength range that provides a sub-interval lineshape and a FSR equal to the spectral sampling interval.

Figure 23:
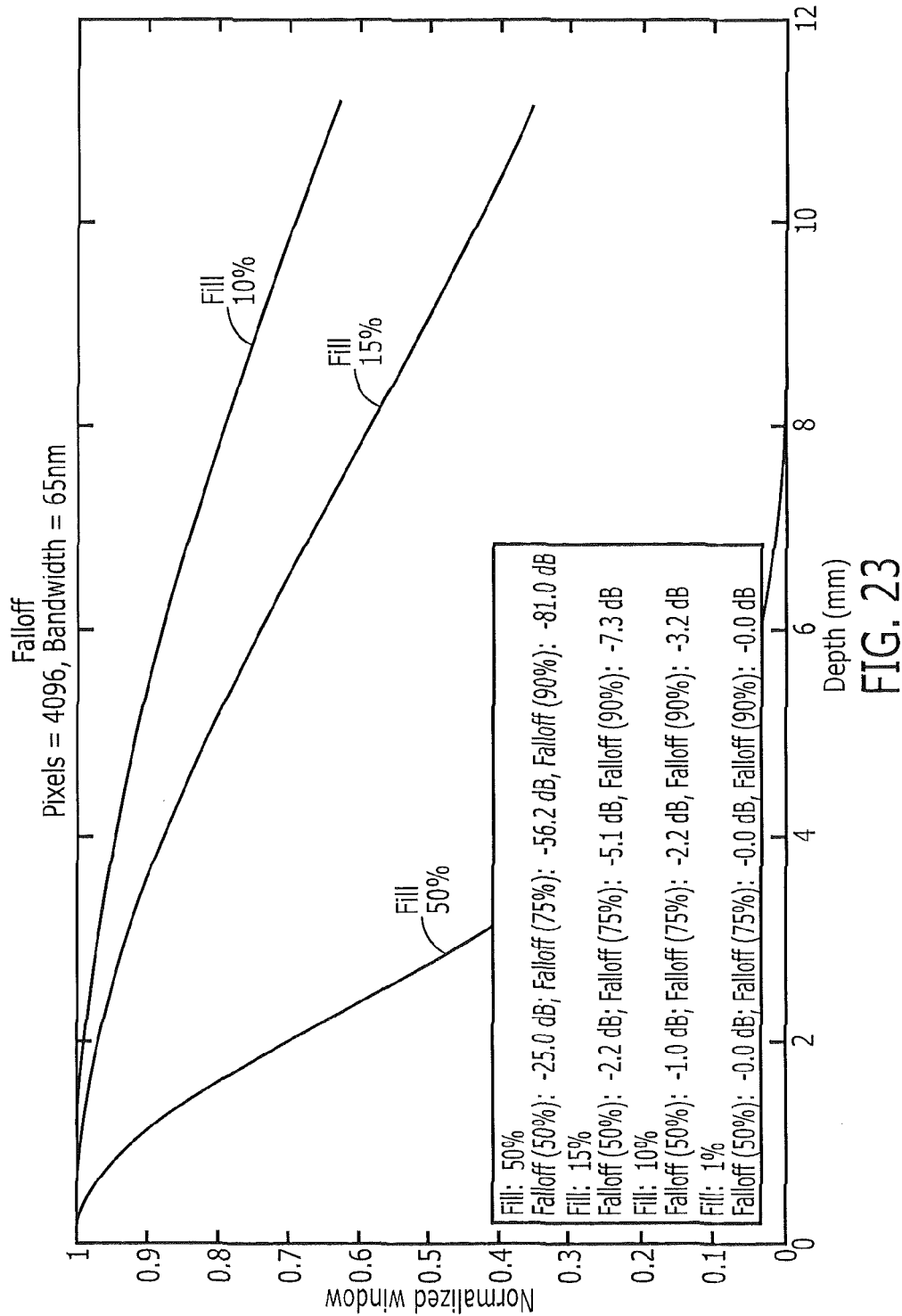

The maximum depth of a spectrometer is defined by the frequency spacing at the detector; finer frequency sampling yields a deeper maximum depth. 56 nm from 812-868 nm dispersed across 2048 pixels will provide a spectral sampling of 0.027 nm/pixel and a maximum depth of 6.55 mm. Assuming an incident angle of $\pi/8$ (22.5°) and an index of refraction of the etalon glass of 1.55, the FSR and FWHM can be tailored to provide sub-pixel FWHM and transmission peak spacing equal to the spectral sampling interval. Assuming a GRISM—based, constant wavenumber dispersion spectrometer is in place, the spectral sampling will be evenly spaced from $1.15 \times 10^6$ in$^{-1}$ to $1.23 \times 10^6$ m$^{-1}$. Reflectivity R of 0.24 yields a finesse of 1.1, and for a thickness of 10 mm, this yields a mean FSR of 0.024 nm and a FWHM of 0.021 nm. Increasing the finesse shortens the FWHM as illustrated below in FIG. 21 and subsequently the falloff effect as illustrated in FIG. 23, but this also decreases the total power output of the source.

For comprehensive FDOCT imaging of the eye by rapidly switching between imaging modes designed for imaging different ocular structures along the visual axis, it would be desirable for the imaging depth (axial field of view) of each mode to be optimized for the expected length and desired axial sampling density of each structure. For example, for imaging of the entire anterior segment, the optimal imaging depth is the expected maximum anterior segment depth of the anticipated patient population, which may be 6 to 8 millimeters. For imaging of the retina, which is less than about 1.0 mm thick in most locations and contains many closely spaced layers and structures, it may be preferable for the retinal imaging mode to have a shorter imaging depth and denser axial sampling.

In all FDOCT systems, as has been expressed, there is an inverse relationship between the imaging depth $z_{max}$ and the spectral sampling interval in wavenumber units $\delta_s k$ given by:

$$z_{max} = \frac{\pi}{2 \cdot \delta_s k} \quad (37)$$

The total sampled spectral width is given by the spectral sampling interval $\delta_s k$ multiplied by the number of spectral samples acquired per A-scan, typically several thousand, and thus the depth sampling density is given by the imaging depth divided by the number of spectral samples, or some multiple of that number if interpolation is performed. In SDOCT systems, the spectral sampling interval $\delta_s k$ is typically fixed by the spacing of the pixels on the array detector used in the spectrometer and the magnification and spectral dispersion of the internal optical elements of the spectrometer. In SSOCT systems, however, the spectral sampling interval $\delta_s k$ is determined by the sweep rate of the light source and/or the electronic sampling rate of the analog to digital converter which is recording the SSOCT signal, at least one of which may be rapidly adjustable electronically or by other means. In the case of SSOCT, therefore, it will be desirable to adjust the spectral sampling interval and thus the imaging depth and depth sampling density (according to the prescription in equation 3) on the fly according to the structure or part of the eye which is being imaged. This imaging depth switching may be coupled to sample and reference arm mode switching, such that when switching the sample arm optics and reference arm delay from the anterior segment to the retina, for example, the imaging depth is also switched to allow for optimal imaging depth and sampling density of retinal structures. Or, the imaging depth and depth sampling density may be varied within a single operating mode of the sample and reference arm optics, for example to switch between short imaging depth, high spatial sampling density imaging of the cornea and long imaging depth, lower spatial sampling density imaging of the entire anterior segment.

In unmodified SDOCT systems, $\delta_s k$ is usually limited by the spectral resolution of the spectrometer including the finite spacing of the CCD pixels and diffraction in the spectrometer. In unaltered SSOCT systems, $\delta_s k$ is typically limited by the instantaneous lineshape of the swept laser source, although other factors such as the bandwidth of the detection electronics may also come into play.

In comprehensive ocular SSOCT systems as described above wherein the spectral sampling interval and depth sampling density are adjusted as per equation 3 according to the structure or part of the eye which is being imaged, it is desirable to further implement a comb filter for decreasing the extent of sensitivity falloff which is also suitably adjustable to maintain the comb spacing or FSR as the spectral sampling interval is adjusted. In Fabry-Perot etalons, the FSR is related to the thickness of the etalon, the index of refraction of the material inside the etalon, and the angle of light incidence upon the etalon. According to some embodiments, one or more of these parameters should be varied in synchrony with changing the spectral sampling interval $\delta_s k$ in order to keep the comb filter peaks within their respective spectral sampling intervals. In some embodiments, this may be done by employing a tunable Fabry-Perot filter, for example, which utilizes a piezo-electric element to electronically tune its FSR. Electronic control of the FSR of such a filter may be electronically coupled to the mechanism for changing the spectral sampling interval $\delta_s k$, for example by changing the digitization rate of the analog-to-digital converter.

Note that in such a case the FSR of the comb filter matches the sampling rate of the detector. This is the function of k-triggers commonly deployed in SSOCT systems to trigger the acquisition of spectral elements. Thus it is conceivable to use the comb filter for a secondary function, to act as the system k-trigger. The converse property does not hold. In particular, a k-trigger is not implemented in current systems to operate as a comb source generator for the SSOCT system. The proposed comb filter may be used as a k-trigger in at least two different modes. In a first mode, a small fraction of the transmissive (T) output of the comb filter is split out of the source path to k-trigger circuitry. In such a configuration, the k-trigger implementation is directly analogous to implementations currently used in the art, with the benefit that a separate device is not required. This mode is fully functional, but comes at some cost to the power available for imaging.

Figure 24:
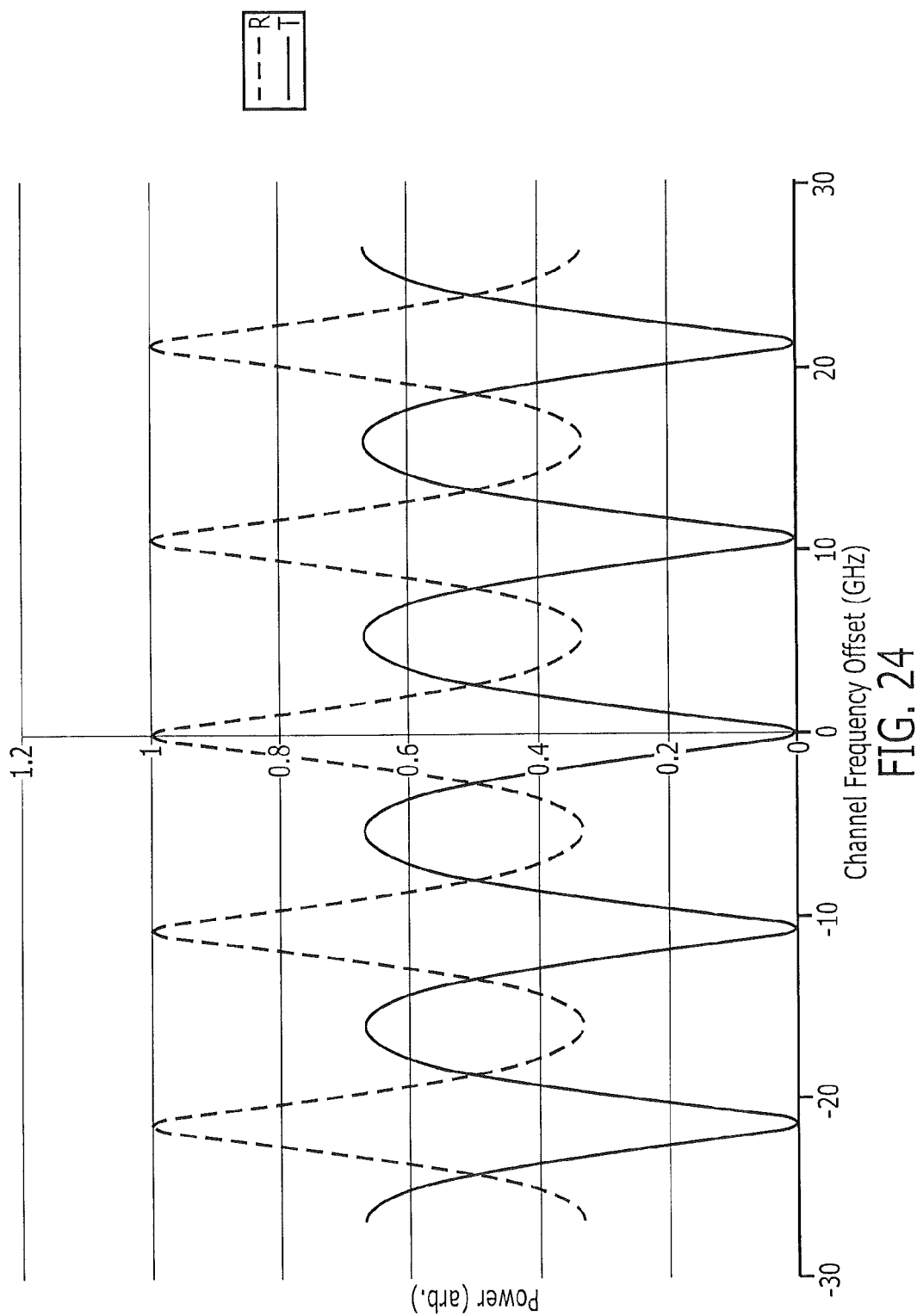

A second mode is to use the back-reflected (R) light from the filter. The backreflection from a lossless etalon filter is the spectral complement to the transmission through the filter, as illustrated in FIG. 24. This backreflection may be used as the k-trigger for an SSOCT system. Embodiments illustrating the second mode including a swept source followed an optical isolator, an etalon filter, and an optical circulator, will be discussed further below with respect to FIG. 19. The backreflected output from the etalon is directed to k-trigger circuitry and applied to trigger spectral sampling of a balanced heterodyne detector. The balanced detector sees interference signature both from the detector port of the coupler, and the shunt port of the optical circulator.

To resolve the complex conjugate artifact, several academic groups have pointed out that a second spectral interferogram may be obtained with the phase offset ϕ shifted in phase by $\pi/2$. Combining the real and imaginary parts yields the complex interferometric signal $\hat{D}_i[k_m]=\hat{D}_i^0[k_m]+j\hat{D}_i^{90}[k_m]$, the Fourier transform of which reveals an A-scan with the position of the sample arm reflector unambiguously determined. A method to obtain the complex signal using only two phase stepped scans has been demonstrated, but completely artifact-free tissue imaging has only been demonstrated using a 5 step algorithm in which the additional phase steps were necessary to compensate for phase errors.

Figure 11:
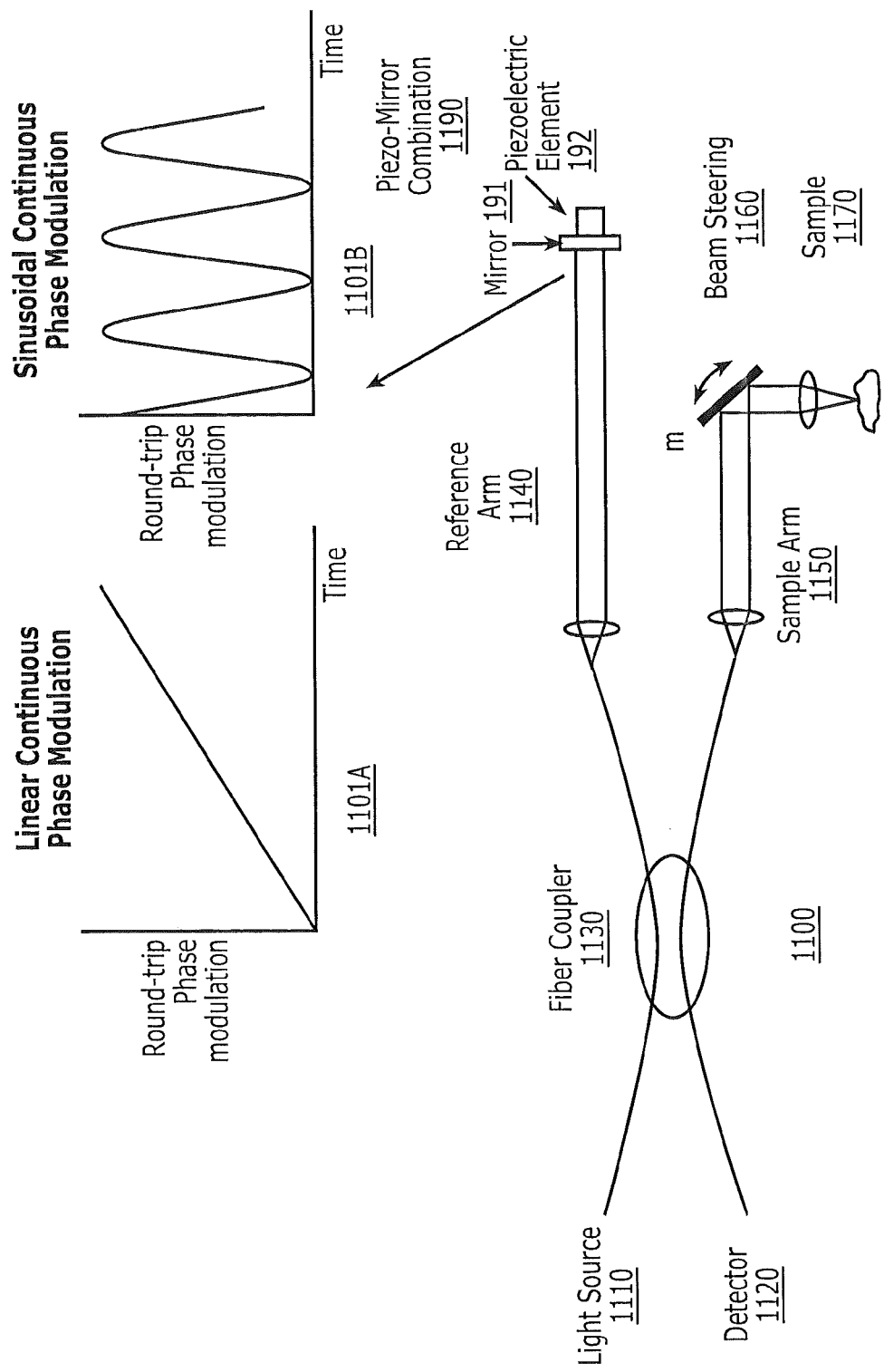
FIG. 11 is a schematic block diagram illustrating an optical coherence tomography (OCT) system including a piezoelectric transducer (PZT) element in accordance with some embodiments of the present inventive concept.

For an SDOCT system embodiments for complex conjugate removal (CCR) may be via sinusoidal phase modulation as discussed in, for example, commonly assigned U.S. Pat. No. 7,742,174, the disclosure of which has been incorporated herein above. In particular, the system discussed in accordance with some embodiments of U.S. Pat. No. 7,742,174 is illustrated in FIG. 11. Referring to FIG. 11, the optical coherence tomography (OCT) system 1100 includes a piezoelectric transducer (PZT) element. As illustrated in FIG. 11, the system 1100 further includes a light source 1110, a detector 1120, a fiber coupler 1130, a reference delay 1140, a piezomirror combination 1190, a beam steering unit 1160, a sample arm 1150 and a sample 1170. The light source 1110 may include a broadband light source and the detector 1120 includes a spectrometer illuminating a multichannel detector, such as a linear charge-coupled device (CCD) array. A piezomirror combination 1190 is located in the reference arm 1140 of the interferometer, which may include a mirror 1191 and a piezoelectric element 1192 as illustrated therein.

As discussed in U.S. Pat. No. 7,742,174, phase modulation (linear continuous phase modulation 1101A or sinusoidal continuous phase modulation 1101B) involves placement of a path length modulation in either the sample or reference arm of an SDOCT system which varies the differential path length between the arms with amplitude and phase given in the text preceding equation (14) in U.S. Pat. No. 7,742,174, at a rate corresponding to $\pi/4$ radians of phase modulation per A-scan integration time of the spectrometer. Then, each set of four sequential A-scan acquisitions are combined according to equation (14) of U.S. Pat. No. 7,742,174 in order to generate an A-scan with total depth equal to $2*z_{max}$ as defined above. If the amplitude, phase and frequency of the modulation are set as specified in U.S. Pat. No. 7,742,174, then the resulting A-scan should theoretically be completely free of DC, autocorrelation, and complex conjugate artifacts.

However, slight deviations from perfection in achieving these parameters such as will be experienced in any real physical implementation of sinusoidal phase modulation may lead to a degradation of performance compared to the ideal result in the form of incomplete complex conjugate artifact suppression. Thus, an additional step of applying quadrature projection processing as discussed with respect to FIG. 2 of U.S. Patent Application Publication No. 2008/0170219 may be applied to improve the complex conjugate artifact rejection, at the cost of a small amount of reduced signal to noise ratio. Quadrature projection processing is an algorithmic step which does not require any hardware modification and which reduces the complex conjugate artifact from imperfectly phase modulated SDOCT data by forcing the real and imaginary parts of the recorded A-scan signal to be orthogonal.

For an SSOCT system, some embodiments implement complex conjugate removal (CCR) using the heterodyne CCR method as discussed in commonly assigned U.S. Pat. No. 7,336,366, which involves introducing a frequency shift between the sample and reference arm light and thus shifting the carrier frequency of the image-bearing signal away from DC, about which the complex conjugate artifact is centered. With the addition of this frequency shift, the A-scan free of complex conjugate artifact is found from the Fourier transform of the detected signal, centered at the frequency shift value. If an A/D converter is used which has much higher bandwidth than the SSOCT signal itself, then the frequency shift value can be set to be many times the frequency encoding the $z_{max}$ value of the A-scan, thus the complex conjugate artifact will be located far in frequency space away from the A-scan data. If a very high sweep speed is used, however, such that the SSOCT signal already occupies a substantial fraction of the A/D converter bandwidth, then the complex conjugate artifact may only be shifted to the borders of the depth-doubled A-scan. This method of heterodyne CCR is consistent and will not interfere with the embodiments described above for filtering to improve sensitivity falloff and sampling to adjust maximum single-sided imaging depth.

Figure 2:
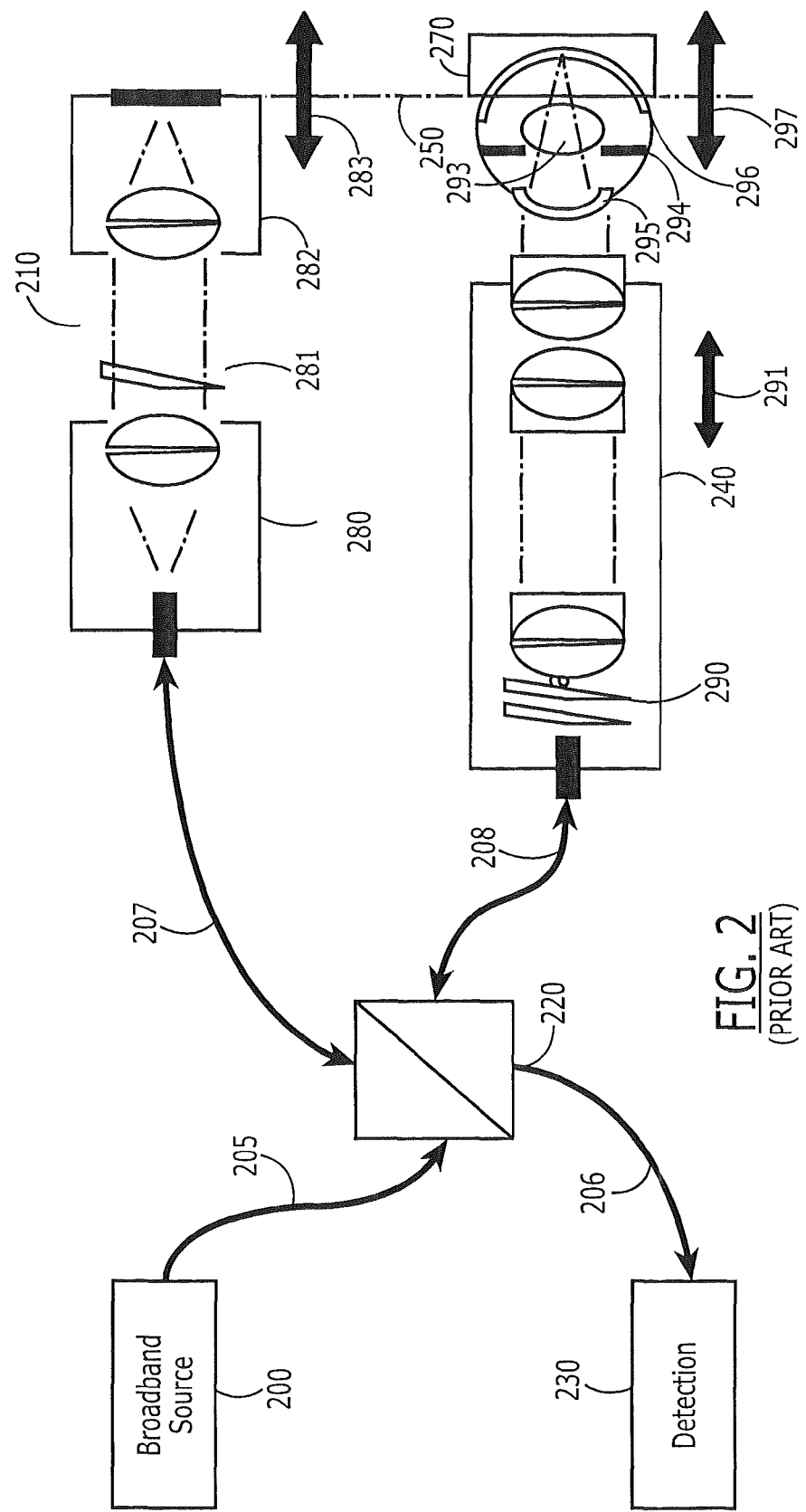
FIG. 2 is a block diagram illustrating a Fourier domain retinal optical coherence tomography system in accordance with some embodiments of the inventive concept.
Figure 3A:
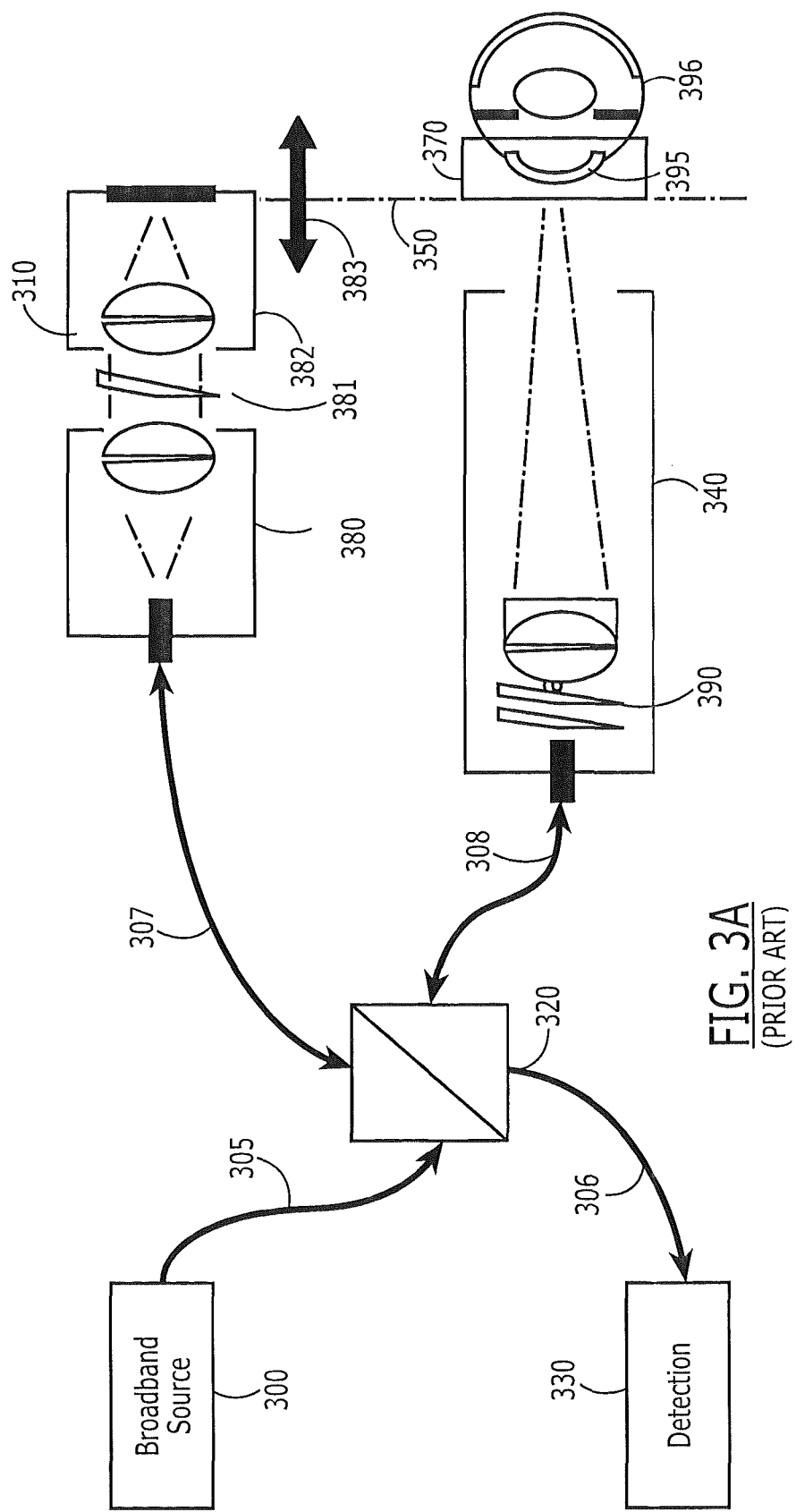
FIGS. 3A through 3C are block diagrams illustrating a Fourier domain corneal optical coherence tomography system in accordance with some embodiments.
Figure 3B:
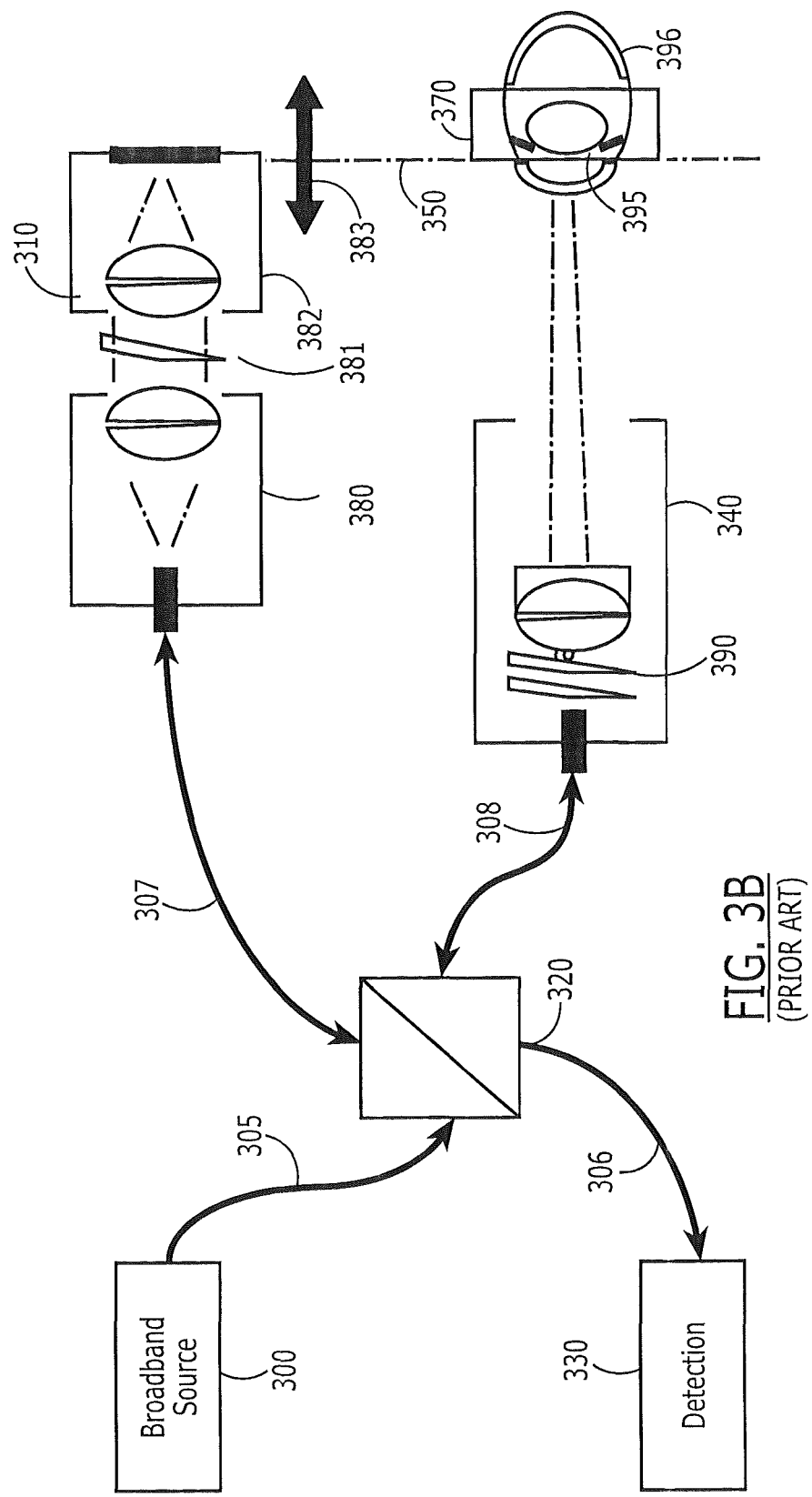
Figure 3C:
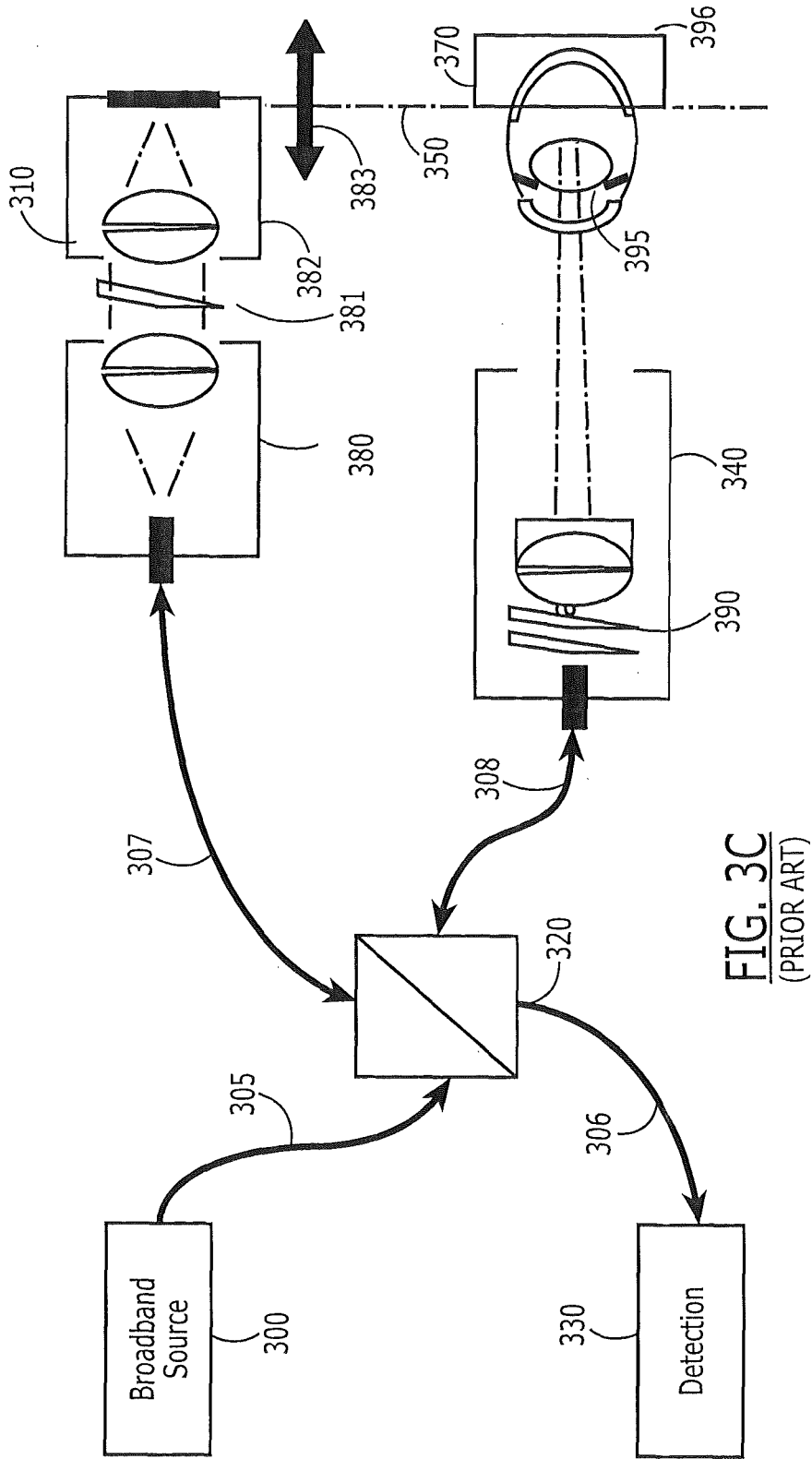

Some embodiments of the present inventive concept are directed to comprehensive volumetric imaging of all ocular structures along the visual axis using Fourier-domain optical coherence tomography (FDOCT). Current-generation FDOCT systems, including spectral-domain (SDOCT) and swept-source (SSOCT) implementations, are in routine clinical use for diagnosis of retinal pathologies. FDOCT systems have also been applied for imaging of the anterior segment of the eye. Existing optical designs for scanning the anterior segment and retina are illustrated in FIGS. 1 through 3 of the present application. FDOCT is useful for examination of the anterior segment of the eye, for diagnosis of corneal, iris, and lens pathologies as well as for quantitative biometry of the anterior segment including measurements of corneal refractive power, corneal thickness, anterior chamber depth, lens optical power, and lens thickness. These parameters resulting from anterior segment biometry, with the addition of eye length measurement, are needed for calculation of intraocular lens implant power for cataract surgery. Current methods for evaluation of these parameters are limited to measurement along a single axis, and thus provide only central values for these parameters which may not accurately account for off-axis variations and aberrations. With the ability to rapidly acquire densely sampled 2D images and 3D volumes of information, FDOCT offers the potential to perform substantially improved characterization of the refractive properties of the entire eye, if calibrated and correlated volumetric images of the anterior segment, lens, and retina could be acquired either simultaneously or in rapid succession in the same patient.

Current-generation FDOCT instruments, however, are not capable of imaging with sufficient depth field of view to record data from all of these structures with the same instrument without time-consuming interchange of optics and of the reference arm length. Thus, there is a need for FDOCT system designs capable of either simultaneous imaging of the anterior segment, lens, and retina or of rapidly switching between such modes during a rapid acquisition sequence which preserves their relative displacements in order to perform comprehensive volumetric imaging of all ocular structures along the visual axis. Such switching should preferably be rapid, on the time scale of a few A-scans acquisition time, i.e. a few milliseconds, and should allow for the maximum possible re-use of optics and mechanics in both modes to reduce total system cost and complexity.

Applying the techniques described in this inventive concept, a dynamically adjustable extended depth imaging system may be applied to ophthalmic imaging for targeted imaging of any region of the eye with optimized depth field of view and image resolution. FIGS. 12 and 13A-13E illustrate a series of imaging windows 1255 and 1355-1355"" that may be applied for a select variety of imaging circumstances, for example, vitreoretinal surgery, cataract surgery, cornea and anterior chamber surgery and the like. As illustrated in FIGS. 12 and 13A-13E, the series of windows may have a variety of sizes, shapes and locations in accordance with embodiments discussed herein.

Figure 12:
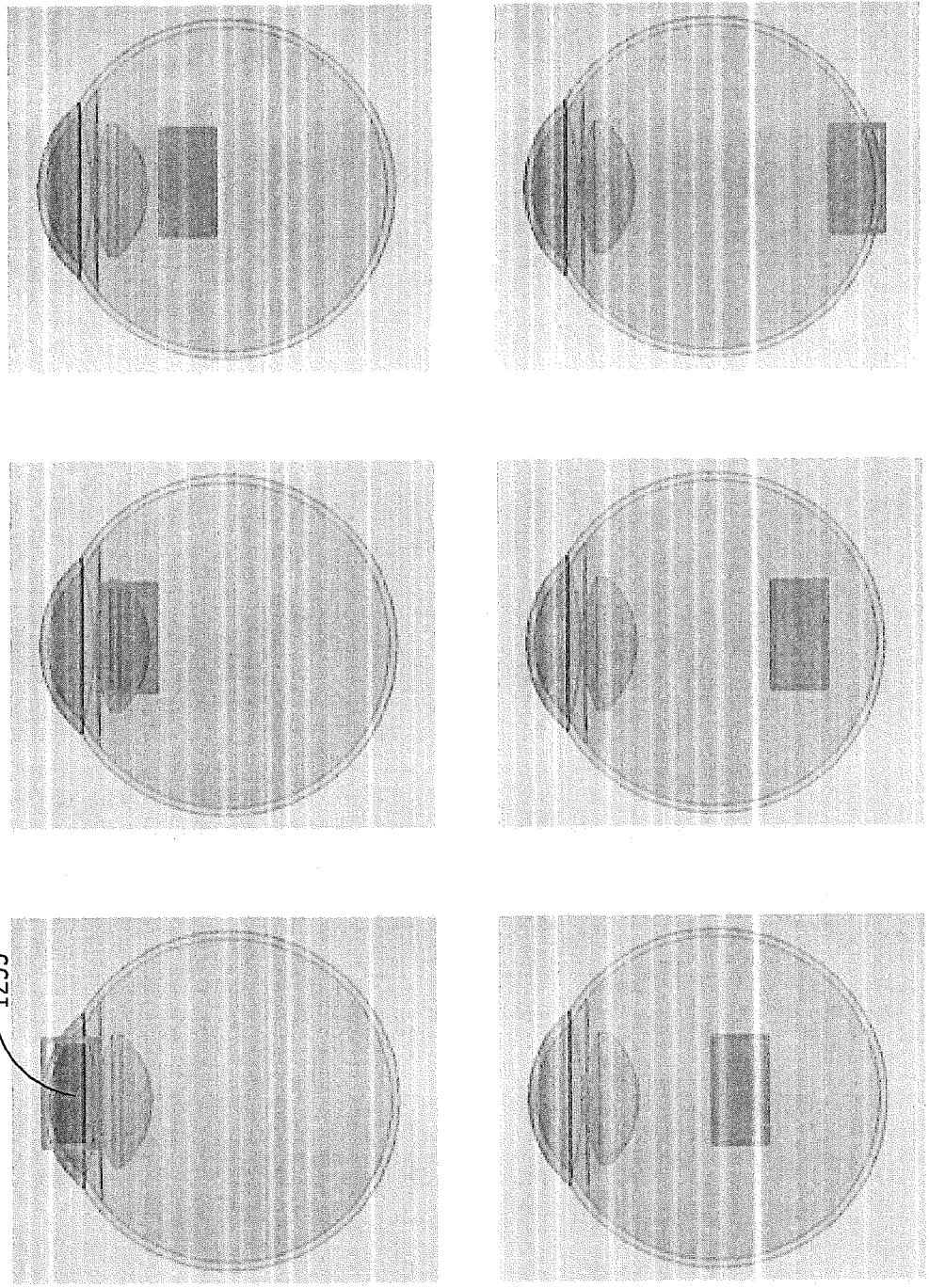
FIGS. 12 and 13A through 13E are diagrams illustrating a series of imaging windows that may be applied for a select variety of imaging circumstances in accordance with some embodiments of the inventive concept.

In particular, FIG. 12 illustrates using a normal imaging depth window 1255 to image the whole eye. As illustrated in FIG. 12, to image the whole eye using window 1255, six depths would have to be taken to obtain images of the whole eye. With each depth, a focal adjustment and reference arm adjustment is made.

Figure 13A:
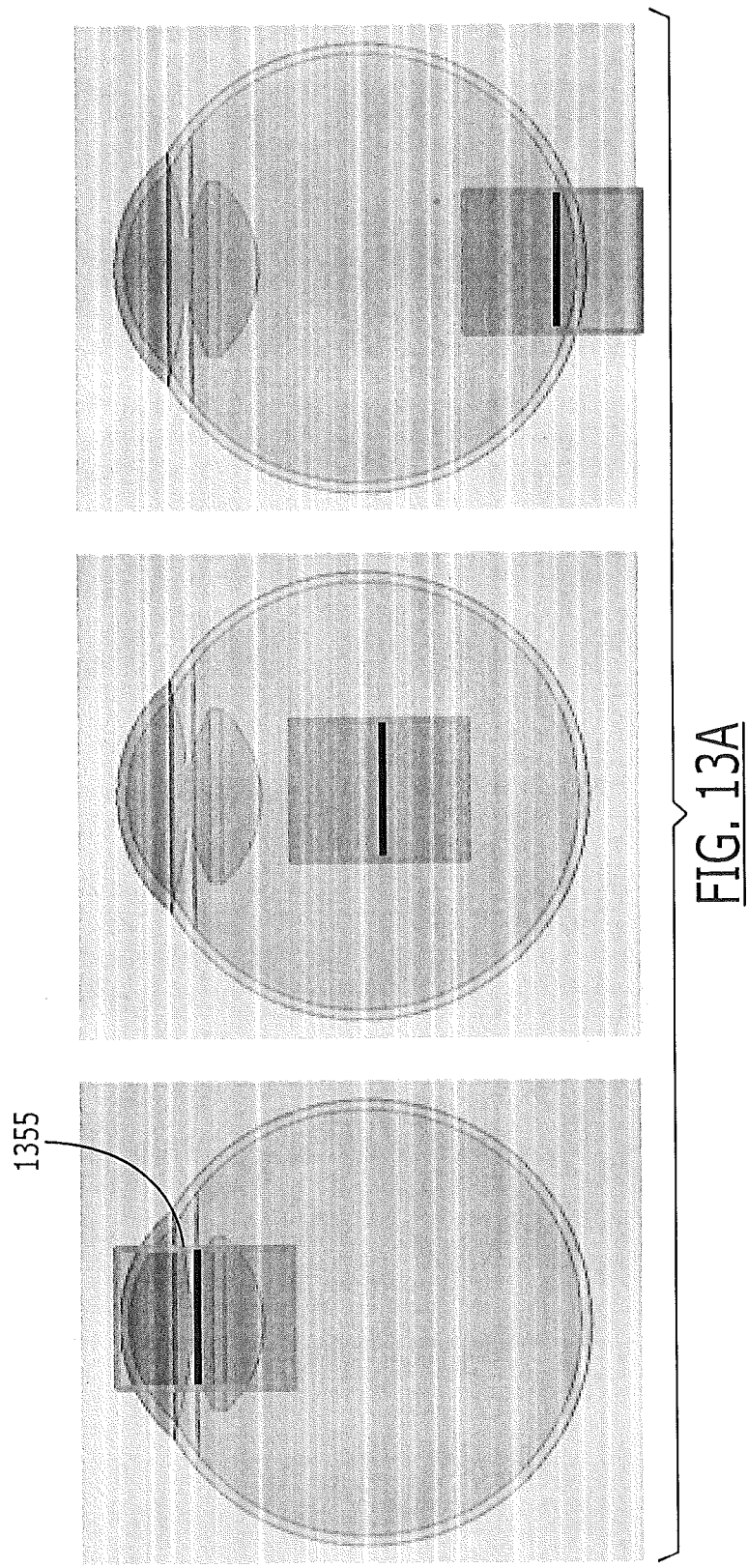

Referring now to FIG. 13A, as illustrated therein, using phase modulation and complex conjugate techniques discussed below, a window having a double depth 1355 may be used, which can decrease the number of steps from six in FIG. 12 to three steps in FIG. 13A. Each step also requires focal and reference arm adjustments, which can be fine tuned with continuous adjustments to the reference arm.

Figure 13B:
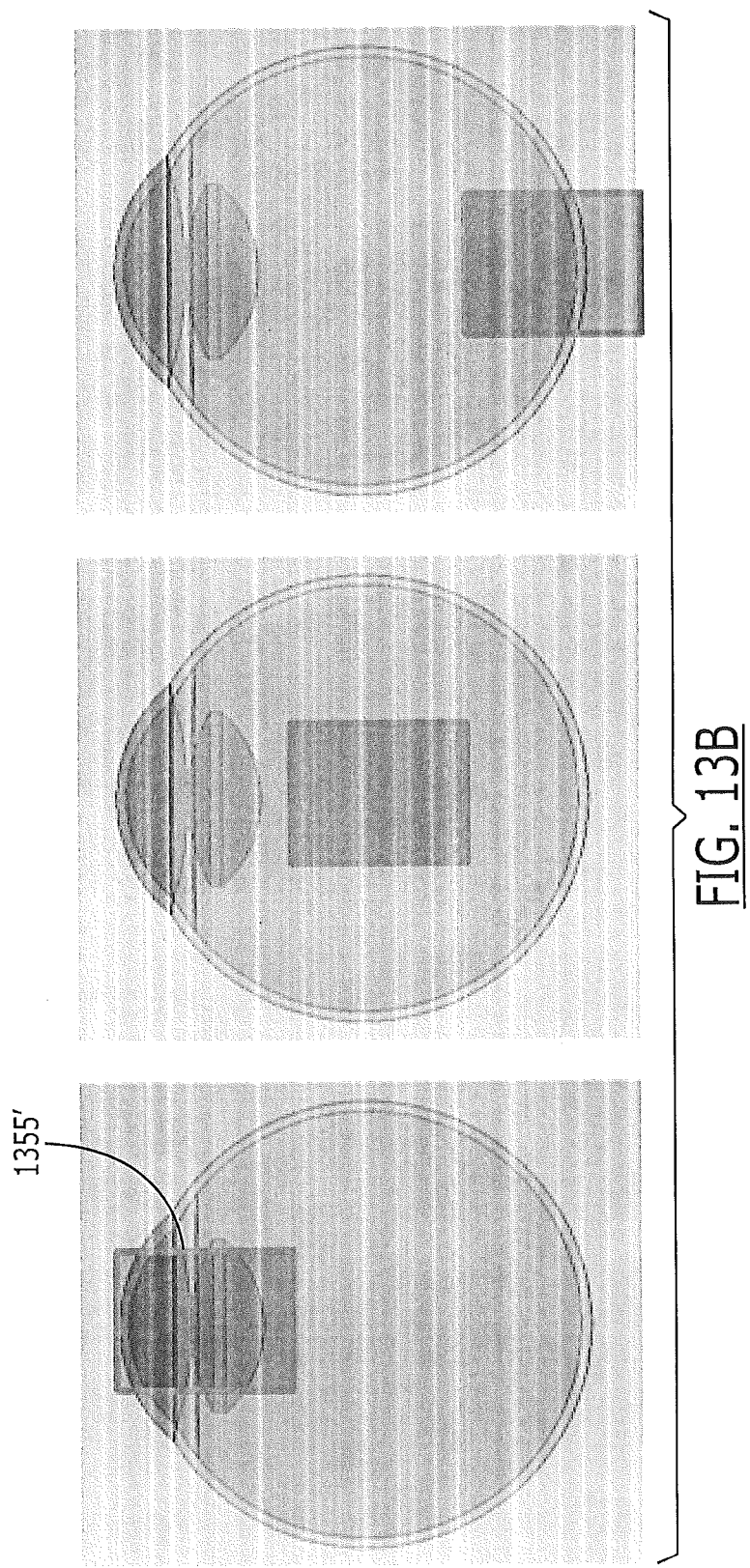

Referring now to FIG. 13B, as illustrated therein, using an extended depth window 1355' in accordance with some embodiments also allows the number of steps to be reduced from six steps in FIG. 12 to three in FIG. 13B. The extended depth windows 1355' are provided without the use of complex conjugate techniques. The front and reference arm optics are equivalent and, therefore, does not require phase modulation.

Figure 13C:
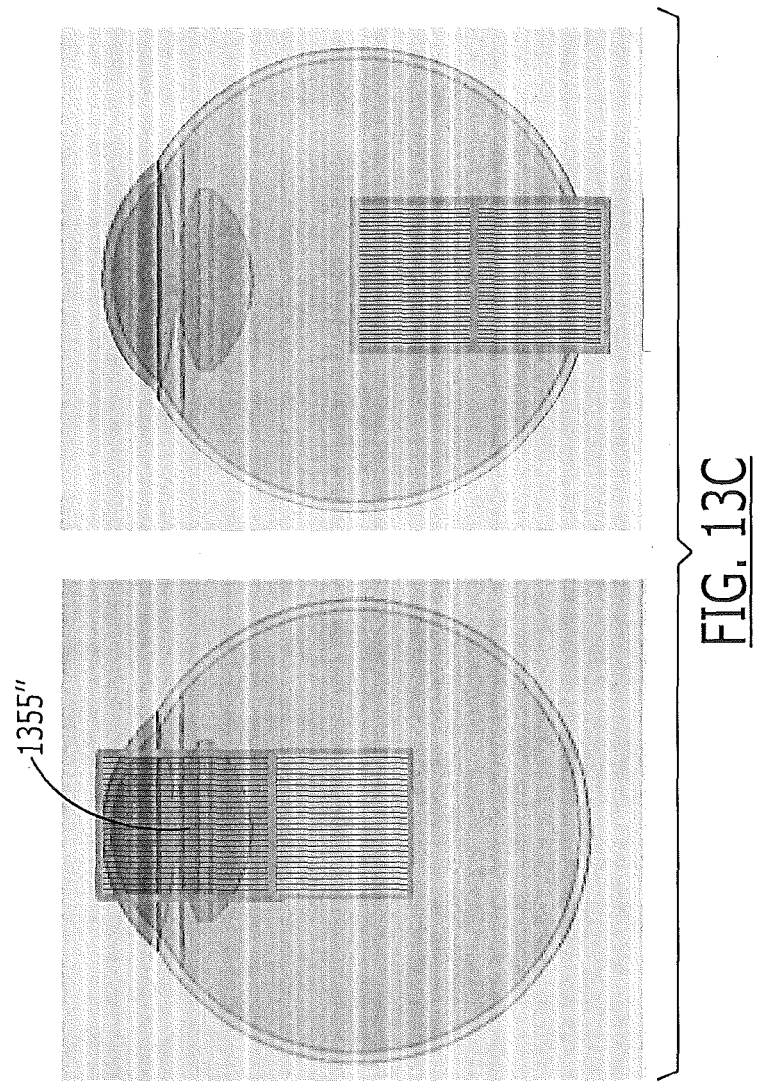

Referring now to FIG. 13C, using both techniques discussed above with respect to FIGS. 13A and 13B, i.e., a double depth and extended depth window 1355", the number of steps can be further reduced to two.

Figure 13E:
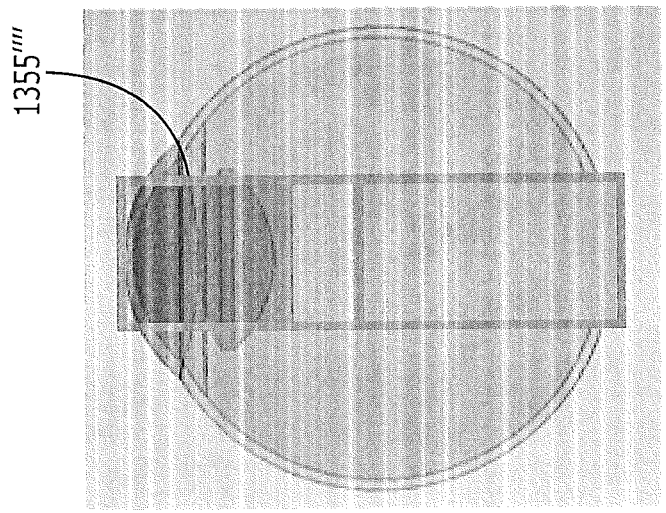
Figure 13D:
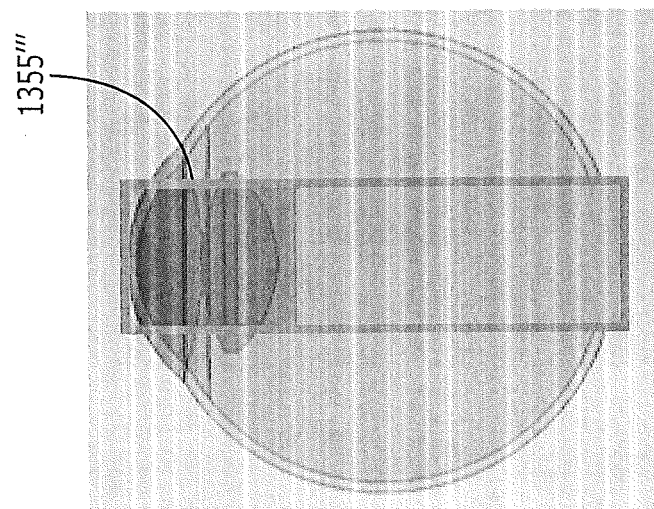

As illustrated in FIGS. 13D and 13E, the number of steps can be further reduced to one step. In particular, as illustrated in FIG. 13D, a single double depth window 1355''' can be used to image the whole eye. Alternatively, as illustrated in FIG. 13E, a single extended depth window 1355"" can be used to image the whole eye.

FIGS. 12-13E are intended to provide example techniques of how a whole eye can be imaged using various techniques. It will be understood that other techniques, number of steps and the like can be used without departing from the scope of the present inventive concept.

Figure 14:
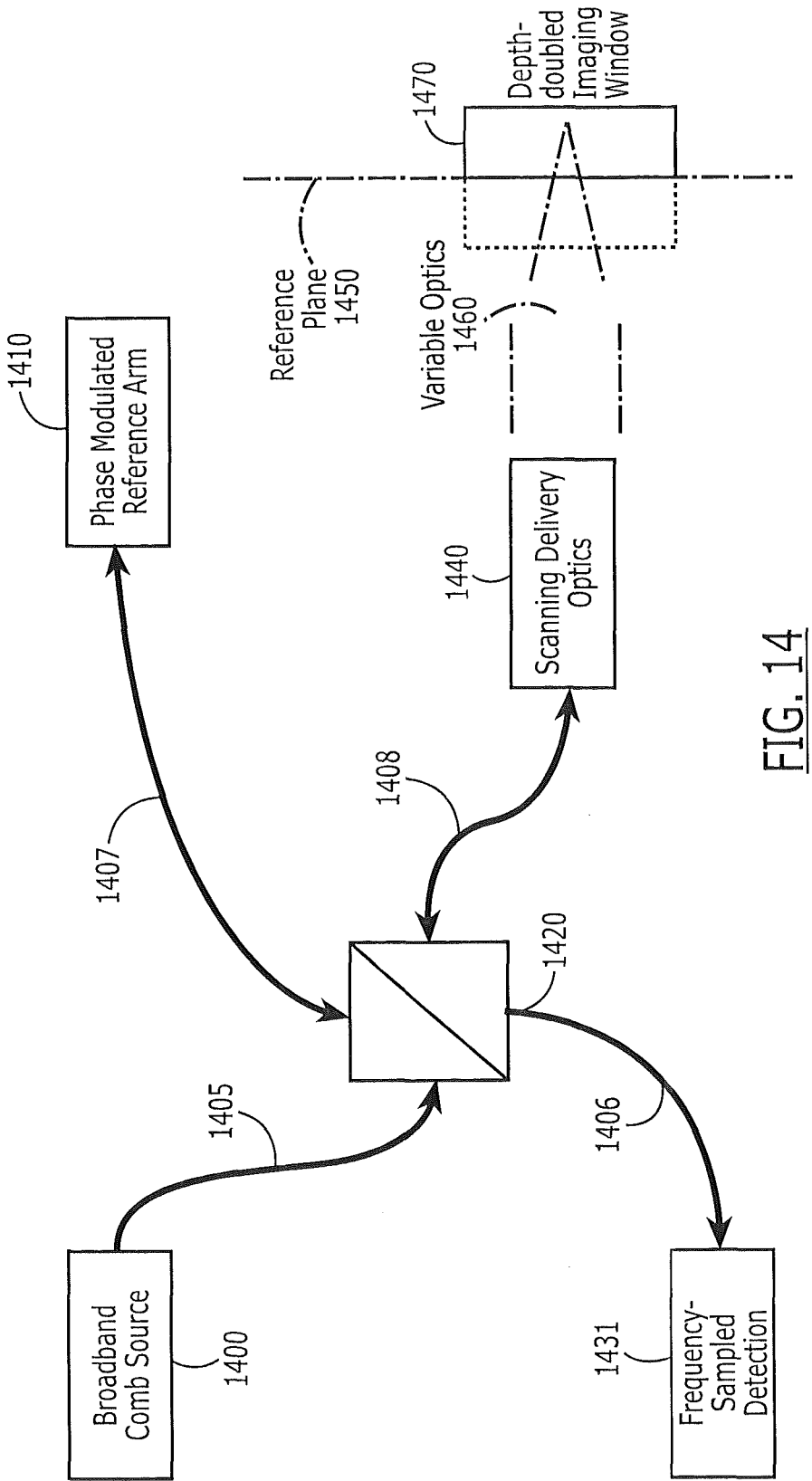
FIG. 14 is a block diagram of an extended depth fourier domain OCT imaging system in accordance with some embodiments of the inventive concept.

Referring now to FIG. 14, a block diagram illustrating an extended depth FDOCT system in accordance with some embodiments of the present inventive concept will be discussed. As illustrated in FIG. 14, the system includes a source 1400, a reference arm 1410 and a sample arm 1440 coupled to each other by a beamsplitter 1420. As further illustrated in FIG. 14, the beamsplitter 1420 is also coupled to a frequency sampled detection module 1431 over a detection path 1406 that may be provided by an optical fiber.

As further illustrated in FIG. 14, the source 1400 is coupled to the beamsplitter 1420 by a source path 1405. The source 1400 may be, for example, a broadband comb source. The reference arm 1410 is coupled to the beamsplitter 1420 over a reference arm path 1407. Similarly, the sample arm 1440 is coupled to the beamsplitter 1420 over the sample arm path 1408. The source path 1405, the reference arm path 1407 and the sample arm path 1408 may all be provided by optical fiber.

In some embodiments, the reference arm 1410 may be a phase modulated reference arm or a frequency-shifted reference arm as illustrated in FIG. 14, although embodiments of the present inventive concept are not limited to this configuration. Furthermore, the sample arm 1440 may include scanning delivery optics and variable optics 1460. Also illustrated in FIG. 14 are the reference plane 1450 and a representation of a depth doubled imaging window 1470 in accordance with some embodiments of the present inventive concept.

Figure 16:
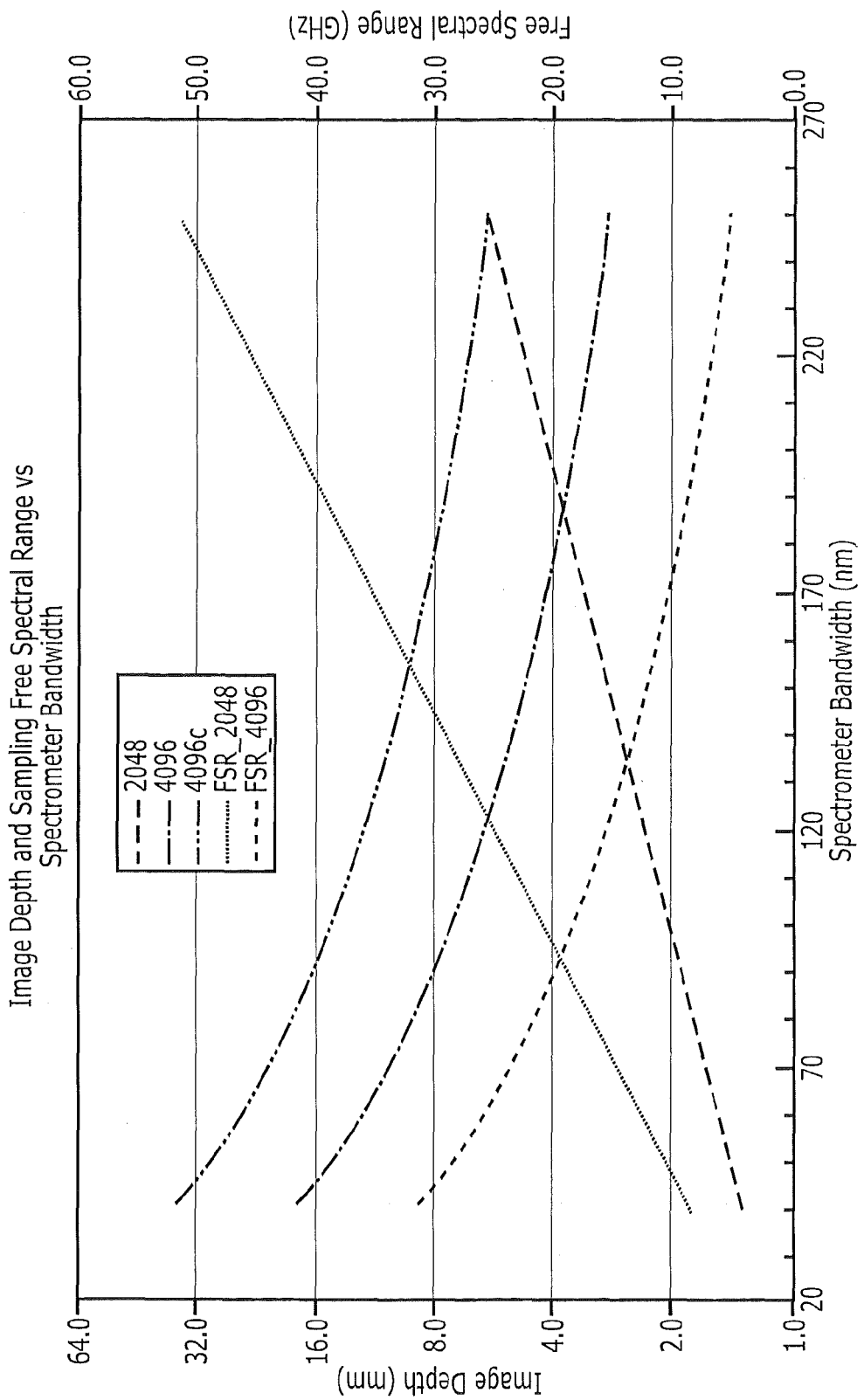
FIG. 16 is a graph illustrating image depth and sampling free spectral range vs. spectrometer bandwidth for an extended depth FDOCT system in accordance with some embodiments of the present inventive concept.

FIG. 15 is a graph illustrating depth and resolution vs. spectrometer bandwidth and samples for an extended depth FDOCT system in accordance with some embodiments discussed herein. FIG. 16 is a graph illustrating image depth and sampling free spectral range vs. spectrometer bandwidth for an extended depth FDOCT system in accordance with some embodiments of the present inventive concept. FIG. 15 illustrates the relationship between resolution and total imaging bandwidth, given single sided imaging at 2048 samples and 4096 samples, and complex conjugate resolved imaging at 4096 samples. As the bandwidth is constrained to increase image depth, resolution suffers. FIG. 16 illustrates the same bandwidth and sampling dependence of image depth, as well as the effective free spectral range associated with k-linearized sampling.

Embodiments of the present inventive concept directed to spectral domain OCT (SDOCT) will now be discussed. It will be understood that both SDOCT and SSOCT implementations will be discussed in detail herein. The selection of SDOCT or SSOCT is a function of desired imaging wavelength, availability of sources, and tradeoffs between key attributes, such as imaging speed and resolution. Implementations have been shown in the art that combine elements of SDOCT and SSOCT, and such implementations may benefit from application of the present inventive concept.

Referring again to FIG. 14, an SDOCT system in accordance with embodiments discussed herein includes a broadband optical source 1400, a source path 1405, a beam splitter/combiner 1420, a reference path 1407, a reference reflector 1410, a sample path 1408 with a scanning system and focal optics 1440/1460 configured to appropriately to image structures of the sample, such as the cornea, anterior chamber, iris, lens, posterior chamber, and retina of the eye, a detector path 1407, and a spectrographic detection system 1431.

In some embodiments, the SDOCT system is designed to image structures of the eye in the 800 nm to 900 nm wavelength range. The system may be designed to have a single-sided imaging depth (as measured in air) of about 7.0 mm, suitable for imaging the crystalline lens of the eye, and a complex-conjugate resolved imaging depth of about 14.0 mm, suitable for full range imaging of anterior of the eye, from corneal apex through the crystalline lens. Through translation of the reference arm 1407 and change in scanning and focal attributes of sample arm optics, the system is capable of imaging the entire optical structure of the eye in three steps.

In some embodiments, the broadband optical source 1400 is a superluminescent diode with a bandwidth of between about 40 nm and about 80 nm. The bandwidth of the source may be selected for axial resolution, but the useful bandwidth may be constrained by the total bandwidth of the detector. In some embodiments, the spectral characteristics of the source are such that the spectral power density at the edges of the spectrometer are attenuated at least about 6 dB from the peak power density, and may be about 10 dB. If the optical power at the edges of the spectrometer is too high, the image may exhibit ringing around bright features; numerical windowing of the acquired spectrum will reduce this artifact. The parameters of the numerical windowing may be selected to reduce the ringing by smoothly attenuating the signal to meet the stated conditions. For example, a cosine-squared window may be applied to the data immediately prior to the Fourier transform, or a raised Gaussian function may be applied ($e^{-x^4}$).

Although embodiments are discussed herein as having a superluminescent diode for the broadband optical source 1440, embodiments of the present inventive concept are not limited to this configuration. However, the superluminescent diode may be the most cost effective in this application, where ultra-wide bandwidth may not be required.

In some embodiments, the paths may be combined using single-mode optical fiber, such as Corning HI780. A fiber optic coupler may be used as the beam splitter/combiner 1420. The splitting ratio of the coupler can be chosen to optimize power to the sample and signal-to-noise ratio of the detection system. In some embodiments, the splitter 1420 may have a 80/20 split ratio, with 20% of the source light directed to the sample and 80% directed to the reference arm.

The reference path directs light from the coupler to an optical reflector. The path length of the reference arm may be designed to match the path length to the region of interest for the sample under test. In some embodiments, the reference arm 1407 has a translation capability to adjust to varying regions for a sample under test, which may be particularly important for imaging at multiple depths within one sample, such as an eye. The reference arm 1407 may be continuously translated, translated in steps through switches to predetermined path lengths, or a combination of the two without departing from the scope of the present inventive concept. Generally, the reference arm may be finely adjustable to a precision of at least about 100 µm to accurately position the sample within the FDOCT imaging window 1470.

The sample arm 1408 includes scanning optics, preferably scanners configured to scan a beam to any position within a field of view; scanning may be continuous, as with galvonometric scanners, or discontinuous, using, for example projecting a beam onto a spinning diffractive structure without departing from the scope of embodiments discussed herein. The optics used to deliver the scanned beam to the subject are discussed in, for example, U.S. Patent Publication No. 2008/0106696 incorporated by reference above, for imaging of the anterior structures of the eye, nominally telecentric scanning focused onto anterior structures, or scanning design to pivot in the pupil of the eye for scanning an imaging of posterior structures.

The spectrographic system images the output of the dispersed interference signal onto a CCD (e.g., Atmel EM2, DALSA Spyder) or CMOS (e.g. Basler Sprint) camera, as is well known in the art. For extended depth imaging with 7 mm single-sided imaging depth, a source with central wavelength of 840 nm and a FWHM bandwidth of 65 nm imaged onto a 4096 element array with 14 µm pixel width may be used. As outlined in the Table of FIG. 17, the edged-to-edge bandwidth of the array is 103 nm, and the source decays to 6 dB of peak power at the edge of the array. The frequency spacing of central pixels is 10.7 GHz. In a traditional spectrometer that utilizes a volume phase holograph transmission grating, there may be significant frequency chirp from the blue edge to the red edge, leading to the need for resampling discussed earlier.

Figure 18A:
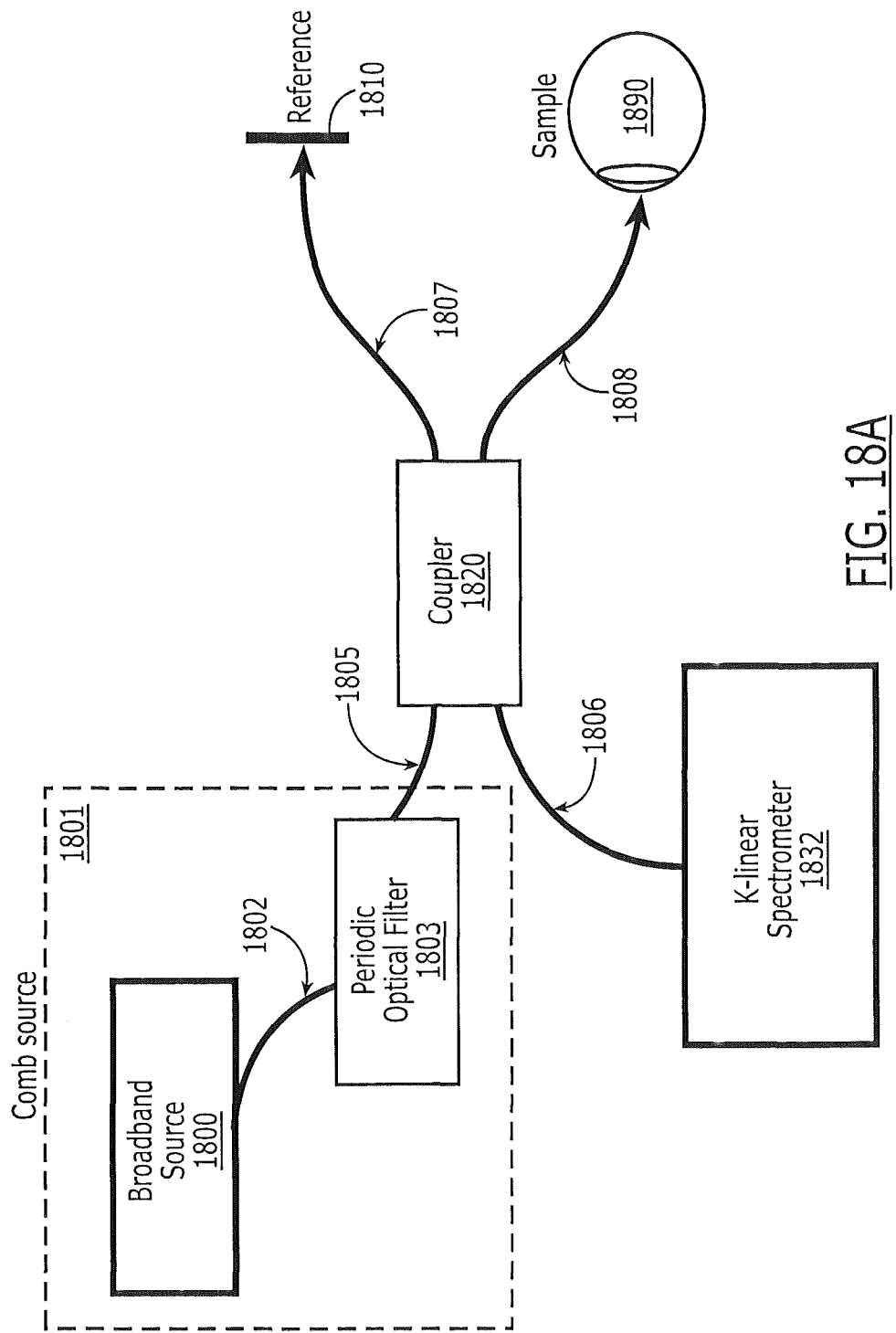
FIGS. 18A through 18C are block diagrams illustrating various embodiments of extended-depth FDOCT imaging systems in accordance with some embodiments of the inventive concept.
Figure 18B:
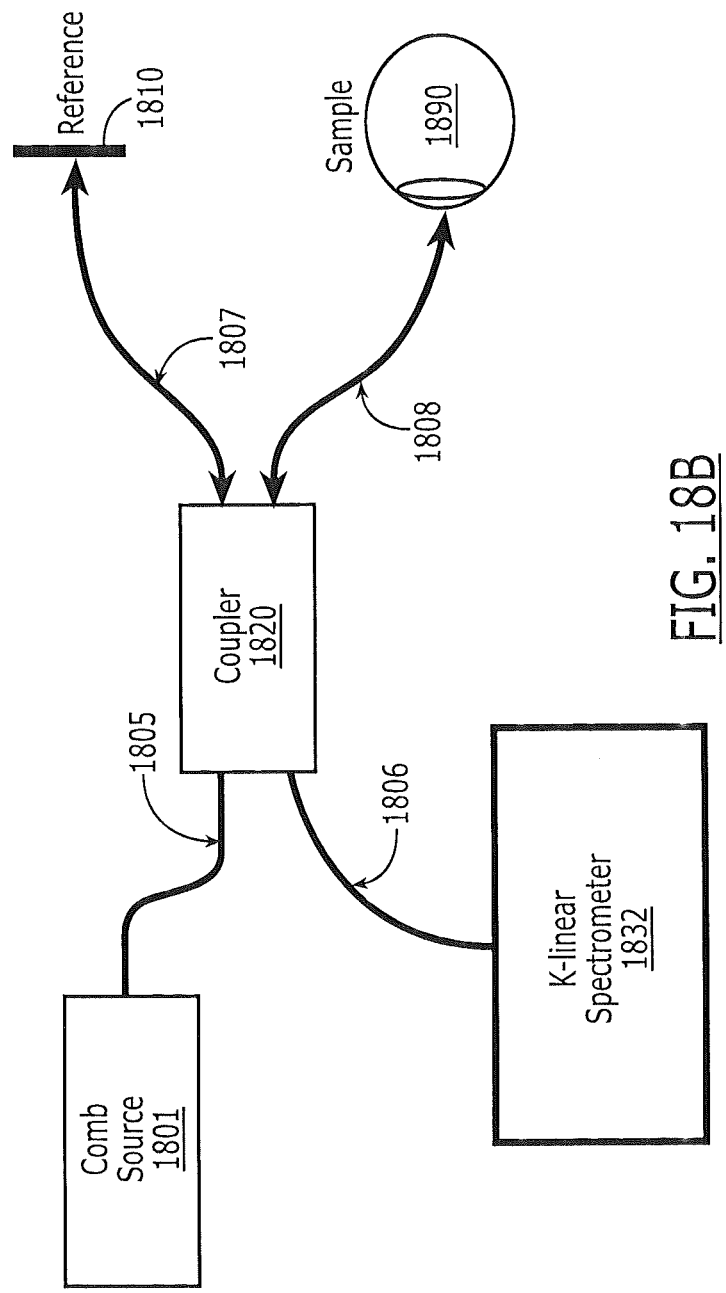
Figure 18C:
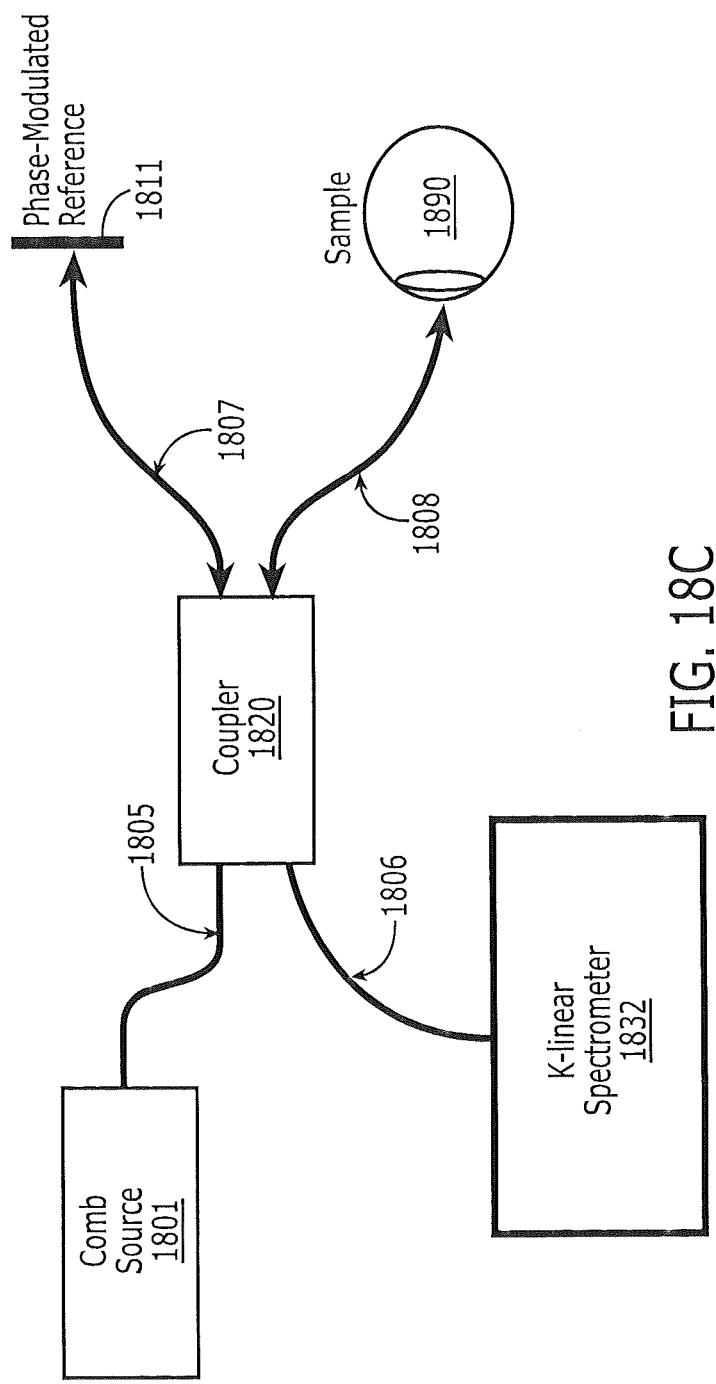

In some embodiments of the present inventive concept, the spectrometer will be of a constant-dispersion, or k-linearized type as illustrated in FIGS. 18A through 18C, k-linear spectrometer 1832. As illustrated in FIGS. 18A-18C, the spectrometer includes a comb source 1801, a reference arm 1810 and a sample arm 1890 coupled to each other by a coupler/beamsplitter 1820. As further illustrated in FIGS. 18A-18C, the beamsplitter 1820 is also coupled to the K-linear Spectrometer over a detection path 1806 that may be provided by an optical fiber. As further illustrated in FIG. 18, the source 1801 is coupled to the beamsplitter 1820 by a source path 1805; the reference arm 1810 is coupled to the beamsplitter 1820 over a reference arm path 1807. Similarly, the sample arm 1890 is coupled to the beamsplitter 1820 over the sample arm path 1808. The source path 1805, the reference arm path 1807 and the sample arm path 1808 may all be provided by optical fiber. It will be understood that this may be performed by replacing the VPH grating with a GRISM—a grating-prism pair discussed above with respect to FIGS. 7-10—or a chirped grating replicating a GRISM as discussed above. In some embodiments, the prism is a high index glass (Schott P-SF68, n=2.0), with a vertex angle of π/8 radians (FIG. 7). The prism is in optical contact with the grating. The grating is a low-spatial frequency grating (400 lines/mm), sandwiched between faces of Schott B-270 (n=1.52). The prism angle of incidence α is 22.5 degrees. A high index prism is typically necessary in order that the total internal reflection condition of the grating is reduced or possibly avoided. An air-spaced prism-grating combination may be used to provide additional design functionality, but is not necessary in all cases. The collimated beam input to the prism may be 25 mm in diameter. The dispersed output from the grating couples to a 100 mm focal system, yielding a <10 micrometer spot size on the pixels across the array. The Nth frequency channel maps to the Nth pixel to within 50% of the pixel width across the array.

As illustrated in FIG. 18A, the comb source 1801 may include a broadband source 1800 and a periodic filter 1803 connected through a path 1802. In some embodiments, the spectrum may be channelized to the spectrometer using the periodic optical filter 1803 illustrated in FIG. 18A. In some embodiments, the filter 1803 may be a fabry-Perot etalon (discussed above) illustrated in FIG. 20, which will be discussed further below. In some embodiments, the filter 1803 may be an AR coated glass block of index 1.55 with FSR of 10.7 GHz and Finesse of two. Operating at angle of π/8 degrees to normal to avoid backreflections into the diode, the thickness of the block is 9.79 mm. To achieve a finesse of 2, the reflectivity of the AR coatings must be 41%. For a finesse of 8, reflectivity is 92.7%, further improving sensitivity falloff, but at the cost of required source power. As the linearity of the spectromter will be calibrated, precision of the central frequency of the etalon as a reference point is not a primary concern. Athermalization may be required not so much to control shifts in the channelized spectrum, but to control changes to FSR. Athermalization techniques are known in the art; the degree of athermalization required is to keep the FSR constant to within 25%. An alternative to an athermalized glass block is to use a piezo controlled cavity; the cavity spacing would increase to 15.2 mm for an air index n=1.

The combination of the k-linear spectrometer and the filtered source bandwidth yields a (single-sided) deep imaging SDOCT system with superior sensitivity falloff characteristics. The addition of phase modulation to the reference arm as discussed in U.S. Pat. No. 7,742,174 or U.S. Patent Publication No. 2008/0002183. In some embodiments, a piezo-driven retrorefelector 1811 as illustrated in FIG. 18C modulates the phase of the reference arm from its nominal position. In principle, the phase of the reference arm can be modulated in steps of π/4 for acquisition multiple phase-stepped acquisitions at a specific A-scan location.

In practice, to continuously modulate the scan; the phase information can be determined by integrating over the π/4 steps using an integrating buckets approach. Note that it may not be necessary for the phase steps to be π/4; π/3, for example, works as well. The optimal number of steps is a function of the level of isolation between the real and the mirror image, and the phase stability of the subject. To the latter point, rapid image acquisition may be preferred. In some embodiments, a CMOS or CCD camera with acquisition speeds of at least 70 kHz are desired. In a four phase-step acquisition, a single A-scan is acquired at 17 kHz, which is suitably fast for real-time display of full range cross sectional images. As cameras are now available at 140 kHz, a target full range line rate of 34 kHz (1000 line frame rate of 34 Hz) is practical.

Note as well that it may not be necessary that that the scanning mirrors remain fixed at a specific A-scan location. Phase modulation and acquisition of sequential A-scans is acceptable so long as the A-scans are optically oversampled at a similar ratio as implied in the per-A-scan acquisition scenario. Thus sinusoidally scanning over π radians at each A-scan and acquiring four samples is functionally equivalent to linearly modulating at a rate of π radians over four sequential 4× oversampled A-scans.

If the amplitude, phase and frequency of the modulation are set as specified in U.S. Pat. No. 7,742,174, then the resulting A-scan should theoretically be completely free of DC, autocorrelation, and complex conjugate artifacts. However, slight deviations from perfection in achieving these parameters may be experienced in any real physical implementation of sinusoidal phase modulation and may lead to a degradation of performance compared to the ideal result in the form of incomplete complex conjugate artifact suppression. Thus, an additional step of applying quadrature projection processing according to FIG. 2 of U.S. Patent Application Publication No. 2008/0170219 may be applied to improve the complex conjugate artifact rejection, at the cost of a small amount of reduced signal to noise ratio. Quadrature projection processing is an algorithmic step which does not require any hardware modification and which reduces the complex conjugate artifact from imperfectly phase modulated SDOCT data by forcing the real and imaginary parts of the recorded A-scan signal to be orthogonal.

Figure 25:
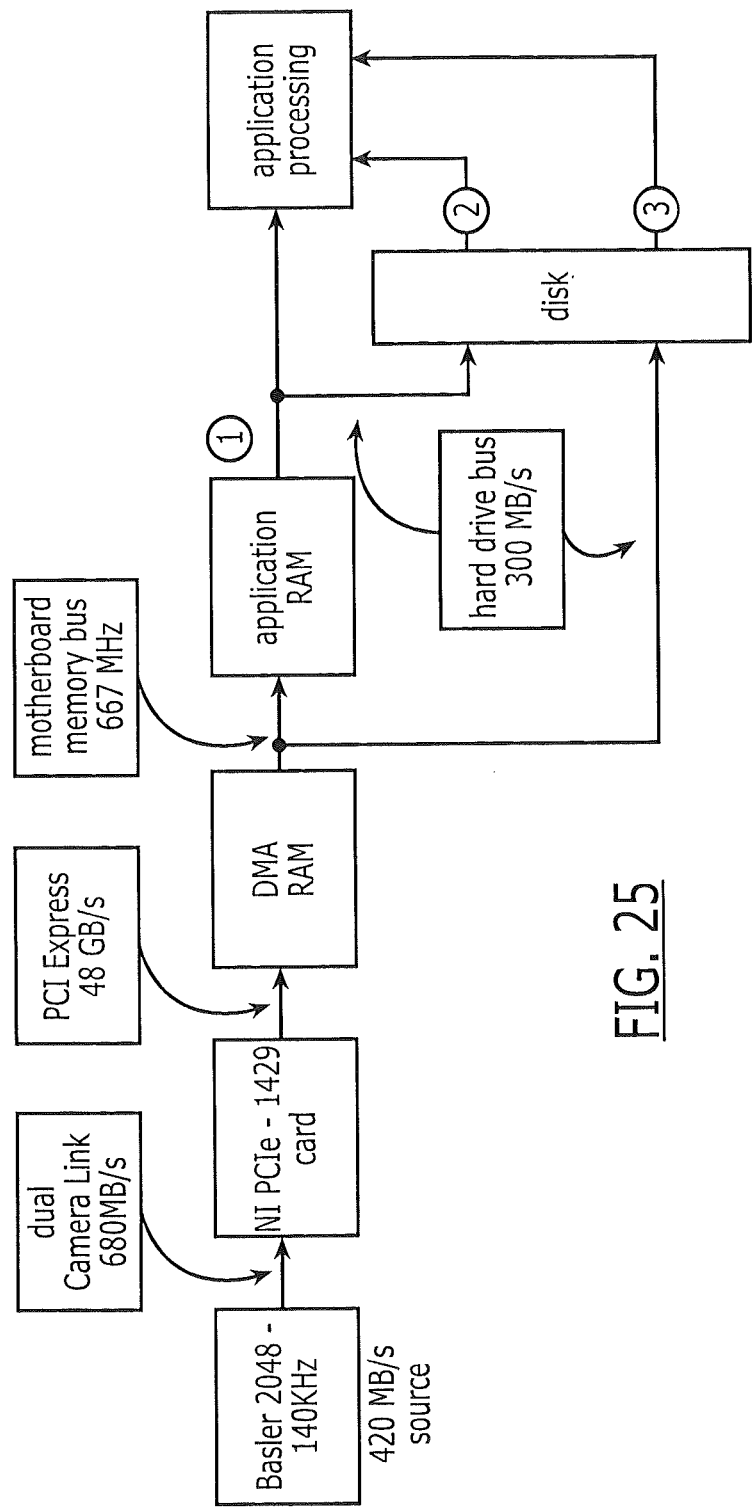
FIG. 25 is a block diagram illustrating data flow of an SDOCT system in accordance with some embodiments.
Figure 26:
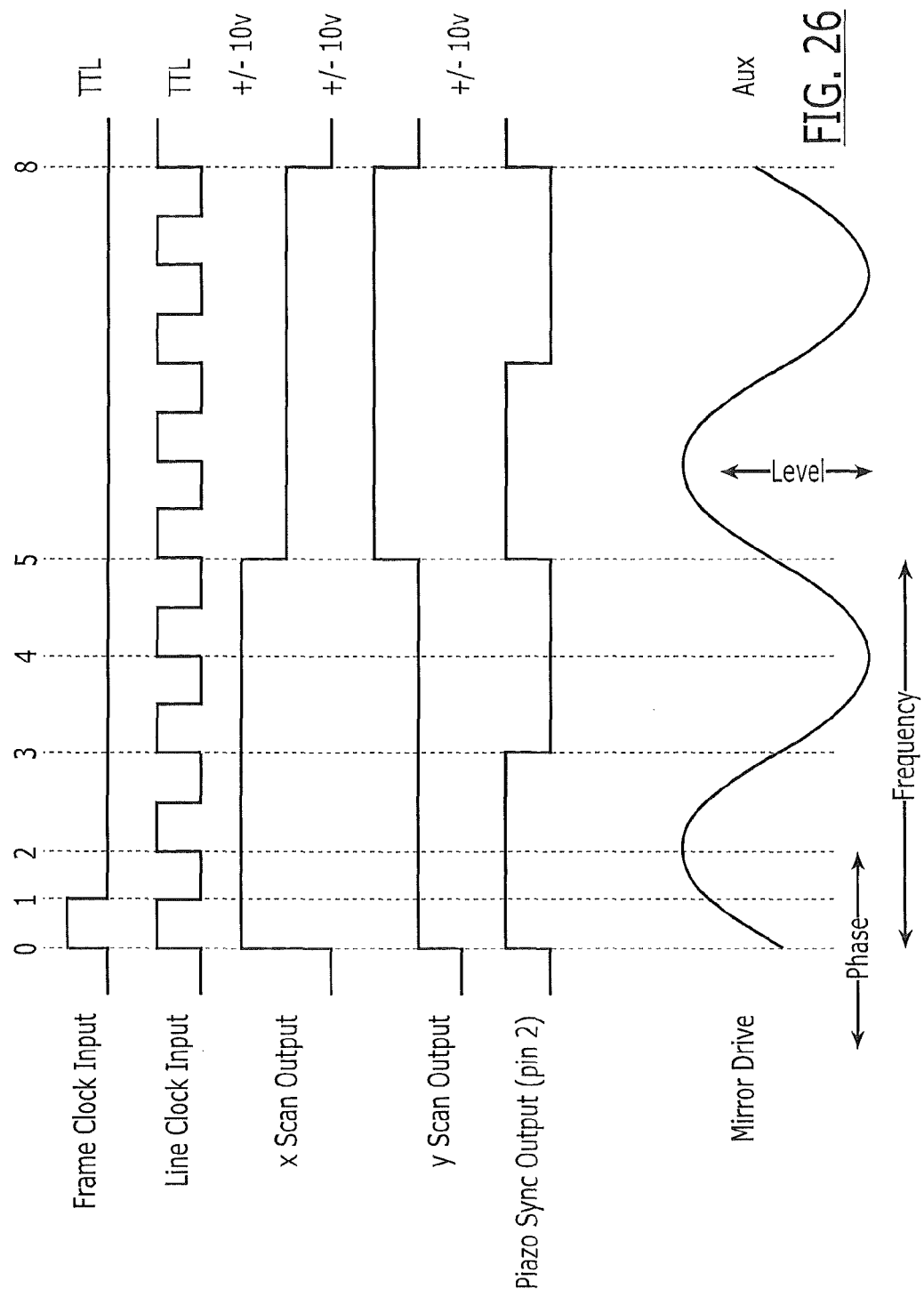
FIG. 26 is a complex conjugate removal (CCR) control timing diagram in accordance with some embodiments.

FIG. 25 is a block diagram illustrating data flow in some embodiments of SDOCT imaging systems in accordance with embodiments discussed herein. As illustrated, the prime bottleneck to stream-to-disk acquisition is not the PCI Bus or motherboard memory bus but the hard drive bus, which is typically limited to 300 MB/s per bus for a SATA drive. FIG. 26 illustrates a CCR control timing diagram. As illustrated therein, every fourth line clock is phase locked to the mirror drive and as such the piezo sync output is locked to the line output.

Figure 19:
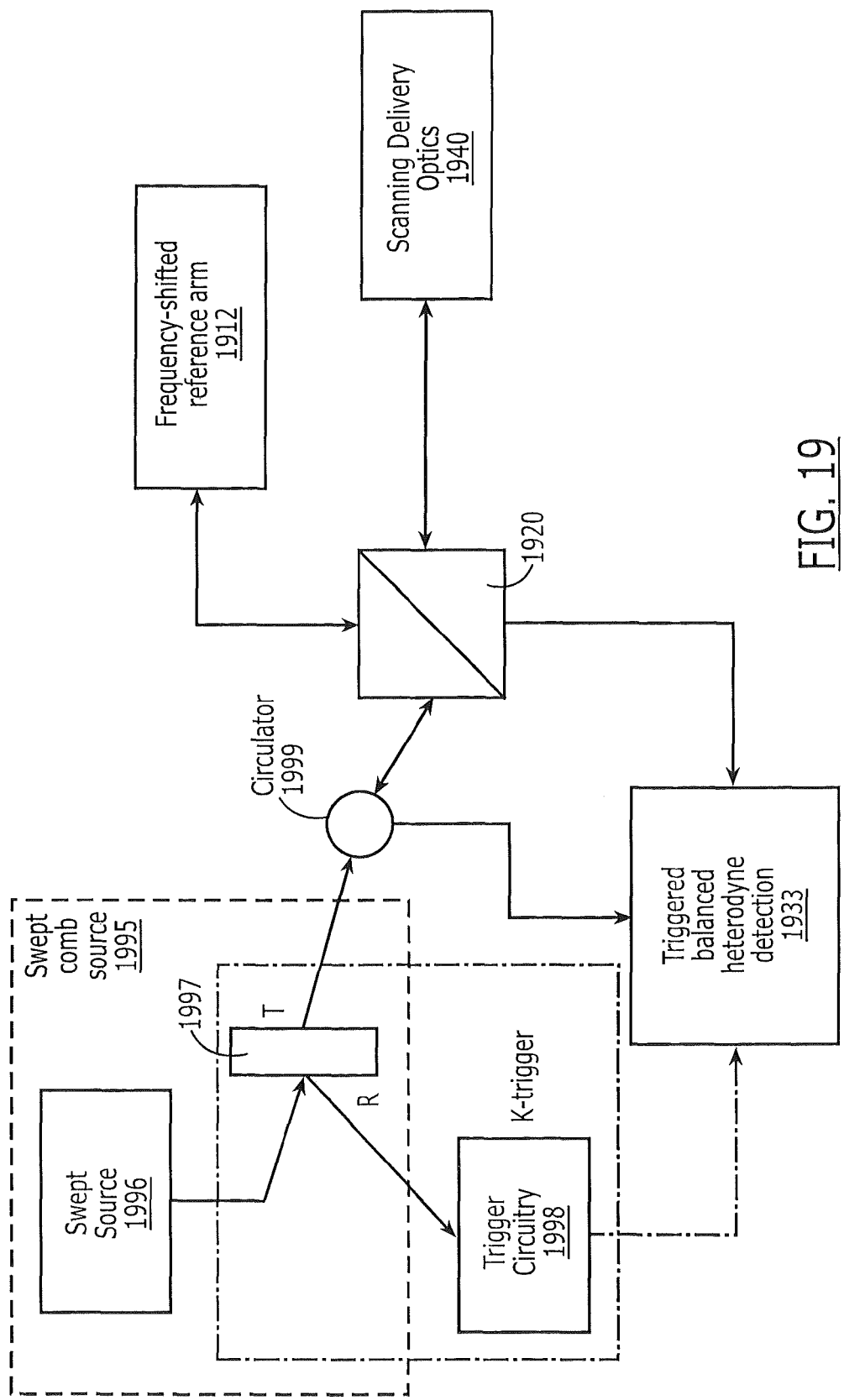
FIG. 19 is a block diagram of an FDOCT system including a swept source and optical filter in accordance with some embodiments.

Referring now to FIG. 19, an SSOCT system designed for comprehensive ocular imaging according to some embodiments of the present inventive concept will be discussed. In some embodiments, complex conjugate removal (CCR) is the so-called "heterodyne" CCR method, which involves introducing a frequency shift between the sample and reference arm light and thus shifting the carrier frequency of the image-bearing signal away from DC, about which the complex conjugate artifact is centered as discussed in U.S. Pat. No. 7,336,366. With the addition of this frequency shift, the A-scan free of complex conjugate artifact is found from the Fourier transform of the detected signal, centered at the frequency shift value. If an A/D converter is used which has much higher bandwidth than the SSOCT signal itself, then the frequency shift value can be set to be many times the frequency encoding the $z_{max}$ value of the A-scan, thus the complex conjugate artifact will be located far in frequency space away from the A-scan data. If a very high sweep speed is employed, however, such that the SSOCT signal already occupies a substantial fraction of the A/D converter bandwidth, then the complex conjugate artifact may only be shifted to the borders of the depth-doubled A-scan. This method of heterodyne CCR is consistent and will not interfere with the embodiments described above for switching between sample and reference arm imaging modes, switching SSOCT imaging depth, and switching of the comb filter FSR spacing to remain consistent with the spectral sampling interval.

As illustrated in FIG. 19, the SSOCT system includes a swept comb source 1995, a circulator 1999, a beamsplitter 1920, a triggered balanced heterodyne detector 1933, a frequency-shifted reference arm 1912 and scanning delivery optics 1940 in the sample arm. As further illustrated in FIG. 19, a fabry-Perot etalon (discussed above) 1997 and a swept source 1996 can be used to provide a swept comb source. A practical etalon may be composed of a glass block with 2 partially reflecting surfaces. As discussed above, the two key attributes of the etalon are the free spectral range (FSR) and the Finesse. The FSR determines the sampling interval, which in some embodiments is designed to match the desired sampling interval, for example, the pixel spacing of the k-linear spectrometer or the k-trigger 1998 of the light source. The FSR is closely related to the optical path length through the etalon, which may be angle tuned according to equation 34. The Finesse sets the spectral width at each output frequency, or the duty cycle of the etalon transmission function. The Finesse is closely related to the reflectivity of the interfaces of the etalon. As further illustrated in FIG. 19, it is further advisable to use an optical isolator or circulator 1999 after the filter and before coupler 1920, as signal returned from sample and reference arm will experience a complementary interaction with etalon, and multi-path interference may degrade image quality.

Figure 20:
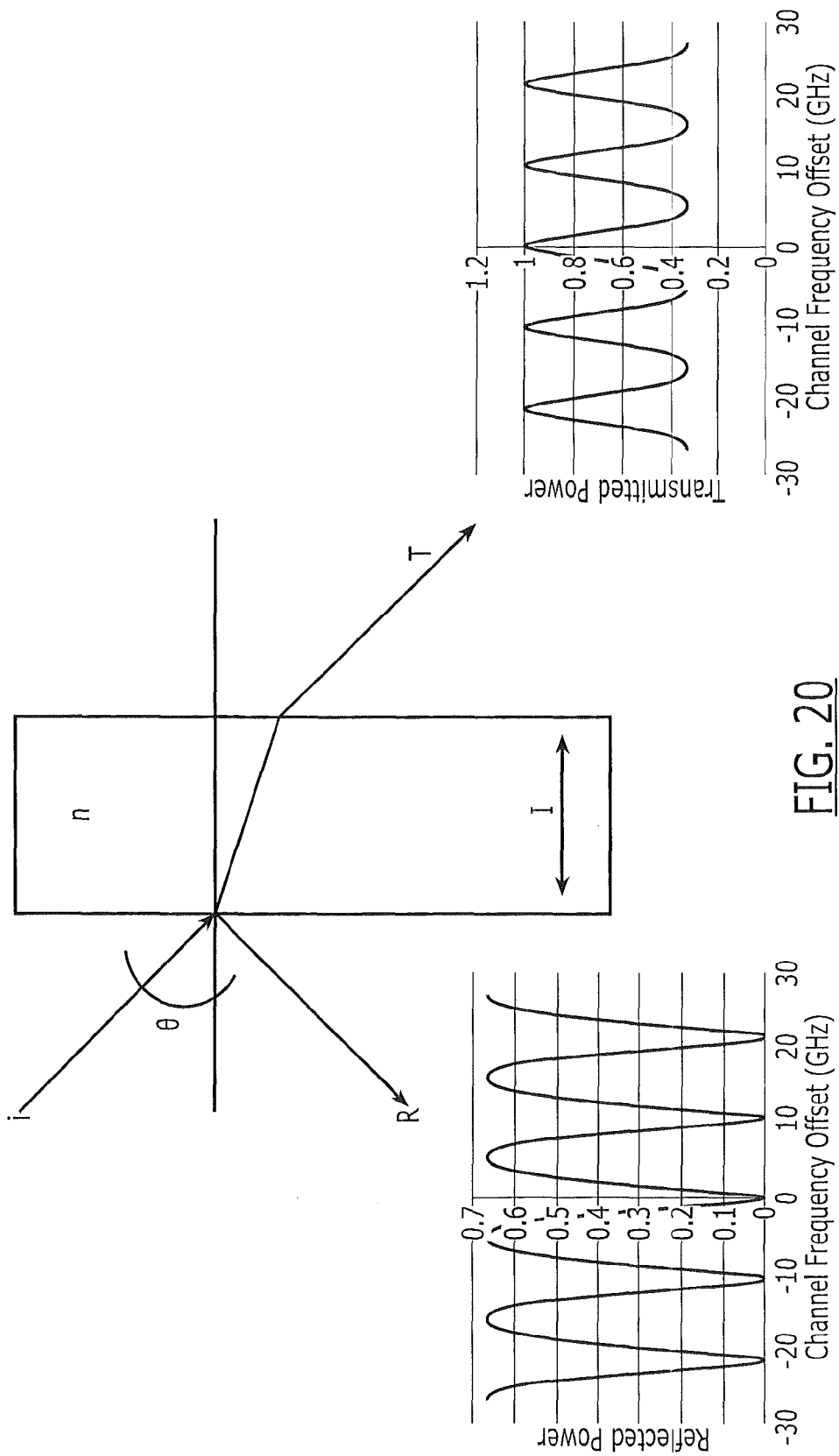
FIG. 20 is a block diagram illustrating an optical filter configuration in accordance with some embodiments.
Figure 21:
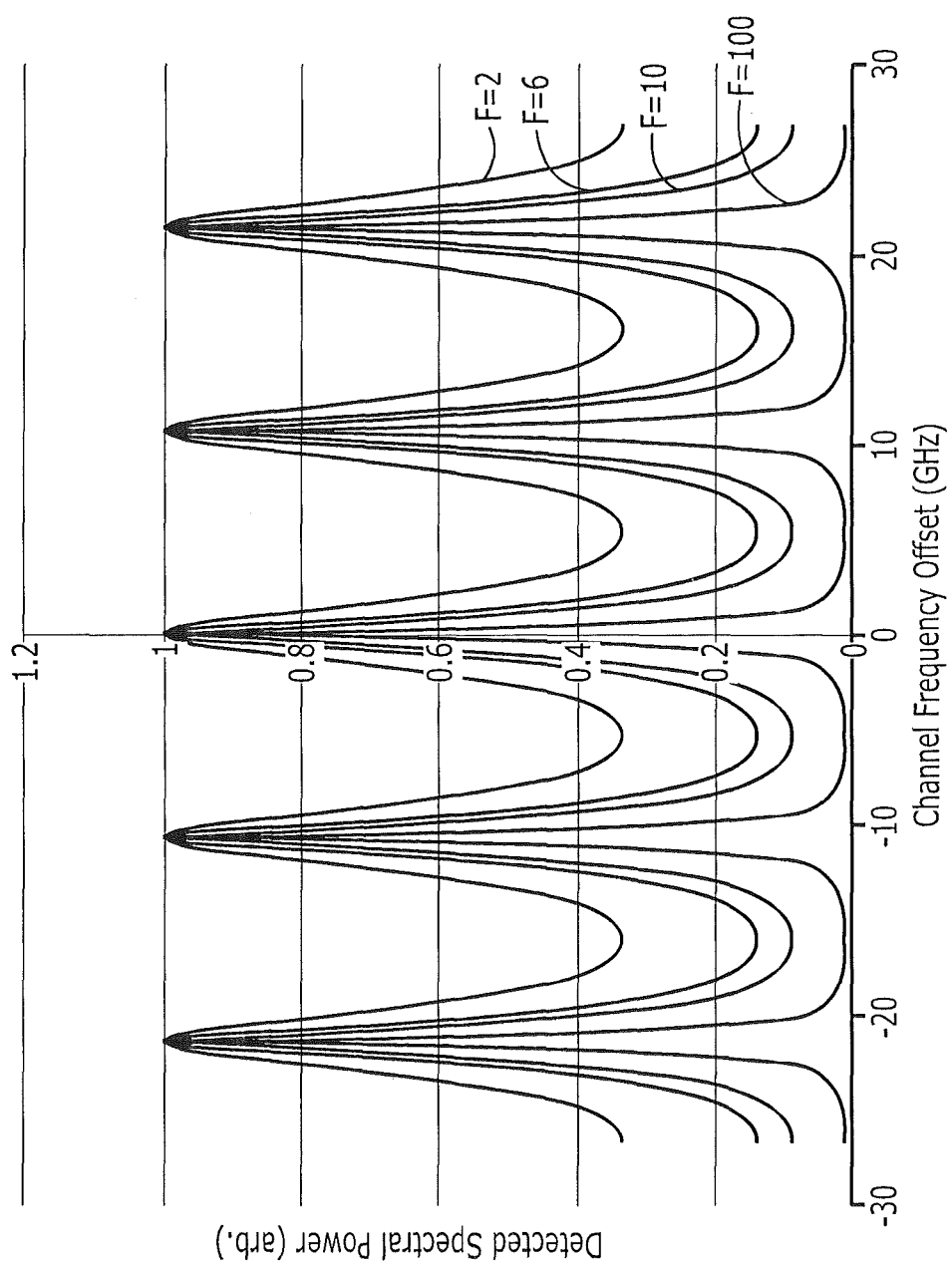
FIGS. 21 through 24 are graphs illustrating various aspects of output of the optical filter of FIG. 20 in accordance with some embodiments.
Figure 22:
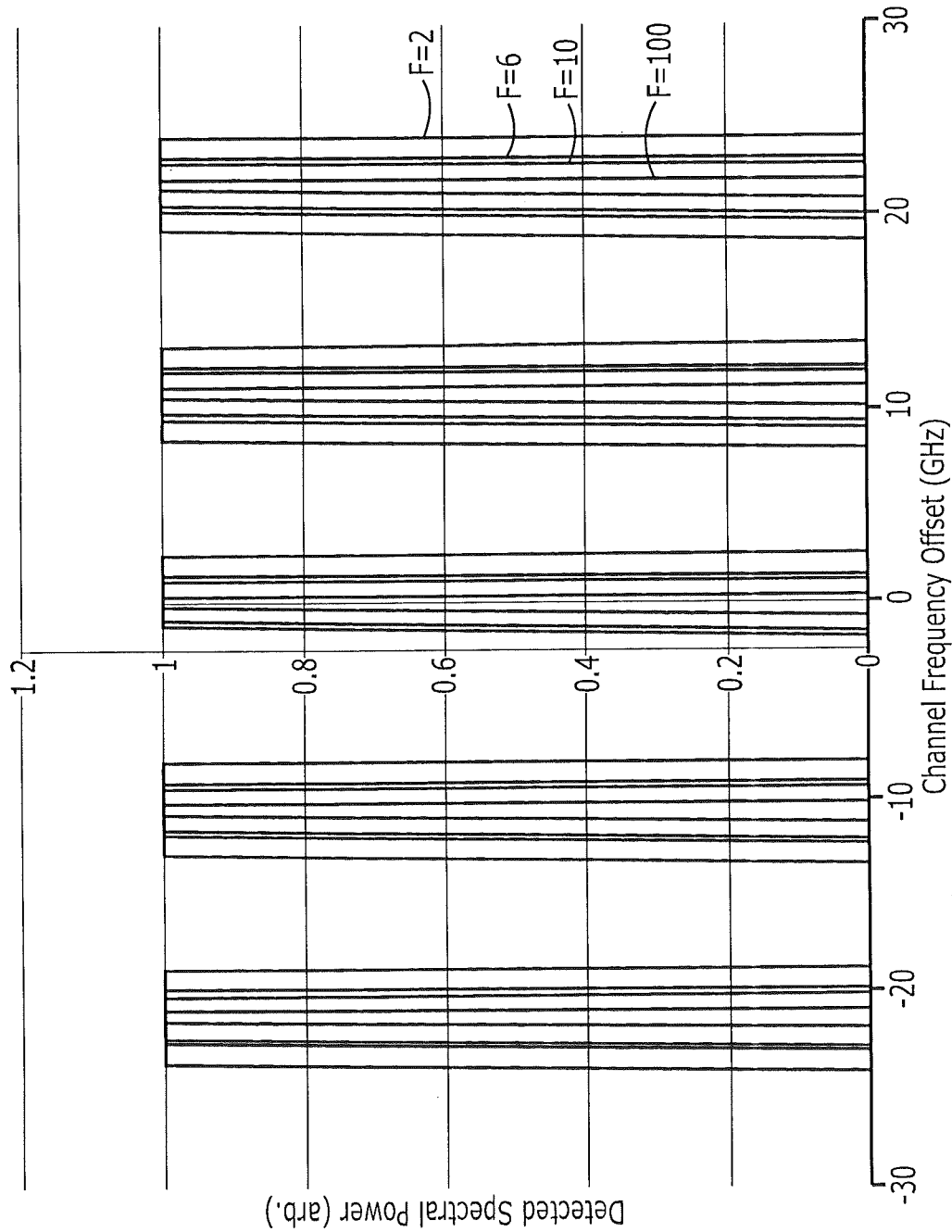

FIG. 20 is a detailed block diagram of the periodic filter 1997 of FIG. 19. Also illustrated in FIG. 20 are graphs of reflected (R) and transmitted (T) power that is output from the filter. FIG. 21 further illustrates a graph depicting the output of the periodic filter of FIG. 20. FIG. 22 is a graph illustrating an effective duty cycle of the periodic optical filter of FIG. 20. FIG. 23 is a graph illustrating SNR falloff as a function of pixel fill factor (duty cycle). As illustrated therein, as the fill factor decreases from 100% down to 50% (Finesse=2), for the 7 mm single-side imaging system discussed herein, the 3 dB falloff depth increases from about 1.34 mm to nearly 2.68 mm. Decreasing further to a 15% fill factor pushes the 3 dB depth beyond the maximum depth. Coupled with CCR, this technique could increase the total imaging range with SNR loss to a full 14 mm range with 1.8 dB SNR loss at the edges for Finesse=6. Finally, FIG. 24 is a graph comparing reflected and transmitted power of the optical filter of FIG. 20.

Some embodiments for a comprehensive ocular imaging system using swept source (SSOCT) design have a $z_{max}=7$ μm, thus the imaging depth capability of this system after complex conjugate removal is 14 mm optical path length. As illustrated in FIG. 19, for a swept source implementation, the light source may be a swept source laser 1996 having a center wavelength near 1060 nm, an instantaneous coherence length (before filtering) of 5 mm, and a full-scanning optical bandwidth of approximately 100 nm. Light from the laser is directed into a 50:50 single mode coupler 1920 and then into sample and reference arms.

As in the SDOCT implementation, the reference path directs light from the coupler to an optical reflector 1912 that is designed to match the path length to the region of interest for the sample under test. Positioning capabilities of the SSOCT reference arm are the same as for the SDOCT reference arm. However, in some embodiments, rather than the phase modulator of the SDOCT configuration, the SSOCT configuration possesses an acousto-optic modulator (AOM) operating at 250 MHz acoustic frequency for heterodyne complex conjugate artifact removal. The sample arm may also possess an AOM operating at 250 MHZ plus a differential frequency, as discussed in U.S. Pat. No. 7,336,366.

Light returning from the sample and reference arms is recombined in the 2×2 coupler and detected by a 500 MHz bandwidth optical photoreceiver. A/D conversion is performed with 12 bit resolution at 500 MHz sampling rate in order to obtain $2*z_{max}=14$ mm optical path length.

Previously demonstrated implementations of heterodyne complex-conjugate removal in SSOCT systems utilized a pair of phase modulators (either acousto-optic or electro-optic) arranged to give a net difference phase modulation frequency on the order of hundreds of kHz to tens of MHz. This was done with either one modulator placed in each of the reference and sample arms, or two modulators arranged in series in a single arm. With source sweep frequencies of less than about 20 kHz, this arrangement gives a sufficiently high heterodyne modulation frequency to allow for good separation of the complex-resolved A-scan signal away from DC. With an increased sweep rate of approximately 100 kHz, a single acousto-optic or electro-optic modulator operating at approximately 350-500 MHz modulation frequency may be placed in the reference arm, as illustrated in FIG. 19. If the photoreceiver and A/D conversion circuitry have a bandwidth of 700-1000 MHz, then the frequency modulation will place the zero path length position of the A-scan near the middle of the detection bandwidth, thus effectively resolving the complex conjugate artifact for these rapid scan rates.

The same periodic filter structure described for the SDOCT system is applied to the SSOCT to increase the instantaneous coherence length of the source (by reducing the sampled linewidth). A variable length piezo-driven etalon may be used in order that the frequency spacing of the output peaks may be changed to change the single-sided depth of the image. At 10.71 GHz, a 7 mm single-sided window imaging window may be achieved. The number of samples acquired determines the wavelength range utilized, and thus enables a tradeoff between resolution and acquisition speed. At 2048 samples, the sampled wavelength range will be 82 nm, and the resolution will be approximately 10 μm. The reflective port of the periodic filter acts directly as the k-trigger for sampling the interference signature. As the etalon FSR is modified, for example from 10.7 GHz to 5.35 GHz, the single-sided imaging depth is increased from 7 mm to 14 mm. The k-trigger automatically tracks. This capability to change imaging depth is an important attribute of this SSOCT architecture, allowing an imaging system to rapidly change depth of imaging field as the situation requires.

For SDOCT, one can imagine a hardware switchable spectrometer wherein the sampling interval is modified. A simple approach to reduce image depth is to process every second pixel on an array. In some embodiments, a spectrometer can be constructed to double the imaging depth.

Further embodiments of the present inventive concept will now be discussed with respect to FIGS. 27 through 41. In particular, various details optics will be discussed for comprehensive ocular FDOCT. As discussed above, some embodiments discussed herein are related to comprehensive volumetric imaging of all ocular structures along the visual axis using FDOCT. As further discussed above, current-generation FDOCT systems, including spectral-domain (SDOCT) and swept-source (SSOCT) implementations, are in routine clinical use for diagnosis of retinal pathologies. FDOCT systems have also been applied for imaging of the anterior segment of the eye. As used herein, the "anterior segment of the eye" refers to the region of the eye from the posterior surface of the crystalline lens to the apex of the cornea. Thus, the "anterior segment of the eye" refers to all ocular structures located anterior to the vitreous humor (including cornea, aqueous humor, iris, ciliary body, and crystalline lens). As used herein, the "posterior segment of the eye" refers to the vitreous from the posterior surface of the crystalline lens up to and including the retina, choroid, and optic nerve. Thus, the "posterior segment of the eye" refers to the internal ocular structures which are located posterior to the anterior segment, including the vitreous humor, retina, and choroid. Conventional optical designs for scanning the anterior segment and retina are illustrated in FIGS. 27A through 27C.

Figure 27A:
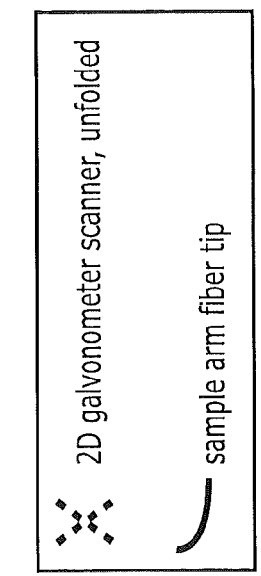
FIGS. 27A through 27C illustrate diagrams in accordance with convention anterior segment and retinal OCT sample arm scanning.
Figure 27B:
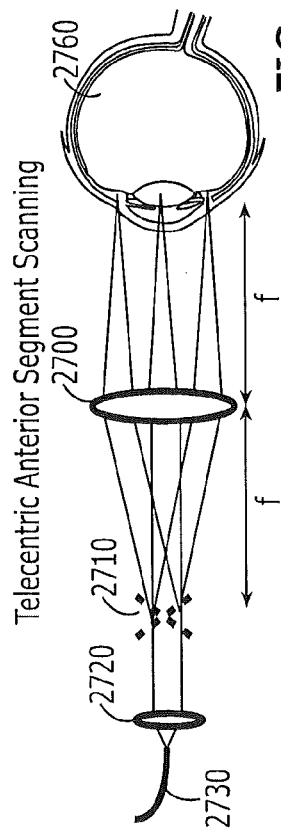
Figure 27C:
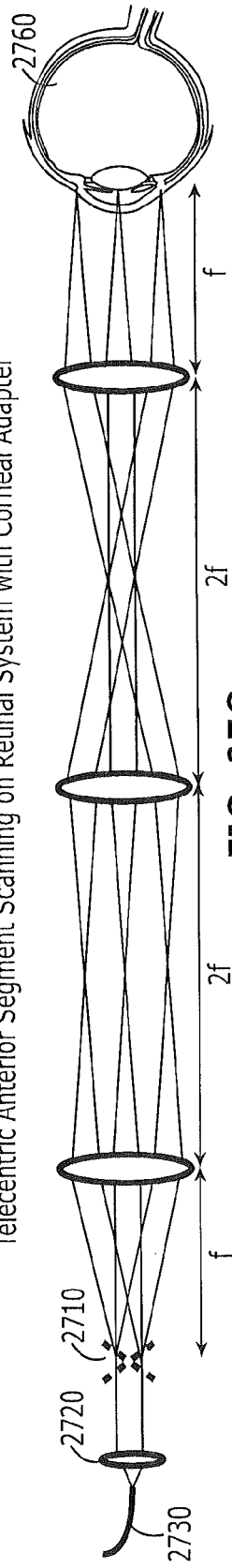

In particular, FIG. 27A illustrates a system for imaging the anterior segment of the eye 2760. As illustrated, the system includes a collimator 2700, a two-dimensional galvanometer scanner 2710, and a single scan lens 2720 in a telecentric configuration. As used herein, "telecentric" or "telecentricity" refers to scanning a beam such that the rays of the beam are parallel to an optical axis of the system. As further illustrated in FIG. 27, the single scan lens 2720 is coupled to the sample arm fiber tip 2730. FIG. 27B illustrates a conventional system for retinal scanning with an iris pivot including an additional lens 2701. FIG. 27C illustrates a conventional telecentric anterior segment system including a corneal adapter. As used herein, the "collimated" refers to a non-diverging, spatially coherent beam. In other words, "collimated" refers to a parallel beam (i.e., neither converging nor diverging).

FDOCT is useful for examination of the anterior segment of the eye, diagnosis of corneal, iris, and lens pathologies as well as for quantitative biometry of the anterior segment including measurements of corneal refractive power, corneal thickness, anterior chamber depth, lens optical power, and lens thickness. These parameters resulting from anterior segment biometry, with the addition of eye length measurement, are needed for calculation of intraocular lens implant power for cataract surgery. Current methods for evaluation of these parameters are limited to measurement along a single axis, and thus provide only central values for these parameters which may not accurately account for off-axis variations and aberrations. With the ability to rapidly acquire densely sampled 2D images and 3D volumes of information, FDOCT offers the potential to perform substantially improved characterization of the refractive properties of the entire eye, if calibrated, and correlated volumetric images of the anterior segment, lens, and retina could be acquired either simultaneously or in rapid succession in the same patient. Current-generation FDOCT instruments, however, are not capable of imaging with sufficient depth field of view to record data from all of these structures with the same instrument without time-consuming interchange of optics and of the reference arm length.

Accordingly, as will be discussed below with respect to FIG. 28 through 41, some embodiments of the present inventive concept provide an FDOCT system capable of simultaneous imaging of the anterior segment, lens, and retina or of rapidly switching between such modes during a rapid acquisition sequence, which preserves their relative displacements in order to perform comprehensive volumetric imaging of all ocular structures along the visual axis. In some embodiments, switching between modes is rapid, i.e., on the time scale of a few A-scans acquisition time, for example, a few milliseconds, and should allow for the maximum possible re-use of optics and mechanics in both modes to reduce total system cost and complexity.

Some embodiments of the present inventive concept configured to perform rapid switching between imaging in the anterior segment (including the cornea, acqueous humor, iris, ciliary body, and lens) and retina in FDOCT systems will be discussed. As a preliminary note, embodiments discussed with respect to FIGS. 28A-30B represent optical designs of patient ocular scanners which are configured to be placed in the sample arm of FDOCT, SDOCT, or SSOCT systems. In the illustrated embodiments, all lenses are assumed for clarity to have focal length f and to be placed distances apart as indicated. However one of skill in the art of optical design would understand that other focal lengths of some lenses could also be used, with accompanying effects of magnification or de-magnification of the scan patterns and resulting spot sizes, without departing from the scope of embodiments discussed herein. Furthermore, in the figures, galvanometer scanners are illustrated in a compact format which is known to those familiar with the art of scanning system design. Two-dimensional galvanometers are shown as crossed dashed lines, denoting that they scan in two dimensions. This may be accomplished with a single mirror which is capable of being pivoted in two orthogonal directions, or with two separate one-dimensional galvonometers, each capable of being pivoted in orthogonal directions which are either place in close proximity (i.e., less than about 10 mm apart), or else having an optical sub-system placed between them whose purpose it is to relay an image of one mirror onto the other one. In addition, the galvanometers are also drawn in an unfolded manner so that the light beams incident upon them in their undeviated or "central" position are shown as passing straight through rather than being reflected, and light beams which are deflected in either one direction from this central position are shown either above or below the undeviated beams.

Referring first to FIG. 28A, a system for imaging of the anterior segment includes a collimator 2800, a two-dimensional galvanometer scanner 2810, and a single scan lens 2820 in a telecentric configuration. As further illustrated the scan lens is connected to the sample arm fiber tip. In the configuration illustrated in FIG. 28A, two dimensional and three dimensional imaging of the entire anterior segment may be performed. To switch the system of FIG. 28A to a system for retinal imaging, a single additional lens 2822 as illustrated in FIG. 28B, also with focal length f, is rapidly translated into the optical path either immediately proximal or immediately distal to the collimating lens. This lens changes the sample arm beam from collimated to focusing on the 2D galvanometer scanner. As used herein, "focusing" refers to refracting or steering a beam of light to converge at the focal position of the focusing element. In other words, "focusing" refers to a beam in which the rays are converging to a common focal point. With the scanner in its home position, the focused beam expands until it is collimated by the scan lens and then is re-focused by the cornea and lens of the patient onto the patient's retina. In this position, FDOCT A-scans of the patient's retina may be acquired for measurement of the retinal position and axial reflectivity properties. Scanning of the galvanometer away from its central position results in translation of the collimated beam away from the pupil center, where it will eventually be clipped by the edge of the pupil. Thus, extensive lateral imaging of the retina may not be available in accordance with embodiments illustrated in FIGS. 28A and 28B.

As illustrated in FIG. 42, rapid insertion of the additional lens as discussed with respect to 28B for mode switching may be performed by mounting the lens or a sequence of identical lenses into a plate 4281, for example, alternating around the circumference of the plate with the absence of a lens, which is then rapidly rotated into position by use of a stepper or DC motor and suitable controller. In other words, the controller 4291 is configured to cause the mechanical means 4280, for example, a stepper or DC motor, to rapidly rotate the plate 4281. The plate 4281 includes both lenses 4280 and empty windows 4285, such that as the plate 4281 is rotated, the system changes modes. It will be understood that embodiments are not limited to this configuration. For example, means for insertion of the lens could include mounting the lens in an arm attached to a rotary solenoid which could be rapidly rotated into and out of position without departing from the scope of the present inventive concept.

Since the two dimensional optical scanner in these embodiments need only deviate a collimated or focused beam, the scanner clear aperture need only be as large as the collimated beam size. In conventional systems, this collimated beam size may be less than about 5.0 mm, which enables the use of compact and high-speed galvanometer scanners.

It will be understood that switching between the anterior segment and retinal imaging modes as discussed with respect to FIGS. 28A and 28B also involves changing the optical path length from the sample arm fiber tip to the sample being imaged. Thus, changing of modes will also require simultaneous re-setting of the reference arm position in common FDOCT engine designs, which requires matching of optical path length between the sample and reference arms which will be discussed further below.

Figure 29A:
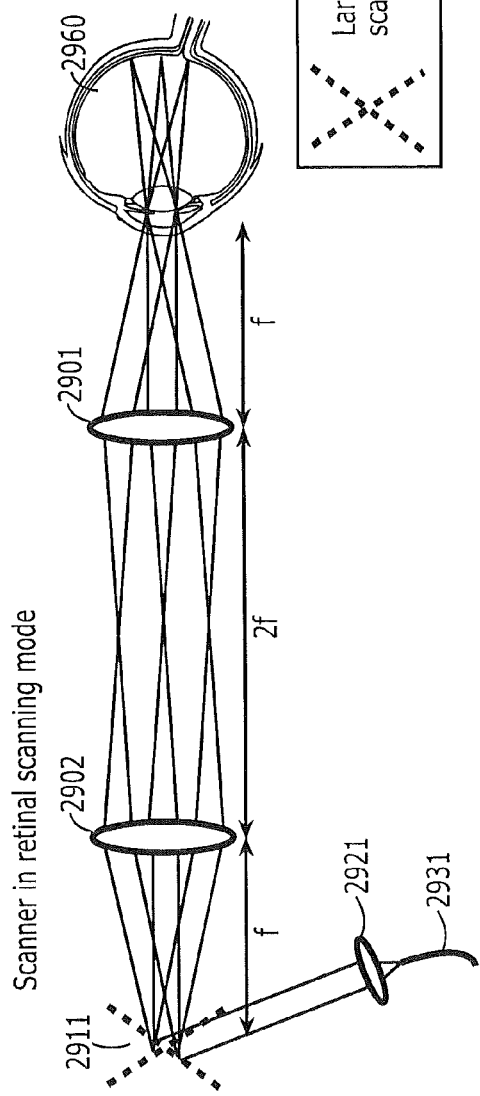
FIGS. 29A and 29B illustrate switchable anterior-retinal scanning systems in accordance with some embodiments.
Figure 29B:
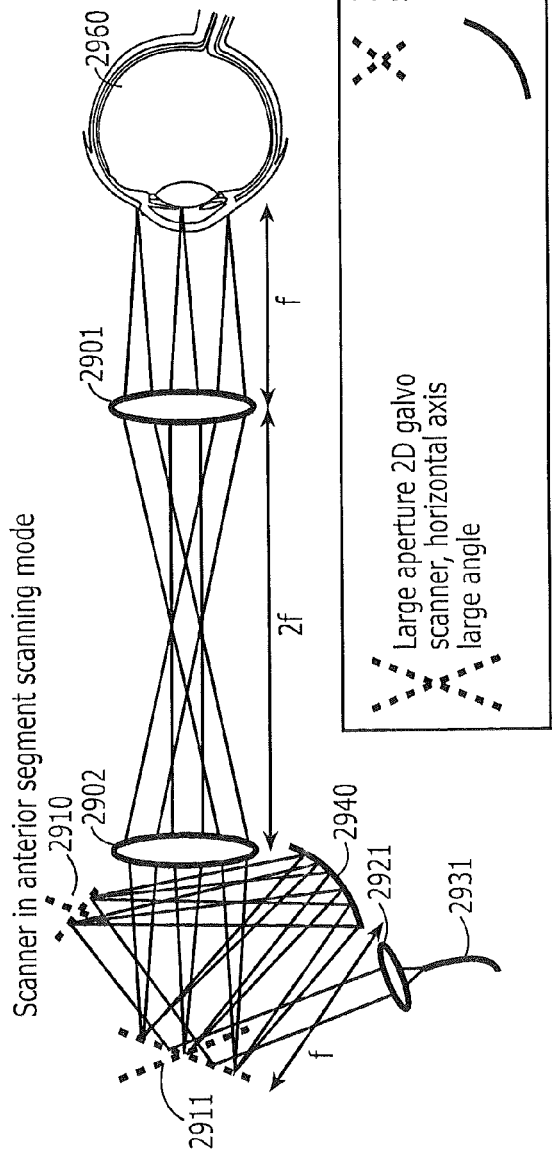

Referring now to FIGS. 29A and 29B, the system illustrated therein is configured for full two dimensional imaging of both the retina and structures of the anterior segment. The retinal imaging system includes a collimating lens 2921, two two-dimensional galvanometer scanner pairs 2910 and 2911, a scan lens 2902, and an objective lens 2901 placed as illustrated in FIGS. 29A and 29B. Those having skill in the art of optical design will realize that lenses with other focal lengths could be used to magnify or de-magnify the scan range and spot size on the patient's retina and the working distance between the objective lens and the patient's eye. The difference between this design discussed with respect to FIGS. 28A and 28B is that the first three-dimensional scanner requires both a large clear aperture and a large angular deviation to switch between modes rather than insertion of an additional lens. The size requirement for the first two-dimensional scanner is that the aperture be as large as the desired scan range on the anterior segment (or suitably related to it if magnifying or de-magnifying optics are used in the telescope comprising the scan lens and objective lens following the scanner), and that the scanner have sufficient angular excursion to allow for switching to the anterior segment imaging mode by adjusting the correct angle required to hit the second two-dimensional scanner pair. With the first scanner pair in this highly deviated position, the second two-dimensional scanner pair is used to image the retina with small angular excursions of the second galvanometer scanners performing two-dimensional scanning of the focused sample arm beam on the patient's retina. As illustrated in FIG. 29B, the second two-dimensional optical scanner pair 2911 directs the re-directed collimated light in a triangular pattern towards a curved mirror 2940 placed on focal length f away from the large aperture original two dimensional scanner mirror pair. This alternative optical path effectively transforms the scanning beam into a state such that the remaining optics along the optical path comprise a telescope which images the scanning focused beam into the anterior segment of the patient's eye. Alternative embodiments of this alternative triangular optical path may also be constructed along similar lines, for example using a lens and flat mirror instead of a curved mirror, or using multiple curved mirrors in combination in order to reduce astigmatism.

In embodiments illustrated in FIGS. 29A and 29B, the optical path length of the optical system is longer in the anterior segment as compared to the retinal imaging mode. If properly designed, this path length difference could be designed to match the optical path length difference anticipated upon traversing the length of a standard human eye, including the index of refraction of the acqueous and vitreous humor. If done, this may eliminate the need for reference path length switching when switching modes.

Further embodiments of systems configured to image both the retina and the anterior segment of the eye 3060 will now be discussed with respect to FIGS. 30A and 30B. As illustrated, the imaging system includes a collimating lens 3021, two two-dimensional, a scan lens 3002, and an objective lens 3001 placed as illustrated in FIGS. 29A and 29B. As further illustrated in FIGS. 30A and 30B, embodiments illustrated in FIGS. 30A and 30B use a single two-dimensional scanner pair 3011 having a large clear aperture and angular scan capability, and a flat mirror 3041 in place of the second two-dimensional scanner pair discussed above with respect to embodiments illustrated in FIGS. 29A and 29B. For two-dimensional scanning of the retina, the collimated beam entering the sample arm is incident on the two-dimensional scanner 3011, which is imaged into the pupil plane of the patient by a 4f or equivalent telescope. Small angular deviations around the two-dimensional scanner center position are imaged by the telescope into the patent's pupil plane. The patient's own cornea and lens act to focus this beam on the retina in a scanning pattern.

To switch to anterior segment imaging illustrated in FIG. 30B, the two-dimensional scanner pair 3011 is deviated by a large amount in order to direct the incident collimated beam into a separate path consisting of a flat mirror 3041 and a concave mirror 3040 with focal length f, the latter positioned a distance f from the two dimensional scanner 3011. Small deviations of the two-dimensional scanner about this large offset deviation now act to scan a focused beam across the surface of the two-dimensional scanner, which the 4f telescope then images onto the anterior segment of the patient's eye. If the 4f telescope is designed for 1:1 imaging, then the clear aperture of the two-dimensional scanner must match the distance desired to be scanned on the patient's anterior segment. However, the telescope between the two-dimensional scanner pair and the eye may be alternatively designed to incorporate magnification or demagnification as desired, albeit at the cost of additional scan angle requirements on the two-dimensional scanner.

Figure 31:
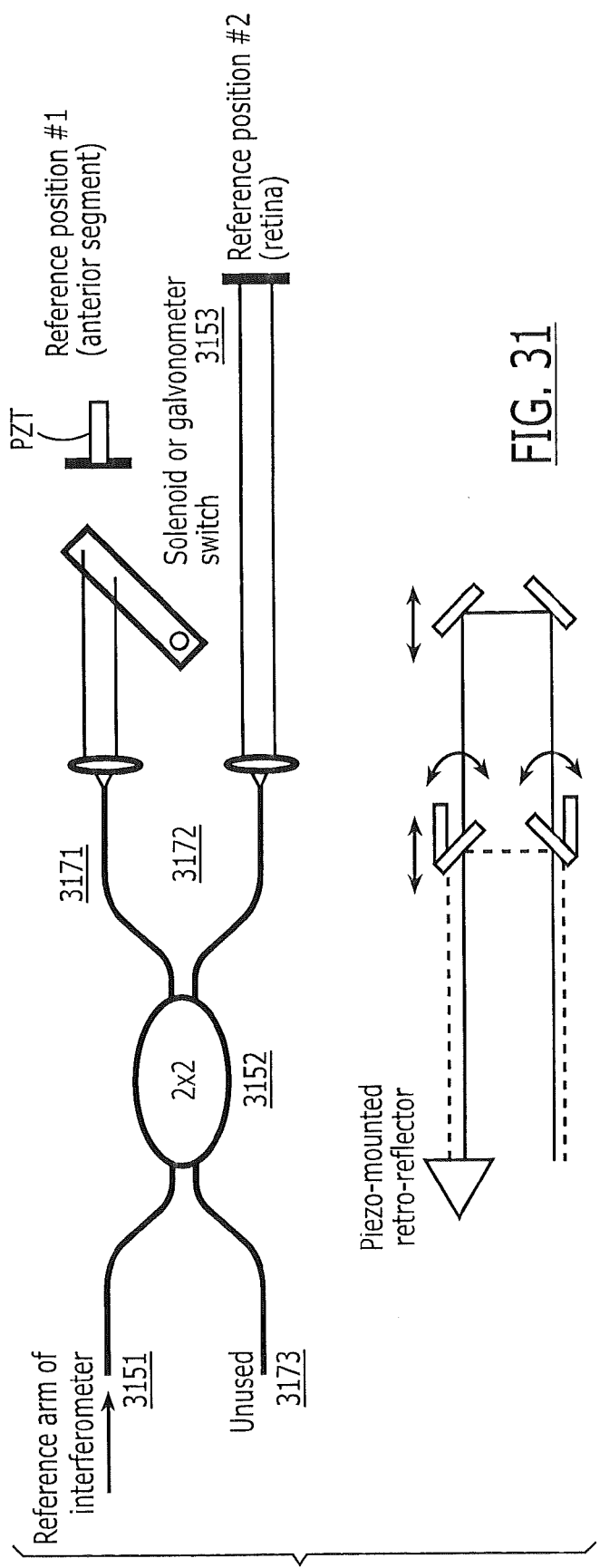
FIG. 31 is a diagram illustrating a rapidly switching reference delay in accordance with embodiments illustrated in FIGS. 28A through 30B.

Referring now to FIG. 31, a dual switchable reference delay for dual depth imaging regions will be discussed. In the embodiments discussed above with respect to FIGS. 28A through 30B for switching between anterior segment and retinal imaging, there is a need for equally rapid switching of the FDOCT reference delay simultaneous with sample arm optics mode switching. Some embodiments for rapid switching are illustrated in FIG. 31. As illustrated therein, light from the reference arm of the interferometer 3151 is split into two or more separate paths using, for example, a fiber coupler 3152. The coupler is illustrated in FIG. 31 as a 2×2 coupler, however, it will be understood that higher order couplers could also be used for rapid switching between more than 2 reference delays (paths). In each delay arm 3171, 3172, a desired optical delay matching one of the modes of the sample arm scanner may be pre-set. To switch between reference delays, a rapid mechanical switch 3153 may be used to block all but the desired reference delay. In some embodiments, the mechanical switch could be an arm mounted to a rotary solenoid, a wheel with cutouts (akin to a chopper wheel) mounted to a stepper or DC motor, or any other rapid mechanical switch familiar to those familiar with the art of mechanical design without departing from the scope of the inventive concept.

Figure 32:
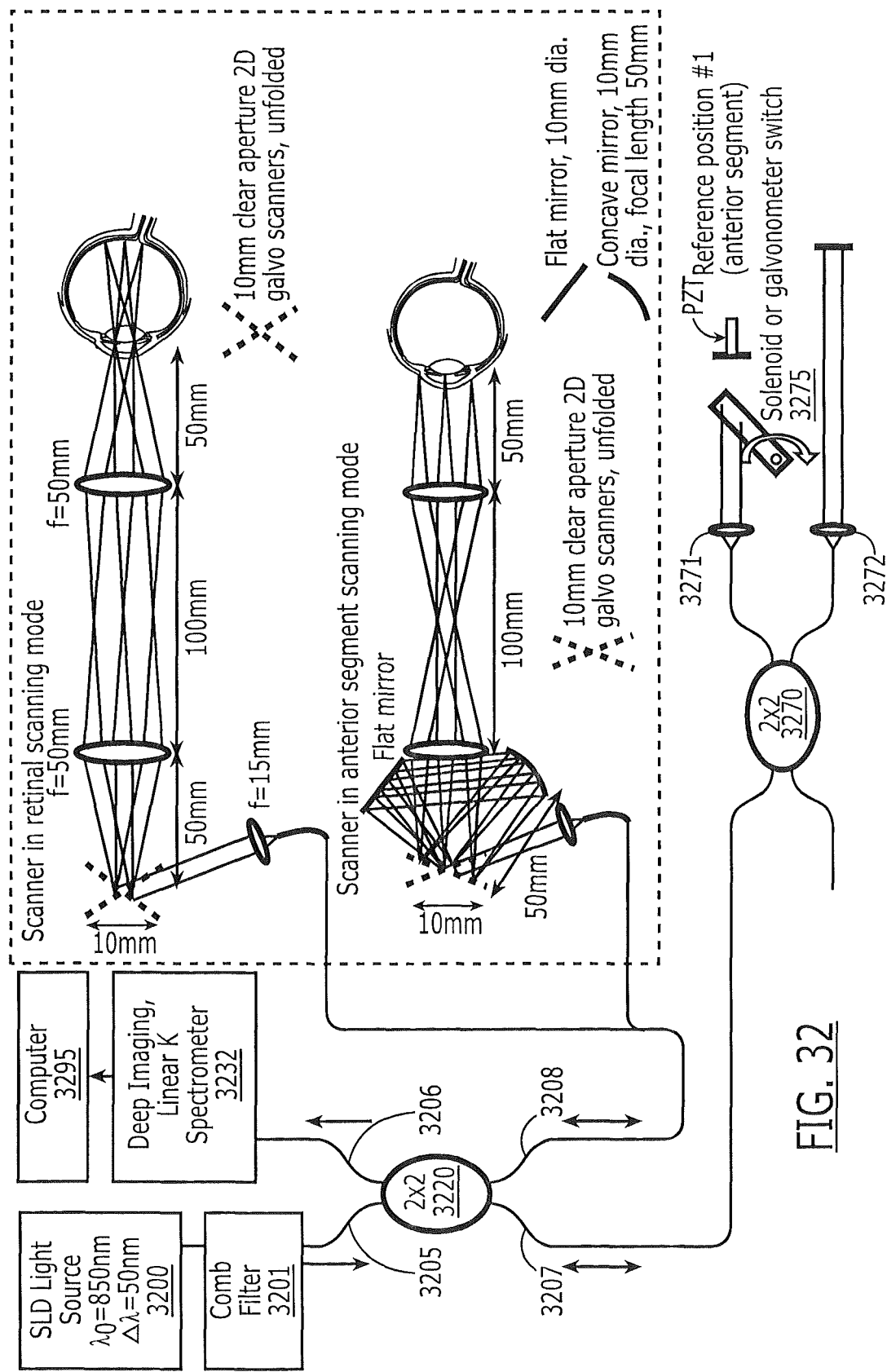
FIG. 32 is a block diagram illustrating a comprehensive Ocular Spectral Domain OCT imaging system in accordance with some embodiments.

Referring now to FIG. 32, a system for ocular spectral Domain OCT imaging will be discussed. As illustrated therein, the spectral domain OCT system includes a broadband optical source 3200, a comb filter 3201, a source path 3205, a beam splitter/combiner 3220, a reference path 3207, a sample path 3208 with a scanning system and focal optics illustrated in FIGS. 30A and 30B configured to appropriately to image structures of the sample, such as the cornea, anterior chamber, iris, lens, posterior chamber, and retina of the eye, a detector path 3206. The detector path 3206 includes a computer 3295 and a deep imaging, linear K Spectrometer 3232. As illustrated, the broadband source 3200 in FIG. 32 includes and SLD light source having a $\lambda_o$ of about 850 nm and a $\Delta\lambda$ of about 50 nm.

As further illustrated in FIG. 32, the reference path 3207 includes the fiber coupler 3270 as discussed above with respect to FIG. 31. The fiber coupler 3270 is configured to connect the reference path 3207 to at least two other paths 3271, 3272 switched by a mechanical switch 3275, for example, solenoid or galvanometer. When the switch 3275 is in reference position 1, the system will operate in anterior segment mode and when the switch is in reference position 2, it will operate in retinal scanning mode.

Figure 33:
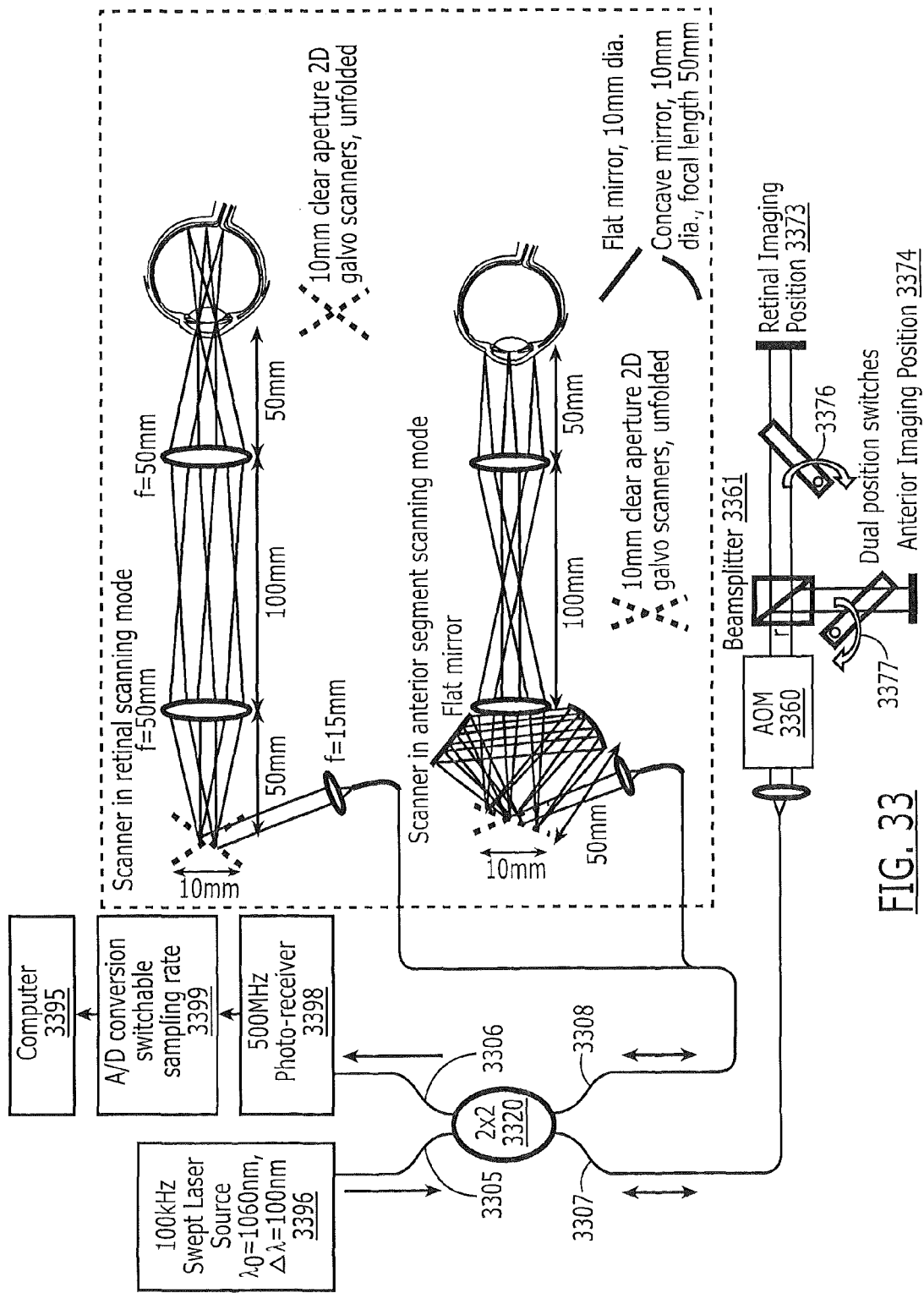
FIG. 33 is a block diagram illustrating a comprehensive ocular swept source OCT imaging system in accordance with some embodiments.

Referring now to FIG. 33, a system for ocular swept source OCT imaging will be discussed. As illustrated therein, the swept source OCT system includes a broadband optical source 3396, a source path 3305, a beam splitter/combiner 3320, a reference path 3307, a sample path 3308 with a scanning system and focal optics illustrated in FIGS. 30A and 30B configured to appropriately to image structures of the sample, such as the cornea, anterior chamber, iris, lens, posterior chamber, and retina of the eye, and a detector path 3306. The detector path 3306 includes a computer 3395, an A/D conversion switchable sampling rate 3399 and 500 MHz photo-receiver 3398. As illustrated, the source 3396 in FIG. 33 includes a 100 kHz Swept Laser source having a $\lambda_o$ of about 1060 nm and a $\Delta\lambda$ of about 100 nm.

As further illustrated in FIG. 33, the reference path 3307 a controller (AOM) 3360 as discussed above with respect to FIGS. 28A and 28B and 42. The controller 3360 is connected to a beamsplitter 3361, which is configured to split the light between first and second positions 3373, 3374. The positions connect the reference path 3307 to at least two other paths 3373, 3374 switched by dual position switches 3376 and 3377. When the switch is in reference position 1, the system will operate in retinal imaging mode 3373 and when the switch is in reference position 2, the system will operate in anterior imaging mode 3374.

As discussed above, for comprehensive FDOCT imaging of the eye by rapidly switching between imaging modes designed for imaging difference ocular structures along the visual axis, it would be desirable for the imaging depth (axial field of view) of each mode to be optimized for the expected length and desired axial sampling density of each structure. For example, for imaging of the entire anterior segment, the optimal imaging depth is the expected maximum anterior segment depth of the anticipated patient population, which may be as long as 6-8 millimeters. For imaging of the retina, which is less than 1.0 mm thick in most locations and contains many closely spaced layers and structures, it may be preferable for the retinal imaging mode to have a shorter imaging depth and denser sampling within it.

As discussed above, in all FDOCT systems, there is an inverse relationship between the imaging depth $z_{max}$ and the spectral sampling interval in wavenumber units $\delta_s k$ given by:

$$z_{max} = \frac{\pi}{2 \cdot \delta_s k}. \quad (3 \text{ above})$$

The total sampled spectral width is given by the spectral sampling interval $\delta_s k$ multiplied by the number of spectral samples acquired per A-scan, typically several thousand, and thus the depth sampling density is given by the imaging depth divided by the number of spectral samples (or some multiple of that number if interpolation is performed). In SDOCT systems, the spectral sampling interval $\delta_s k$ is typically fixed by the spacing of the pixels on the array detector used in the spectrometer and the magnification and spectral dispersion of the internal optical elements of the spectrometer. In SSOCT systems, however, the spectral sampling interval $\delta_s k$ is determined by the sweep rate of the light source and/or the electronic sampling rate of the analog to digital converter which is recording the SSOCT signal, at least one of which may be rapidly adjustable electronically or by other means. In the case of SSOCT, therefore, it will be desirable to adjust the spectral sampling interval and thus the imaging depth and depth sampling density (according to the prescription in Equation 3) on the fly according to the structure or part of the eye which is being imaged. This imaging depth switching may be coupled to the sample and reference arm mode switching embodiments described above with respect to FIGS. 28A through 33, such that when switching the sample arm optics and reference arm delay from the anterior segment to the retina, for example, the imaging depth is also switched to allow for optimal imaging depth and sampling density of retinal structures. In some embodiments, the imaging depth and depth sampling density may be varied within a single mode of the sample and reference arm optics, for example to switch between short imaging depth, high spatial sampling density imaging of the cornea and long imaging depth, lower spatial sampling density imaging of the entire anterior segment.

FDOCT systems exhibit a decrease in signal-to-noise ratio (SNR) as a function of path length difference between the sample and reference arms (and thus the distance from the origin in FDOCT images), which is related to the spectral resolution of the FDOCT system, $\delta_r k$ Rapid sensitivity falloff is a drawback in FDOCT systems because it limits the amount of the imaging depth which actually contains useful image information. The sensitivity "falloff" may be characterized by the imaging depth at which the sensitivity falls to 6 decibels below its value at the zero path length difference location. This value is inversely related to the system spectral resolution $\delta_r k$:

$$\hat{z}_{6dB} = \frac{2\ln(2)}{\delta_r k}. \quad (4 \text{ above})$$

In unmodified SDOCT systems, $\delta_r k$ is usually limited by the spectral resolution of the spectrometer (including the finite spacing of the CCD pixels and diffraction in the spectrometer). In unaltered SSOCT systems, $\delta_r k$ is typically limited by the instantaneous lineshape of the swept laser source, although other factors such as the bandwidth of the detection electronics may also come into play.

As discussed above, conventional methods exist for decreasing SNR falloff in FDOCT systems by introducing a comb filter into the FDOCT system (either in the source arm, both sample and reference arms, or detector arm), such that the spectral extent of light collected at each spectral sampling interval $\delta_s k$ is limited by the transmission characteristics of the comb filter rather than the spectral resolution of the spectrometer (in SDOCT) or the instantaneous linewidth of the swept laser source (in SSOCT) (U.S. Pat. No. 7,602,500). Such a comb filter may be implemented as a Fabry-Perot etalon or filter, having a free spectral range (FSR) set to be equal or nearly equal to the desired FDOCT spectral sampling interval $\delta_s k$, and a full width at half-maximum (FWHM) transmission peak width set to be equal or nearly equal to the desired FDOCT spectral resolution $\delta_r k$ required to achieve a given 6 dB falloff length $\hat{z}_{6dB}$ according to the formula in Eq. (4). Thus, the comb filter will essentially modify the spectrum reaching the FDOCT detector such that the optical bandwidth detected at each spectral sampling interval is decreased, thus decreasing SNR falloff.

In comprehensive ocular SSOCT systems as discussed above wherein the spectral sampling interval and depth sampling density are adjusted as per Equation 3 according to the structure or part of the eye which is being imaged, it is desirable to further implement a comb filter for decreasing the extent of SNR falloff which is also suitably adjustable to maintain the comb spacing or FSR as the spectral sampling interval is adjusted. In Fabry-Perot etalons, the FSR is related to the thickness of the etalon, the index of refraction of the material inside the etalon, and the angle of light incidence upon the etalon. According to some embodiments, one or more of these parameters should be varied in synchrony with changing the spectral sampling interval $\delta_s k$ in order to keep the comb filter peaks within their respective spectral sampling intervals. In some embodiments, this may be done by employing a so-called Fabry-Perot tunable filter, which utilizes a piezo-electric element to electronically tune its FSR. Electronic control of the FSR of such a filter may be electronically coupled to the mechanism for changing the spectral sampling interval $\delta_s k$, for example by changing the digitization rate of the analog-to-digital converter.

Several methods exist in the prior art for increasing the imaging depth $z_{max}$ by a factor of two by resolving the so-called "complex conjugate" or "mirror image" artifact in FDOCT, which not only limits the maximum imaging depth for a give spectral sampling interval but also introduces unwanted additional image artifacts. These prior art methods include techniques borrowed from phase shift interferometry involving multiple sequential or simultaneous A-scan acquisitions with reference path delays varying by a multiple of pi/2 radians.

For an SDOCT system designed for comprehensive ocular imaging according to all of the embodiments of the present inventive concept, the preferred embodiment for complex conjugate removal (CCR) is via sinusoidal phase modulation as discussed in U.S. Pat. No. 7,742,174, Sinusoidal phase modulation involves placement of a sinusoidal path length modulation in either the sample or reference arm of an SDOCT system which varies the differential path length between the arms with amplitude and phase given in the text preceding Equation (14) in U.S. Pat. No. 7,742,174, at a rate corresponding to $\Pi/4$ radians of sinusoidal modulation per A-scan integration time of the spectrometer. Then, each set of four sequential A-scan acquisitions are combined according to Equation (14) of U.S. Pat. No. 7,742,174 in order to generate an A-scan with total depth equal to $2*z_{max}$ as defined above. If the amplitude, phase and frequency of the sinusoidal modulation are set exactly as specified in U.S. Pat. No. 7,742, 174, then the resulting A-scan should theoretically be completely free of DC, auto correlation, and complex conjugate artifacts. However, slight deviations from perfection in achieving these parameters such as will be experienced in any real physical implementation of sinusoidal phase modulation may lead to a degradation of performance compared to the ideal result in the form of incomplete complex conjugate artifact suppression. Thus, an additional step of applying quadrature projection processing according to FIG. 2 of U.S. Patent Application Serial No. 2008/0170219 may be applied to improve the complex conjugate artifact rejection, at the cost of a small amount of reduced signal to noise ratio. Quadrature projection processing is an algorithmic step which does not require any hardware modification and which reduces the complex conjugate artifact from imperfectly phase modulated SDOCT data by forcing the real and imaginary parts of the recorded A-scan signal to be orthogonal.

For an SSOCT system designed for comprehensive ocular imaging according to all of the embodiments of the present inventive concept, the preferred embodiment for complex conjugate removal (CCR) is the so-called "heterodyne" CCR method, which involves introducing a frequency shift between the sample and reference arm light and thus shifting the carrier frequency of the image-bearing signal away from DC, about which the complex conjugate artifact is centered as discussed in U.S. Pat. No. 7,336,366. With the addition of this frequency shift, the A-scan free of complex conjugate artifact is found from the Fourier transform of the detected signal, centered at the frequency shift value. If an A/D converter is used which has much higher bandwidth than the SSOCT signal itself, then the frequency shift value can be set to be many times the frequency encoding the $z_{max}$ value of the A-scan, thus the complex conjugate artifact will be located far in frequency space away from the A-scan data. If a very high sweep speed is employed, however, such that the SSOCT signal already occupies a substantial fraction of the A/D converter bandwidth, then the complex conjugate artifact may only be shifted to the borders of the depth-doubled A-scan. This method of heterodyne CCR is consistent and will not interfere with the embodiments described above for switching between sample and reference arm imaging modes, switching SSOCT imaging depth, and switching of the comb filter FSR spacing to remain consistent with the spectral sampling interval.

Referring now to FIGS. 34 through 38, further embodiments of systems configured to switch between scanning modes will be discussed. As discussed above, for whole Eye imaging, two distinct methods of scanning typically must be used. The cornea, anterior chamber and lens scanning requires a telecentric type scanning which, as discussed above, can be defined as each filed point or angle of the scanning mirror produces focus rays which are parallel to the optical axis. Retinal scanning, on the other hand, typically requires that a collimated beam is impinging on the cornea with the conjugate of the scanning mirror be located at the pupil of the eye. For biometry, collimated light must be impinging on the cornea however since only axial scans are required the conjugate of the scanning mirror does not need to be placed at the pupil of the eye. Conventional OCT systems require separate optics to do each type of scan. The challenge to doing either telecentric scanning plus axial retinal scanning for biometry or telecentric scanning plus retinal scanning for true dual scan modes is developing a method to rapidly change the imaging optics or rapidly alter the characteristics of the imaging optics.

Various embodiments for switching between modes will now be discussed with respect to FIGS. 34 through 38. In addition to switching techniques to change from concentric imaging of the retina to telecentric imaging of the cornea, a zoom lens type optical translation can be used to move between the two modes of operation. The advantage to these embodiments is that it affords the ability to focus the scanning beam at different points in the eye for the highest lateral resolution.

Figure 34:
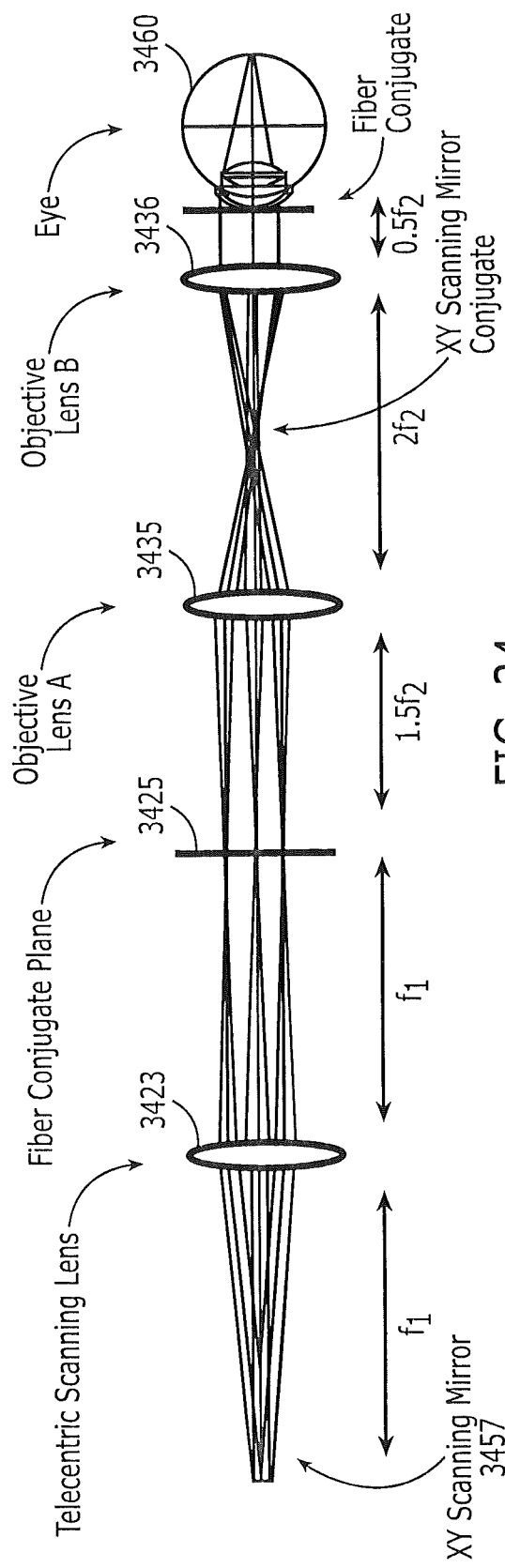
FIG. 34 is a diagram illustrating an optical layout for telecentric scanning mode in accordance with some embodiments.

Referring first to FIG. 34, an optical layout for telecentric scanning mode will be discussed. As illustrated, the system of FIG. 34 for imaging an eye 3460 includes an XY scanning mirror 3457, a telecentric scanning lens 3423, a fiber conjugate plane 3425, first and second objective lenses 3435 and 3436, XY scanning mirror conjugate 3458 and a fiber conjugate 3459. The telecentric scanning lens 3423 forms a conjugate of the input fiber (not shown) which is an intermediate telecentric image plane. Therefore, the focal length of the telecentric scanning lens is totally independent of the objective focal length and is selected for both optimum mechanical layout and as well as overall system numerical aperture. The combined focal length of the objective is selected to give the widest possible field of view at the desired working distance or distance from the last optical element to the cornea of the eye. As used herein, $f_1$ is equal to the focal length of the telecentric scanning lens and $f_2$ is equal to the sum of the focal lengths of objective lens 1 and objective lens 2.

Figure 35:
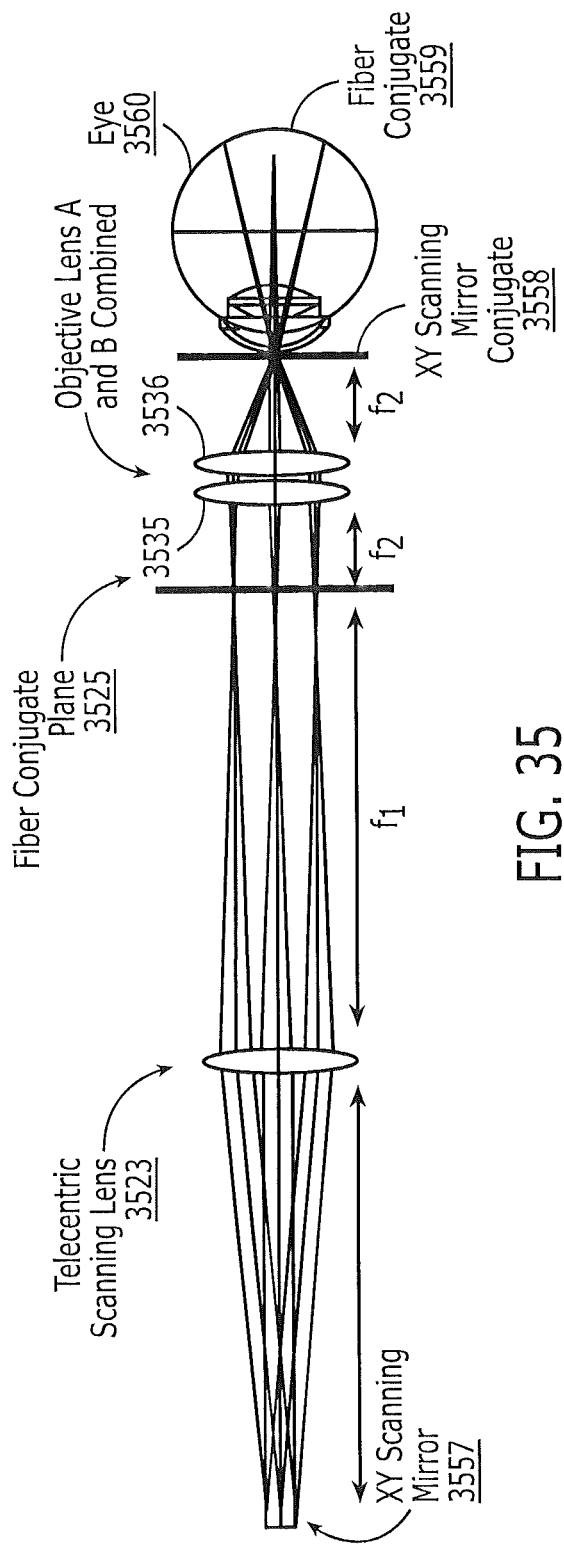
FIG. 35 is a diagram illustrating an optical system in concentric or retinal scanning mode in accordance with some embodiments.

Referring now to FIG. 35, the system of FIG. 35 for imaging an eye 3560 includes an XY scanning mirror 3557, a telecentric scanning lens 3523, a fiber conjugate plane 3525, combined first and second objective lenses 3537, XY scanning mirror conjugate 3558 and a fiber conjugate 3559. The optical system of FIG. 35 is in the Concentric or Retinal scanning mode. As illustrated, in this configuration the objectives lenses 3537 are combined by bringing them into close proximity to one another. This combines the optical power of the objective lenses and moves the scanning mirror conjugate to the cornea and thus the fiber is imaged onto the retina. As compared to the spacing in the telecentric mode, the travel of objective lenses is the differential between the two settings by the factors shown in FIG. 34. The working distance or the distance from the last optical element to the eye however remains fixed.

In FIG. 35, $f_1$ is equal to the focal length of the telecentric scanning lens 3523 and $f_2$ is equal to the sum of the focal lengths of objective lens 1 and 2 3537. The OCT reference arm position typically tracks the lens translation. Other combinations of focal lengths and spacing can be used without departing from the scope of embodiments discussed herein. Thus, as illustrated in FIGS. 34 and 35, objective lens A 3435 slides to change from iris pivot mode (object lens A 3435 proximate objective lens B 3436) to telecentric mode (objective lens A 3435 forms relay to objective lens B 3436).

Figure 36:
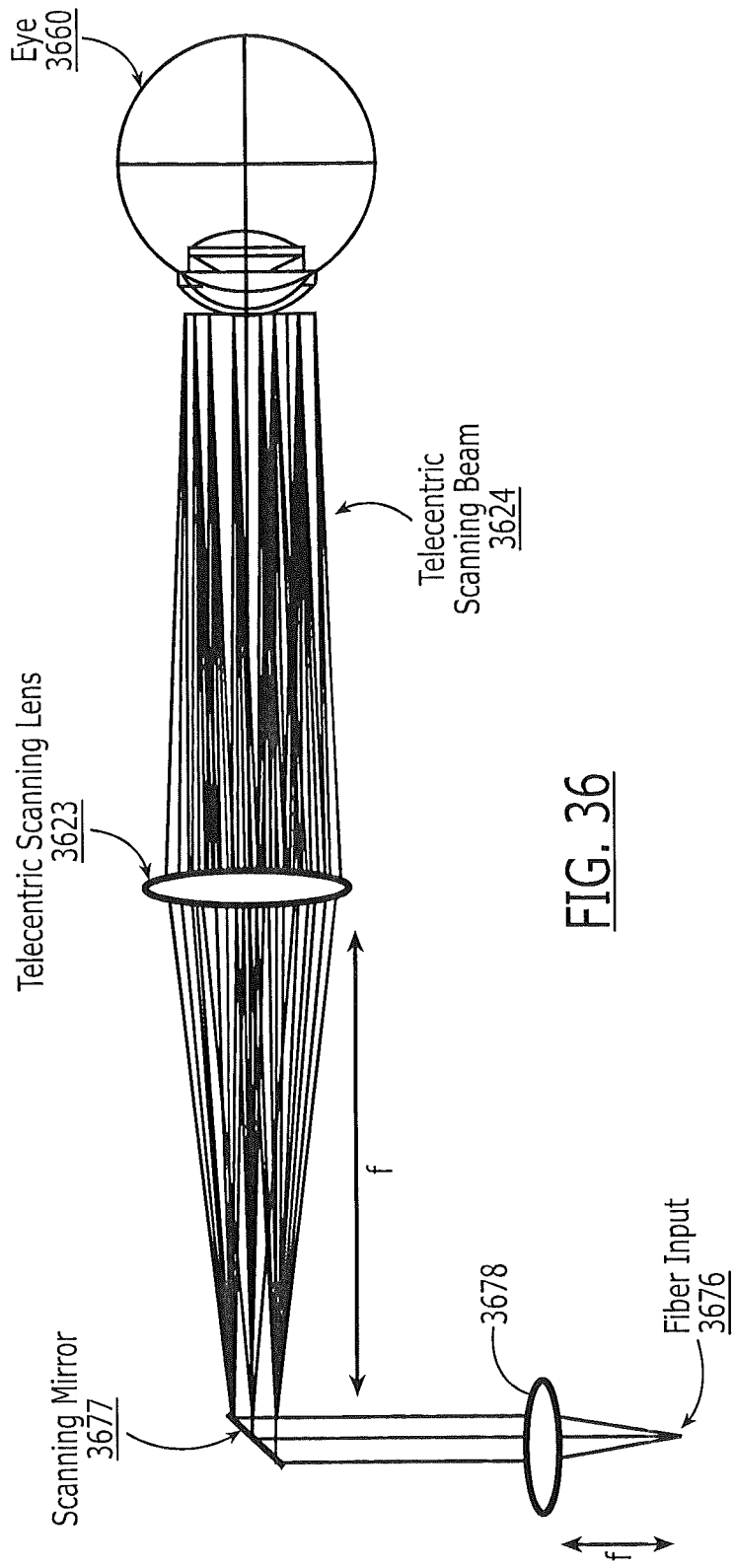
FIG. 36 is a diagram illustrating an optical layout for telecentric scanning mode in accordance with some embodiments.

Referring now to FIG. 36, a system in telecentric mode for imaging the cornea of the eye 3660 includes a fiber input 3676, a collimating lens 3678, a scanning mirror 3677, a telecentric scanning lens 3623, and a telecentric scanning beam. For the case of biometry, a concentric scan is not necessary and changing the scan mode from telecentric to collimated will allow the OCT beam to be focused onto the retina. To change the system of FIG. 36 from telecentric to collimated, the collimating lens 3778 can be translated by a distance equal to its focal length as illustrated in FIG. 37. The system in FIG. 37 includes a collimating lens 3778, a scanning mirror 3777, a telecentric scanning lens 3723, a collimated beam 3787 and a fiber conjugate 3788.

In some embodiments, to change the system of FIG. 36 from telecentric to collimates, a secondary lens 3879 can be inserted behind the collimating lens 3878 to change the focal position and illustrated in FIG. 38. The system of FIG. 38 includes a collimating lens 3878, a scanning mirror 3877, a telecentric scanning lens 3823, a collimated beam 3887 and a fiber conjugate 3888.

Some specific embodiments will now be discussed. To achieve accommodation for both myopic and hyperopic the lens set must be shifted from the conjugate plane with an offset of 2.0 mm for a +12 diopter accommodation and −1.75 mm for a −12 diopter accommodation. The lens positions and spacing for telecentric imaging mode however remain constant. Therefore the translation mechanism allows for the translation of the lens pair when moved into the retinal position.

To translate the lenses from telecentric to retinal mode imaging, a standard zoom lens double helix drive can be incorporated for both manual and automated actuation. Automated means can be accomplished with, for example, stepper motors, piezo motor, solenoids or voice coils, but are not limited thereto. With proper mechanical coupling, each methodology has the capacity to switch modes well within a single second. Both stepper and piezo motor drives afford the ability to add programmability to the lens translation allow intermediate surfaces to be imaged at a high lateral resolution.

Due to the physical property of diffraction, high resolution scanning lenses are constrained to have low depth of focus resulting in decreasing lateral resolution as the distance from the image plane is increased. To alleviate this issue long depth of focus optics can be designed but at the sacrifice of resolution. The depth of focus (d) is defined as:

$$d = 2\pi \omega_o^2 / \lambda \quad (38)$$

where $\omega_o$ is the Airy radius which is the radius of the first diffraction minimum of the focuses spot and $\lambda$ is the wavelength of light. Therefore as the relation shows, with the wavelength fixed, the larger the Airy radius the greater the depth of field and since the Airy radius also defines the scanning resolution, the lower the resolution.

Likewise, it is possible to derive the required Airy radius based upon the desired scan depth as follows:

$$\omega_o \sqrt{d\lambda/2\pi} \quad (39)$$

In embodiments where a desired scan depth for the cornea to lens is a distance of 6.55 mm, the scanning resolution will be limited to 29.6 μm. This can be achieved by simply changing the focal length of the collimator used in system proportionally to the focal length of the scanning optics and making no other changes to the scanning optics from the current product offering. No additional optics design work is required. Since the current telecentric scanning optics have an Airy disk radius of 12 μm a 2.5× reduction in the focal length of the collimator will produce the 29.6 μm Airy radius required.

For volume phase holographic grating based spectrometer design, the imaging depth is related to the dispersion characteristics of the spectrometer in the following expression:

$$Z = \lambda_c^2 / 4n\lambda_s \quad (40)$$

Where
δ=source bandwidth (nm)
$\lambda_c$=source center wavelength (nm)
p=pixels (detector channels)
$\lambda_s$=spectrometer wavelength spacing=δ/p
n=index of refraction Therefore in order to design the spectrometer for the maximum desired imaging window depth of 6.55 mm for the region of cornea to the posterior surface of the lens the above equation is solved for With $\lambda_s = \delta/p$ equation (1) becomes $$Z = p\lambda_c^2 / 4n\delta \quad (41)$$

Given that p is determined by available detectors and therefore is a fixed value solving for in becomes, $$\delta = p\lambda_c^2 / 4nZ \quad (42)$$

Alternatively, setting δ to a known value and solving for $\lambda_c$ in nanometers leads to, $$\lambda_c = \sqrt{(4n\delta Z/p)} \quad (43)$$

The determination of the optimum values for $\lambda_c$ and δ are based upon the design models for the source.

Further definition of the design parameters can be obtained by relating the image size to the detector pixel size in order to determine the spectrometer focal length required. Assuming a collimated beam input to the grating the diffraction limited spot size can be represented by the following expression:

$$D = 1.22\lambda_c (f/d) \qquad (44)$$

Where f is the focal length of the spectrometer imaging optics and d is typically the lens aperture diameter which in this case is equivalent to the spectrometer input collimated beam diameter. Solving for (f/d), $$(f/d) = D/1.22\lambda_c \qquad (45)$$

Therefore given a pixel size of 10 μm and setting the target diffraction limited image spot radius to the detector pixel size with a 75% fill factor as is standard practice yields a spot diameter of 7.5 μm. From Equation 45, we can determine the ratio of the focal to input beam diameter, $$(f/d) = 3.5 \qquad (46)$$

From expression (46) for a collimated beam of 25 mm in diameter the required focal length of the spectrometer imaging optics is 89 mm. Conversely, setting the focal length to 100 mm requires a 28 mm collimated beam input. The determination of which parameter to solve for is based solely on the design constraints of the spectrometer.

Using the grating equation:

$$\lambda_c f = \sin\theta_i + \sin\theta_d \qquad (47)$$

Where
$\lambda_c$ = source center wavelength
f = spatial frequency of the grating
$\theta_i$ = angle of incidence
$\theta_d$ = angle of diffraction For VPH grating designs $\theta_i = \theta_d$, Solving for f equation 5 is reduced to:

$$f = 2\sin\theta/\lambda_c \qquad (48)$$

With the practical upper limit established by:

$$f = 2/\lambda_c \qquad (49)$$

Since the dispersion efficiency of the VPH grating is inversely proportional to the spatial frequency design optimization is directed toward reducing the spatial frequency. The optical design of the spectrometer is also critical in selecting the grating dispersion value. Since the array has a predetermined physical length and the center wavelength and bandwidth are fixed by the desired imaging depth, the dispersion is selected to insure full coverage of the spectral bandwidth across the detector array.

By definition, the dispersion of the grating is the rate of change of the angle of diffraction with wavelength for a fixed angle of incidence or $\Delta\theta/\Delta\lambda$ which from a differentiation of equation 47 yields:

$$\Delta\theta/\Delta\lambda = f/\cos\theta \qquad (50)$$

The dispersion of the grating is also related to the required geometry of the spectrometer optics. For a given array length and focal length of the imaging optics the angle of dispersion can be given as:

$$\Phi = 2\tan^{-1}(A/2f) \qquad (51)$$

where f is the focal length of the imaging optics and A is the detector array length.

From equation (50) the grating dispersion relates the dispersion angle by:

$$\Phi = a f \delta/\cos\theta = 2\tan^{-1}(A/2f) \qquad (52)$$

where a is the unit conversion from radians/mm to degrees/nm and f is determined by the detector pixel size as stated in equation 46.

The expression can be reduced as follows:

$$(a\delta/\lambda_c)\tan\theta = \tan^{-1}(A/2f) \qquad (53)$$

Solving for θ:

$$\theta = \tan^{-1}[(\lambda_c/a\delta)\tan^{-1}(A/2f)] \qquad (54)$$

From the above equations, the required dispersion angle can be calculated for a given spectrometer layout. The parameters required as inputs to the equations are the detector pixel size which defines the required focal length, (A) the linear dimension of the detector array, ($\lambda_c$) the center wavelength of the source and (δ), the bandwidth of the source. From the calculated dispersion value, the grating frequency and grating angle can be calculated resulting in a complete characterization of the spectrometer design.

Figure 39:
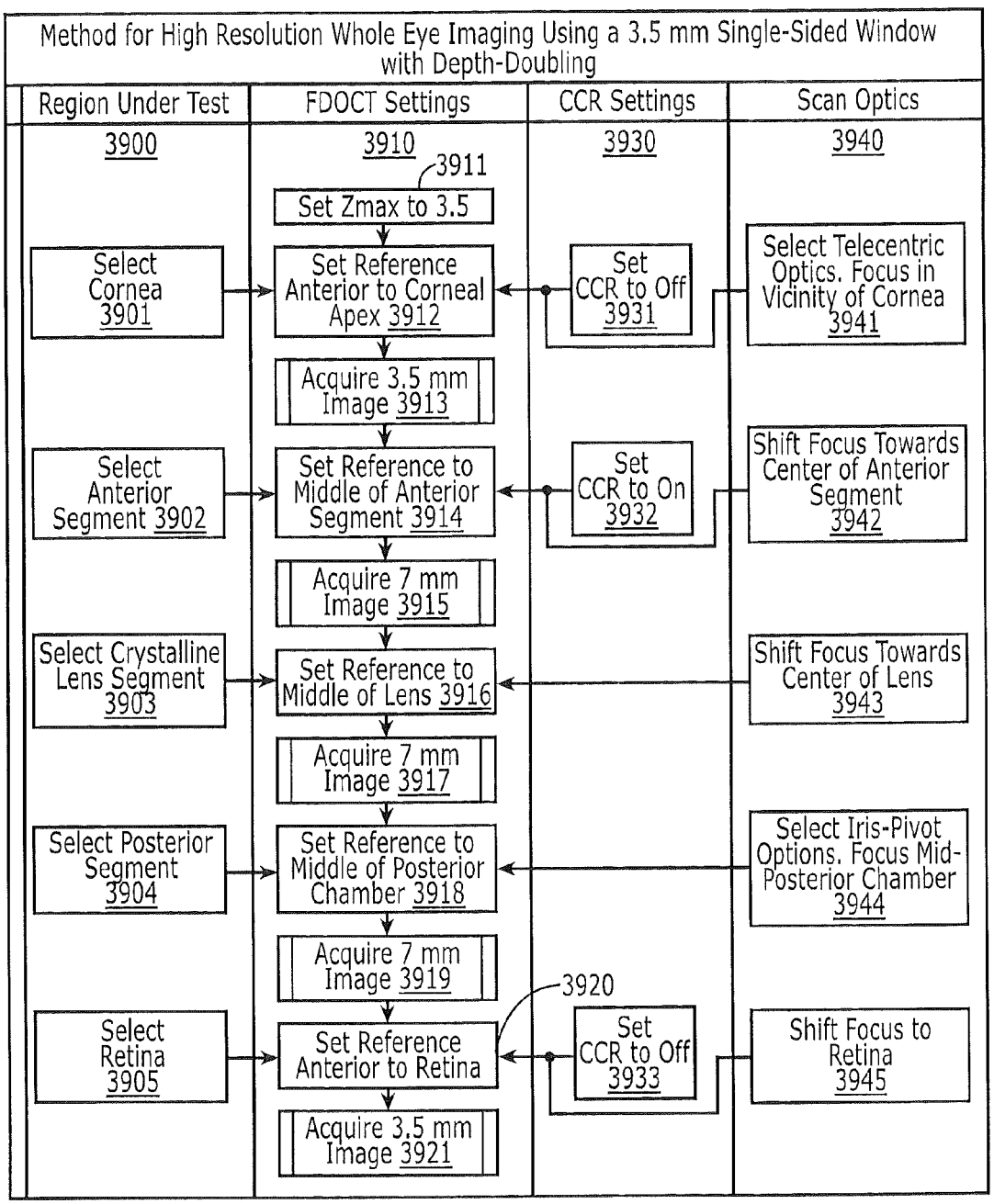
FIGS. 39 through 41 are flowcharts illustrating scanning methods in accordance with various embodiments discussed herein.
Figure 40:
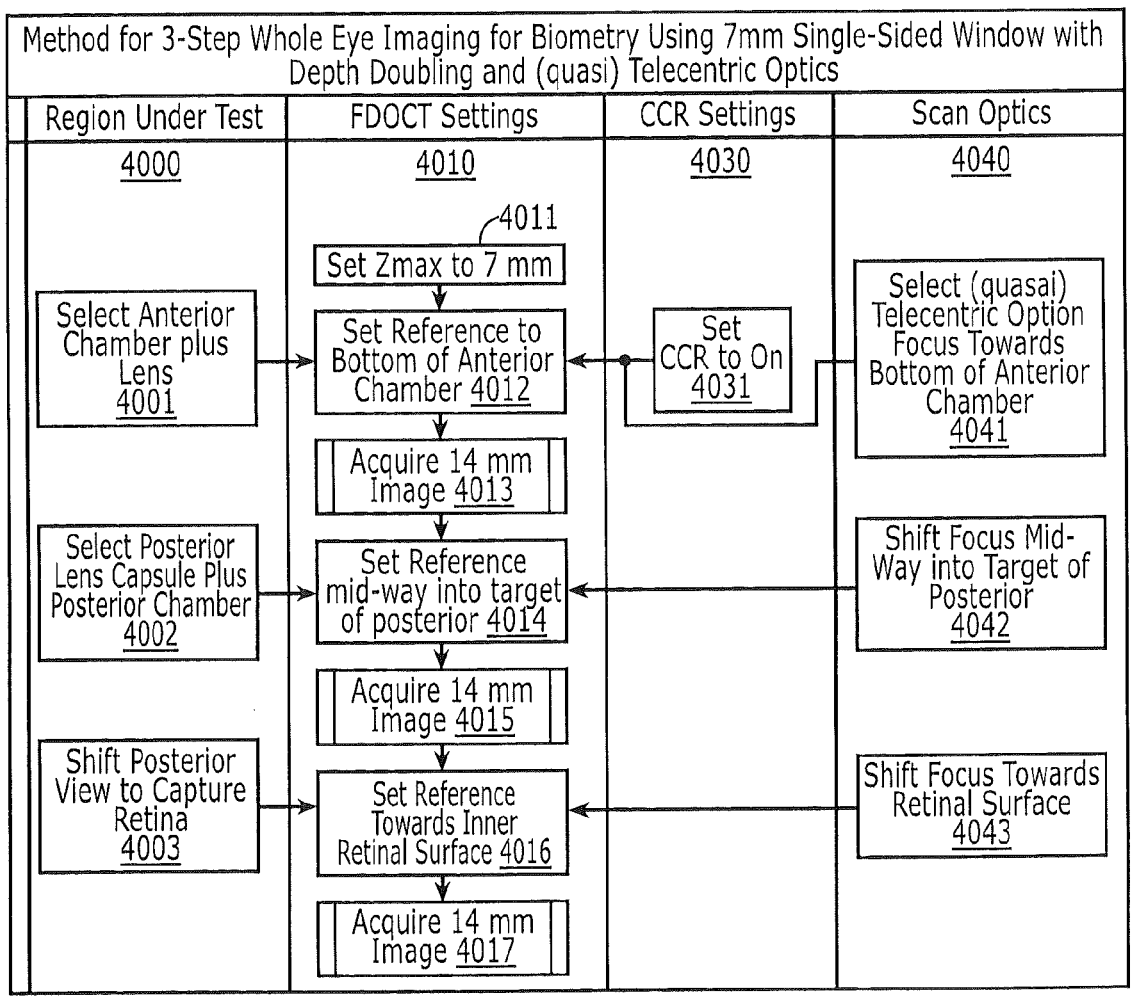
Figure 41:
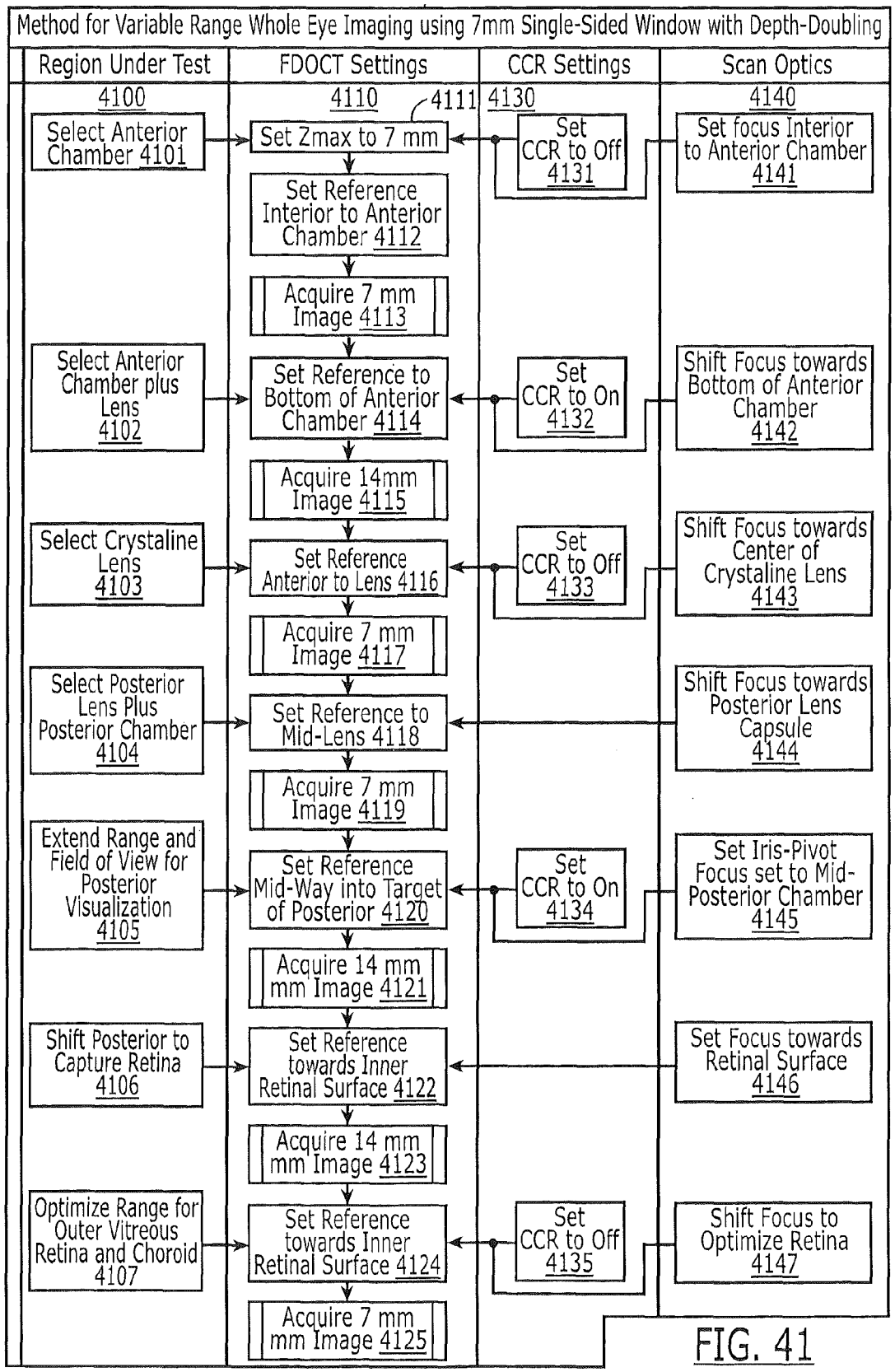

Various methods for whole eye imaging are illustrated in the flowcharts of FIGS. 39-41. In particular, referring first to FIG. 39, methods for high resolution whole eye imaging using a 3.5 mm single-sided window with depth doubling will be discussed. As illustrated in FIG. 39, a region under test may be selected may be selected in block 3900. As illustrated, the region under test 3900 may be the cornea 3901, the anterior segment 3902, the crystalline lens segment 3903, the posterior segment 3904 or the retina 3905. It will be understood that embodiments of the present inventive concept are not limited to the regions in box 3900 and that more or less regions may be enumerated without departing from the scope of the present inventive concept.

Once the region is selected (block 3900) the FDOCT settings 3910 are determined. For example, in some embodiments $z_{max}$ is set to 3.5 mm (block 3911). At this point if the cornea 3901 is the selected region, the reference is set to anterior to corneal apex (block 3912) and a 3.5 mm image may be acquired (block 3913). If the anterior segment is selected (block 3902), the reference is set to middle of anterior segment (block 3914) and a 7.0 mm image may be acquired (block 3915). If the crystalline lens segment is selected (block 3903), the reference is set to middle of lens (block 3916) and a 7.0 mm image may be acquired (block 3917). If the posterior segment is selected (block 3904), the reference is set to middle of posterior chamber (block 3918) and a 7.0 mm image may be acquired (block 3919). If the retina is selected (block 3905), the reference is set to anterior to retina (block 3920) and a 3.5 mm image may be acquired (block 3921).

As further illustrated in FIG. 39, the CCR setting (3930) is set to "off" if the cornea (3901) or the retina (3905) is selected as the region under test (3900) and set to "on" if the anterior segment (3902) is selected as the region under test (3900).

Finally, as further illustrated in FIG. 39, scan options (3940) may also be selected/set. For example, if the cornea 3901 is the selected region, telecentric optics are selected focused in the vicinity of the cornea (block 3941). If the anterior segment is selected (block 3902), the focus of the optics is shifted towards center of the anterior segment (block 3942). If the crystalline lens segment is selected (block 3903), the focus of the optics may be shifted towards the center of the lens (block 3943). If the posterior segment is selected (block 3904), iris-pivot optics are selected with focus on mid-posterior chamber (block 3944). If the retina is selected (block 3905), the focus is shifted to the retina (block 3945).

Referring now to FIG. 40, methods for three-step whole eye imaging for Biometry using 7.0 mm single-sided window with depth doubling and quasi-telecentric optics will be discussed. As illustrated in FIG. 40, a region under test may be selected may be selected in block 4000. As illustrated, the region under test 4000 may be anterior chamber plus lens 4001, the posterior lens capsule plus posterior chamber 4001 or the posterior view to capture retina 4003. It will be understood that embodiments of the present inventive concept are not limited to the regions in box 4000 and that more or less regions may be enumerated without departing from the scope of the present inventive concept.

Once the region is selected (block 4000) the FDOCT settings 4010 are determined. For example, in some embodiments $z_{max}$ is set to 7.0 mm (block 4011). At this point if the anterior chamber plus lens 4001 is the selected region, the reference is set to bottom of anterior chamber (block 4012) and a 14 mm image may be acquired (block 4013). If the posterior lens capsule plus posterior chamber is selected (block 4002), the reference is set to mid-way into target of posterior (block 4014) and a 14.0 mm image may be acquired (block 4015). If the posterior view to capture retina is selected (block 4003), the reference is set to towards inner retinal surface (block 4016) and a 14 mm image may be acquired (block 4017).

As further illustrated in FIG. 40, the CCR setting (4030) is set to "on" if the anterior chamber plus lens (4001) is selected as the region under test (4000).

Finally, as further illustrated in FIG. 40, scan options (4040) may also be selected/set. For example, if the anterior chamber plus lens (4001) is the selected region, telecentric optics are selected focused towards a bottom of the anterior chamber (block 4041). If the posterior lens capsule plus posterior chamber is selected (block 4002), the focus of the optics is shifted midway into target of the posterior (block 4042). If the posterior view to capture retina is selected (block 4003), the focus of the optics may be shifted towards the retinal surface (block 4043).

Referring now to FIG. 41, methods for variable range whole eye imaging using a 7.0 mm single-sided window with depth doubling will be discussed. As illustrated in FIG. 41, a region under test may be selected may be selected in block 4100. As illustrated, the region under test 4100 may be the anterior chamber 4101, the anterior chamber plus lens 4102, the crystalline lens 4003, the posterior lens plus posterior chamber 4104, posterior segment 4105, posterior view to capture retina 4106 or retina and choroid 4107. It will be understood that embodiments of the present inventive concept are not limited to the regions in box 4100 and that more or less regions may be enumerated without departing from the scope of the present inventive concept.

Once the region is selected (block 4100) the FDOCT settings 4110 are determined. For example, in some embodiments $z_{max}$ is set to 7.0 mm (block 4111). At this point if the anterior chamber 4001 is the selected region, the reference is set to interior to anterior chamber (block 4112) and a 7.0 mm image may be acquired (block 4113). If the anterior chamber plus lens (block 4102) is selected, the reference is set to bottom of anterior chamber (block 4114) and a 14.0 mm image may be acquired (block 4115). If the crystalline lens is selected (block 4103), the reference is set anterior to lens (block 4116) and a 7.0 mm image may be acquired (block 4117). If the posterior lens plus posterior chamber is selected (block 4104), the reference is set to mid-lens (block 4118) and a 7.0 mm image may be acquired (block 4119). If the extended range and field of view for posterior visualization is selected (block 4105), the reference is set to midway into target of posterior (block 4120) and a 14 mm image may be acquired (block 4121). If the posterior view to capture retina is selected (block 4106), the reference is set to towards inner retinal surface (block 4122) and a 14 mm image may be acquired (block 4123). If the optimized range for outer vitreous, retina and choroid is selected (block 4107), the reference is set to towards inner retinal surface (block 4124) and a 7.0 mm image may be acquired (block 4125).

As further illustrated in FIG. 41, the CCR setting (4130) is set to "off" if the anterior chamber (4101), crystalline lens (4103) or the optimized range for outer vitreous, retina and choroid is selected (block 4107) is selected as the region under test (4100) and set to "on" if the anterior chamber plus lens (4102) or extended range and field of view for posterior visualization is selected (block 4105) is selected as the region under test (4100).

Finally, as further illustrated in FIG. 41, scan options (4140) may also be selected/set. For example, if the anterior chamber (4101) is the selected region, the optics may be focused interior to the anterior chamber (block 4141). If the anterior chamber plus lens is selected (block 4102), the focus of the optics is shifted towards a bottom of the anterior chamber (block 4142). If the crystalline lens is selected (block 4103), the focus of the optics may be shifted towards the center of the crystalline lens (block 4143). If the posterior lens plus posterior chamber is selected (block 4104), optics are focused on posterior lens capsule (block 4144). If the extended range and field of view for posterior visualization is selected (block 4105), the iris-pivot focus is set to mid-posterior chamber (block 4145). If the posterior view to capture retina is selected (block 4106), the focus is set towards the retinal surface (block 4145). If the optimized range for outer vitreous, retina and choroid is selected (block 4107), the focus is shifted to optimize the retina (block 4147).

In the drawings and specification, there have been disclosed exemplary embodiments of the present inventive concept. However, many variations and modifications can be made to these embodiments without substantially departing from the principles of the present inventive concept. Accordingly, although specific terms are used, they are used in a generic and descriptive sense only and not for purposes of limitation, the scope of the inventive concept being defined by the following claims.

That which is claimed is:

1. An optical coherence tomography system for imaging a whole eye, the system comprising:
    a sample arm including focal optics configured to switch between at least two scanning modes,
        wherein the at least two scanning modes comprise an anterior segment scanning mode and a retinal scanning mode;
        wherein the sample arm of the system in retinal scanning mode comprises a collimator, a two-axis scanning mirror assembly, and a scan lens assembly, and an objective lens; and
        wherein the focal optics of the sample arm are configured to reposition at least one movable lens to change an optical coherence tomography (OCT) scan beam from a collimated beam for imaging an emmetropic eye to one of a converging beam for imaging a myopic eye and a diverging beam for imaging a hyperopic eye;
    a mechanical means for modifying components within an optical pathway of the sample arm to switch the scanning mode between the retinal scanning mode and the anterior segment scanning mode; and
    a reference arm coupled to the sample arm and comprising a means for discrete switching between two path delays in coordination with switching between the at least two scanning modes,
        wherein a first path delay is configured to match an optical path length of the OCT scan beam in the retinal scanning mode and a second path delay is configured to match an optical path length of the OCT scan beam in anterior segment scanning mode, wherein the sample arm of the system in the anterior segment scanning mode comprises a collimating lens, two two-axis scanning mirror assemblies, a scan lens, an objective lens and a curved mirror placed a focal length (f) away from a first of the two two-axis scanning mirror assemblies; and wherein a second of the two two-axis scanning mirror assemblies is configured to direct re-directed collimated light in a triangular pattern towards the curved mirror causing the optical path length of the system to be longer in the anterior segment scanning mode than in the retinal scanning mode.

2. An optical coherence tomography system for imaging a whole eye, the system comprising:

a sample arm including focal optics configured to switch between at least two scanning modes,
   wherein the at least two scanning modes comprise an anterior segment scanning mode and a retinal scanning mode;
   wherein the sample arm of the system in retinal scanning mode comprises a collimator, a two-axis scanning mirror assembly, and a scan lens assembly, and an objective lens; and
   wherein the focal optics of the sample arm are configured to reposition at least one movable lens to change an optical coherence tomography (OCT) scan beam from a collimated beam for imaging an emmetropic eye to one of a converging beam for imaging a myopic eye and a diverging beam for imaging a hyperopic eye;

a mechanical means for modifying components within an optical pathway of the sample arm to switch the scanning mode between the retinal scanning mode and the anterior segment scanning mode; and a reference arm coupled to the sample arm and comprising a means for discrete switching between two path delays in coordination with switching between the at least two scanning modes,
   wherein a first path delay is configured to match an optical path length of the OCT scan beam in the retinal scanning mode and a second path delay is configured to match an optical path length of the OCT scan beam in anterior segment scanning mode, wherein the sample arm of the system in the anterior segment scanning mode comprises a collimating lens, a two-axis scanning mirror assembly, a scan lens, an objective lens, a flat mirror and a concave mirror placed a focal length (f) away from the two-axis scanning mirror assembly, wherein light incident on the two-dimensional scanner pair is deviated such that the an incident collimated beam is directed into a separate path consisting of the flat mirror and the concave mirror.

* * * * *